US006420610B1

(12) United States Patent
Nakamura et al.

(10) Patent No.: US 6,420,610 B1
(45) Date of Patent: Jul. 16, 2002

(54) SILVER HALIDE PHOTOGRAPHIC LIGHT-SENSITIVE MATERIAL, AROMATIC ALDEHYDE DERIVATIVE COMPOUND, AND IMAGE-FORMING METHOD

(75) Inventors: Takashi Nakamura; Toshiyuki Makuta; Koki Nakamura, all of Minami-ashigara (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/661,196

(22) Filed: Sep. 13, 2000

Related U.S. Application Data

(62) Division of application No. 09/161,961, filed on Sep. 29, 1998, now Pat. No. 6,174,656.

(30) Foreign Application Priority Data

Sep. 30, 1997 (JP) .............................................. 9-265568
Sep. 30, 1997 (JP) .............................................. 9-266793

(51) Int. Cl.$^{7}$ ....................... C07C 47/52; C07C 47/546; C07D 493/00

(52) U.S. Cl. ....................... 568/425; 568/440; 568/441; 568/442; 568/439; 549/430

(58) Field of Search ................................. 568/442, 592, 568/716, 425, 439, 440, 441; 549/430

(56) References Cited

U.S. PATENT DOCUMENTS 5,256,525 A 10/1993 Southby et al.
5,538,834 A 7/1996 Buchanan et al.

FOREIGN PATENT DOCUMENTS

DE 195 38 788 A1 4/1997

OTHER PUBLICATIONS

Mahajan et al, Arch.Microbiol., 161(5), 425–33, (1994).*
Elix et al, Aust.J.Chem., 40(11), 1841–50 (1987).*
Warshawsky et al, React.Polym.,Ion. Exch.,Sorbents 2(4), 301–4 (1984).*

* cited by examiner

*Primary Examiner*—Sreeni Padmanabhan
(74) *Attorney, Agent, or Firm*—Sughrue Mion, PLLC

(57) ABSTRACT

Aromatic aldehyde compounds of formula (4) and (6) are disclosed,

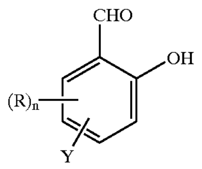

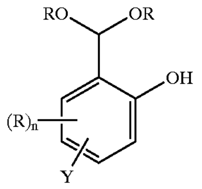

wherein Y is a methylene group with various substitutions and R represents various substituents.

4 Claims, 2 Drawing Sheets

SILVER HALIDE PHOTOGRAPHIC LIGHT-SENSITIVE MATERIAL, AROMATIC ALDEHYDE DERIVATIVE COMPOUND, AND IMAGE-FORMING METHOD

This is a divisional of application Ser. No. 09/161,961 filed Sep. 29, 1998, now U.S. Pat. No. 6,174,656 disclosure of which is incorporated herein by reference.

FIELD OF THE INVENTION

The present invention relates to a novel photographic recording material containing a photographically useful compound in a protected form. The present invention also relates to an image-forming method, in which a photographically useful compound is released, imagewise or uniformly, from its protected form. Further, the present invention relates to a novel benzaldehyde derivative having a structure required for development of the function thereof.

Further, the present invention relates to a color photographic technique, and more particularly to a silver halide color photographic light-sensitive material that can keep up with the trend of environmental protection and simple rapid processing and that is excellent in color-forming property, storage stability, fastness of dye image, and hue to be obtained, and a color-image forming method.

BACKGROUND OF THE INVENTION

Generally, in a photographic light-sensitive material, building, into the light-sensitive material, a photographically useful compound that is necessary for image formation, has many advantages, such as that the preparation of a development processing solution is made simple, the control of the developing solution is made easy, the composition of the developing solution changes less, and the treatment of the waste liquor is made easy. However, building, into a light-sensitive material, a photographically useful compound that is susceptible to air oxidation or hydrolysis, or that is thermally unstable, is not easy. For example, building an aromatic primary amine, which is a color-developing agent, into a light-sensitive material has many defects, such as that, for example, desensitization, fogging, or stain of the light-sensitive material occurs during its storage, and satisfactory color formation is not obtained. Therefore, building an aromatic primary amine, which is a color-developing agent, into a light-sensitive material has not yet been put into practice.

To cope with these problems, a method has been attempted so far in which a photographically useful compound is built into a light-sensitive material in the form of a protected compound that is made inactive or is relatively lowered in activity, and the built-in compound is activated by deprotecting the compound during the processing, utilizing a change in pH during the processing. However, the defect of this method is that it is difficult to control satisfactorily the difference between the activity of the protected compound and the activity of the deprotected compound; for example, the protection was too stable to be deprotected completely by a change in the processing pH, or the photographically useful compound that is an active substance was released partially under the conditions during long-term storage. Such protective groups are described, for example, in U.S. Pat. Nos. 4,690,885, 4,358,525, 4,554,243, and 5,019,492.

As techniques free from the defects described above for the deprotection of a protected photographically useful compound by a suitable method, image-forming methods in which a di-nucleophilic agent having a function for selective deprotection is added to a processing solution, are reported in U.S. Pat. No. 5,256,525 and JP-A-9-133990 ("JP-A" means unexamined published Japanese patent application). Further, as a similar technique, an image-forming method in which the selective deprotection is carried out in the presence of peroxide anions, is reported in U.S. Pat. No. 5,538,834.

In these techniques, however, although the addition of the di-nucleophilic agent or the peroxide to the processing solution accelerates the deprotection at the time of the processing, it uses a difference in the reaction rate for hydroxide ions, and the employed deprotection reaction can proceed more or less even with hydroxide ions alone. Accordingly, both the activity at the time of processing and the storage stability described above were difficult to be secured completely at the same time, and the level of securing them was still unsatisfactory.

On the other hand, that a carbonyl group is converted into a hydroxyl group in an alkaline solution via a rearrangement reaction in the presence of a peroxide, such as a peracid, is widely known as an organic synthesis reaction called the Dakin reaction or the Bayer-Villiger reaction. This reaction does not proceed at all in the absence of a peracid or a peroxide. Accordingly, it has been found that if this reaction is utilized, both the activity at the time of processing and the storage stability described above can be secured completely at the same time.

In the meantime, generally in a color photographic light-sensitive material, when the said light-sensitive material is exposed to light imagewise and then subjected to color-development, the oxidized p-phenylenediamine derivative reacts with a coupler to form an image. In this system, color reproduction by the subtractive color technique is used, and, to reproduce blue, green, and red colors, couplers that form dye images of yellow, magenta, and cyan in color, respectively complementary to blue, green, and red, are used.

Color development is attained by immersing an exposed color photographic light-sensitive material in an aqueous alkali solution containing a p-phenylenediamine derivative (color developer). However, the p-phenylenediamine derivative (a photographically useful compound) made into an aqueous alkali solution is unstable and is apt to deteriorate with time. Therefore there is no problem when the processing quantity of the color photographic light-sensitive material is large and the replenisher is frequently replenished, but when the processing quantity is small and the replenisher is less replenished, the color developer cannot withstand use for a long period of time and is required to be replaced, which is a problem.

If the p-phenylenediamine derivative in the color developer is removed from the processing solution, the above problem of deterioration with time and the complicated problem of the liquid-waste treatment of the color developer can be solved. However, when the p-phenylenediamine derivative is removed from the processing solution, color formation itself does not take place. In order to form color with an alkali solution from which the p-phenylenediamine derivative is removed (hereinafter abbreviated to an activator solution), suitably a p-phenylenediamine derivative, or a compound that can act like it, is contained in a light-sensitive material.

However, if a p-phenylenediamine derivative is contained in a light-sensitive material as it is, when the unprocessed light-sensitive material is stored for a long period of time, for example, it is oxidized with oxygen, to form stain, or it reacts with the coexistent couplers, to produce dyes, causing deterioration of images. Further, it affects the coexistent silver halide, causing image formation to fluctuate.

As a system for building in a compound other than p-phenylenediamine derivatives, there is a method in which a stable color-forming reducing agent is built into a light-sensitive material. For instance, there can be mentioned methods in which a hydrazine compound is built into a hydrophilic colloid layer, as described, for example, in EP-A-0 544 491 (A1), EP-A-565 165 (A1), JP-A-8-286340, JP-A-8-292529, JP-A-8-297354, JP-A-8-320542, and JP-A-8-292531.

As another method in which a color-developing agent is stably built into a light-sensitive material, a method is conceivable in which a p-phenylenediamine derivative in the stable form of a precursor is built into a light-sensitive material..

The precursor of a p-phenylenediamine derivative that can be built in includes compounds described in U.S. Pat. Nos. 2,507,114, 3,342,597, 4,060,418, JP-A-56-6235, JP-A-56-89735, JP-A-58-192031, JP-A-63-123046, and JP-A-6-347963. These compounds are, however, compounds that release p-phenylenediamine derivatives under alkaline conditions at the time of processing, and such compounds release p-phenylenediamine derivatives gradually, inevitably, in the presence of water or the like even during storage, leading to the same problems as when a p-phenylenediamine derivative itself is added to a light-sensitive material. It is quite difficult not to allow a p-phenylenediamine derivative to be released during storage but to allow it to be released in a short period of time only under alkaline conditions at the time of processing, and it has not yet been attained to secure both satisfactory storage stability and color-forming property at the same time. To deal with these problems, in contrast to these compounds, compounds that can release p-phenylenediamine derivatives using hydrogen peroxide are described in U.S. Pat. No. 5,538,834 and JP-A-5-257226. Indeed, in the case of these compounds, since the release reaction is accelerated with hydrogen peroxide, it is possible to increase the reaction activity at the time of processing, with storage stability retained. Even by means of these compounds, the storage stability was, however, still unsatisfactory, and there is need for development of a technique in which a p-phenylenediamine derivative (a photographically useful compound) is allowed to be contained stably during a long-term storage of the light-sensitive material, and the derivative can be released quickly at the time of processing.

SUMMARY OF THE INVENTION

An object of the present invention is to provide a novel aromatic aldehyde derivative and its precursor.

Another object of the present invention is to provide a photographic light-sensitive material whose processing fluctuation is low and fluctuation of photographic properties by storage is low.

Further object of the present invention is to provide an image-forming method using the light-sensitive material.

Still another object of the present invention is to provide a silver halide color photographic light-sensitive material that can be processed with an activator solution substantially free from any p-phenylenediamine derivative apt to be deteriorated with time, that is stable during its long-term storage, and that can form an image quickly when processed.

Further object of the present invention is to provide an image-forming method using the light-sensitive material.

Other and further objects, features, and advantages of the invention will appear more fully from the following description, taken in connection with the accompanying drawings.

DETAILED DESCRIPTION OF THE INVENTION

Figure 1:
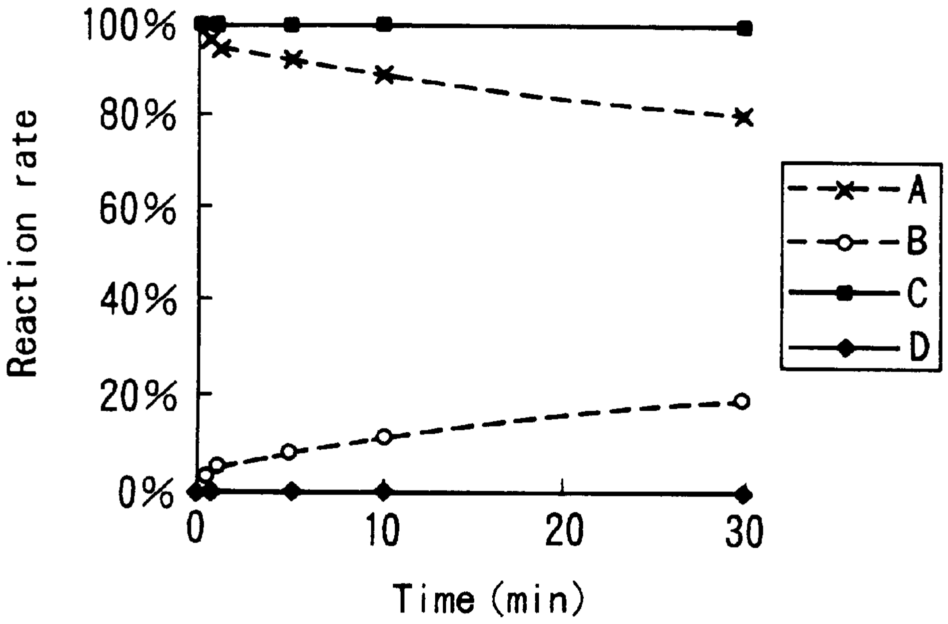
FIG. 1 is a diagram showing the results of the stability in an alkaline solution measured by HPLC using a model compound.

The above objects have been attained by the means shown below. That is, according to the present invention, there are provided:

[1] A silver halide photographic light-sensitive material having at least one light-sensitive silver halide emulsion layer on a base, which comprises a compound represented by the following formula (1) having a photographically useful group protected: formula (1)

$$V—Ar^1—X^1—(L^1)_{m1}—PUG$$

wherein V represents a group that can be converted to a hydroxyl group in the presence of a peroxide in an alkaline solution by a rearrangement reaction, $Ar^1$ represents an aryl group or a heterocyclic group, $X^1$ represents a methylene group substituted at a position that allows a photographically useful group to be released upon subjection of the group represented by V to an oxidation action, $L^1$ represents a linking group, PUG represents a photographically useful group, and m1 is an integer of 0 to 3.

[2] The light-sensitive material, wherein the compound represented by formula (1) having a photographically useful group protected is a compound represented by the following formula (2):

formula (2)

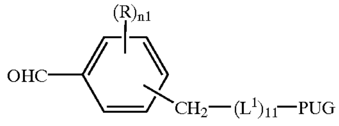

wherein R represents a hydrogen atom, a hydroxyl group, a halogen atom, an alkyl group, a cycloalkyl group, an aryl group, a heterocyclic group, an alkoxy group, an aryloxy group, an acylamino group, a sulfonylamino group, or another amino group; or R's may bond together to form a ring, in some cases; $—CH_2—$ represents a methylene group positioned in the ortho position or the para position with respect to the formyl group; $L^1$ represents a linking group; PUG represents a photographically useful group; 11 is an integer of 0 to 3; n1 is an integer of 1 to 4; and, when n1 is 2 or more, R's are the same or different.

[3] The light-sensitive material, wherein the compound represented by formula (1) having a photographically useful group protected is a compound represented by the following formula (3):

formula (3)

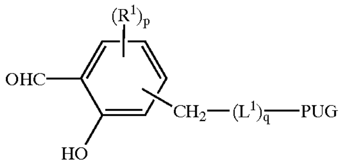

wherein $R^1$ represents a hydrogen atom, a hydroxyl group, a halogen atom, an alkyl group, a cycloalkyl group, an aryl group, a heterocyclic group, an alkoxy group, an aryloxy group, an acylamino group, a sulfonylamino group, or another amino group, or $R^1$'s may bond together to form a ring in some cases; —$CH_2$— represents a methylene group positioned in the ortho position or the para position with respect to the formyl group, $L^1$ represents a linking group, PUG represents a photographically useful group, p is an integer of 1 to 3, q is an integer of 0 to 3; and when p is 2 or more, $R^1$'s are the same or different.

[4] The light-sensitive material, wherein a compound that is released from the compound represented by formula (1) having a photographically useful group protected is a color-developing agent.

[5] An aromatic-aldehyde compound, represented by the following formula (4):

formula (4)

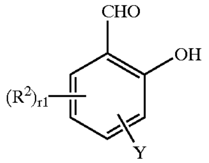

wherein $R^2$ represents a hydroxyl group, a halogen atom, an alkyl group, a cycloalkyl group, an aryl group, a heterocyclic group, an alkoxy group, an aryloxy group, an acylamino group, a sulfonylamino group, an unsubstituted amino group, a monoalkylamino group, a dialkylamino group, an arylamino group, or an alkylarylamino group; or $R^2$'s may bond together to represent a 5- or 6-membered ring, in some cases; Y is positioned in the ortho position or the para position with respect to the formyl group and represents a methylene group substituted by at least one selected from a group consisting of a hydroxyl group, a halogen atom, an alkoxy group, an aryloxy group, an alkylthio group, an arylthio group, an acyloxy group, a chlorocarbonyloxy group, an alkoxycarbonyloxy group, and an aminocarbonyloxy group; r1 is an integer of 0 to 3; and, when r1 is 2 or more, $R^2$'s are the same or different.

[6] The aromatic-aldehyde compound represented by formula (4), which compound is an aromatic-aldehyde compound represented by the following formula (5):

formula (5)

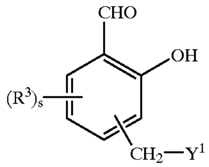

wherein $R^3$ represents a hydroxyl group, an alkyl group, a cycloalkyl group, an aryl group, an alkoxy group, an aryloxy group, an acylamino group, a sulfonylamino group, an unsubstituted amino group, a monoalkylamino group, a dialkylamino group, an arylamino group, or an alkylarylamino group, or $R^3$'s may bond together to represent a 5- or 6-membered ring in some cases; —$CH_2$— is positioned in the ortho position or the para position with respect to the formyl group, $Y^1$ represents an alkylthio group, an arylthio group, a chlorocarbonyloxy group, an alkonxycarbonyloxy group, or an aminocarbonyloxy group, s is an integer of 0 to 3; and when s is 2 or more, $R^3$'s are the same or different.

[7] A compound represented by the following formula (6):

formula (6)

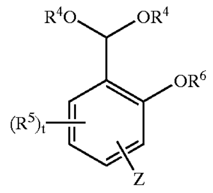

wherein $R^4$ represents an alkyl group, an aryl group, or an acyl group, or $R^4$'s may bond together to represent a 5- or 6-membered ring in some cases; $R^5$ represents a hydroxyl group, a halogen atom, an alkyl group, a cycloalkyl group, an aryl group, a heterocyclic group, an alkoxy group, an aryloxy group, an acylamino group, a sulfonylamino group, an unsubstituted amino group, a monoalkylamino group, a dialkylamino group, an arylamino group, or an alkylarylamino group, or $R^5$'s may bond together to represent a 5- or 6-membered ring in some cases; $R^6$ represents a hydrogen atom, an alkyl group, or an acyl group, Z is positioned in the ortho position or the para position with respect to the $(R^4O)_2CH$ group and represents a methylene group substituted by at least one selected from a group consisting of a hydroxyl group, a halogen atom, an alkoxy group, an aryloxy group, an alkylthio group, an arylthio group, an acyloxy group, an alkoxycarbonyloxy group, and an aminocarbonyloxy group, t is an integer of 0 to 3, and when t is 2 or more, $R^5$'s are the same or different.

[8] The compound represented by formula (6) is a compound represented by the following formula (7):

formula (7)

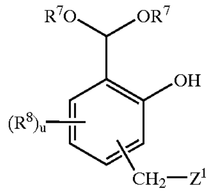

wherein $R^7$ represents an alkyl group or an aryl group, or $R^7$'s may bond together to represent a 5- or 6-membered ring in some cases; $R^8$ represents a hydroxyl group, an alkyl group, an aryl group, an alkoxy group, or an aryloxy group, or $R^8$'s may bond together to represent a 5- or 6-membered ring in some cases; —$CH_2$— is positioned in the ortho position or the para position with respect to the $(R^7O)_2CH$ group, $Z^1$ represents an alkylthio group, an arylthio group, an alkoxycarbonyloxy group, or an aminocarbonyloxy group, u is an integer of 0 to 3, and when u is 2 or more, $R^8$'s are the same or different.

[9] An image-forming method, comprising processing one of the above silver halide photographic light-sensitive materials in the presence of a peroxide.

[10] A silver halide color photographic light-sensitive material having at least three photographic constitutional layers on a base, containing, in any of the said photographic constitutional layers, three kinds of silver halide emulsions different in light-sensitivity, at least three dye-forming couplers, and at least one color-developing agent precursor represented by the following formula (D1):

$$OHC—Ar^2—X^2—(L^2)_{m2}—PPD \qquad \text{formula (D1)}$$

wherein $Ar^2$ represents an aryl group or a heterocyclic group, $X^2$ represents a methylene group substituted at a position that allows a color-developing agent to be released when the formyl group is subjected to an oxidation action, $L^2$ represents a linking group, m2 is an integer of 0 to 3, and PPD represents a group to give a color-developing agent.

[11] The color light-sensitive material, wherein the color-developing agent precursor represented by formula (D1) is one represented by the following formula (D2):

formula (D2)

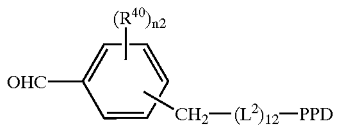

wherein $R^{40}$ represents a hydrogen atom, a hydroxyl group, a halogen atom, an alkyl group, a cycloalkyl group, an aryl group, a heterocyclic group, an alkoxy group, an aryloxy group, an acyloxy group, an acylamino group, a sulfonylamino group, or another amino group; or $R^{40}$'s may bond together to form a ring, in some cases; $—CH_2—$ represents a methylene group positioned at the ortho or para position with respect to the formyl group; $L^2$ represents a linking group; PPD represents a group to give a color-developing agent; 12 is an integer, and n2 is an integer of 1 to 4.

[12] The color light-sensitive material, wherein the color-developing agent precursor represented by formula (D2) is one represented by the following formula (D3):

formula (D3)

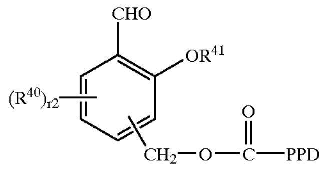

wherein $R^{41}$ represents a hydrogen atom, an alkyl group, an aryl group, or an acyl group; $R^{40}$ has the same meaning as that in formula (D2); $—CH_2—$ represents a methylene group positioned at the ortho or para position with respect to the formyl group; PPD represents a group to give a color-developing agent, and r2 is an integer of 1 to 3.

[13] The color light-sensitive material, wherein any of the said photographic constitutional layers contains an auxiliary developing agent and/or its precursor.

[14] A color image-forming method, comprising processing one of the said silver halide color photographic light-sensitive materials with an activator solution that is substantially free from any color-developing agent, but that contains a peroxide.

[15] The color image-forming method, wherein the exposure of the light-sensitive material is carried out by using scanning exposure, with the exposure time per picture element being $10^{-8}$ to $10^{-4}$ sec and adjacent rasters being overlapped.

Herein, in the present invention, a group on a compound includes both a group having a substituent thereon and a group having no substituent (i.e. an unsubstituted group), unless otherwise specified.

Herein, in this specification and the claims, by the term "a photographically useful compound" is meant a compound that can be used in photographic materials so as to obtain a certain result or a special effect, and specifically meant is, for example, a coupler, a color-developing agent, an auxiliary developing agent, a redox compound, a dye, a development inhibitor, a development accelerator, a stabilizer, an antioxidant, a bleach accelerator, or a fixing agent.

Hereinbelow, the constitution of the present invention is specifically described in detail.

Now, the compound represented by formula (1) is described in detail.

In formula (1), V represents a group that can react with a peroxide in an alkaline solution, to be converted to a hydroxyl group via a rearrangement reaction, and specific examples include a formyl group, a substituted or unsubstituted acyl group (e.g., acetyl, benzoyl, and trifluoroacetyl), whose substituent includes the substituents to be enumerated with respect to the substituent on the $Ar^1$ group described later. V is preferably a formyl group.

In formula (1), the $Ar^1$ group is a substituted or unsubstituted aryl group or a substituted or unsubstituted heterocyclic group. As the aryl group, preferably those having 6 to 30 carbon atoms and specifically a phenyl group, a naphthyl group, and the like, can be mentioned. Further, as the heterocyclic group, preferably those that are 3- to 8-membered and have at least one oxygen atom, nitrogen atom, or sulfur atom as the hetero atom in the atoms constituting the ring, can be mentioned. The heterocyclic group may form a condensed ring with another aromatic ring, and specifically a 2-pyridyl group, a 2-furyl group, a 2-benzoxazolyl group, a 2-thienyl group, and the like can be mentioned. As $Ar^1$, an aryl group is particularly preferable.

In formula (1), when the $Ar^1$ group may have a substituent, specific examples of the substituent include a straight-chain or branched alkyl group having 1 to 60 carbon atoms (e.g., methyl, ethyl, propyl, isopropyl, t-butyl, 2-ethylhexyl, nonyl, undecyl, pentadecyl, n-hexadecyl, and 3-decaneamidopropyl), a cycloalkyl group having 3 to 60 carbon atoms (e.g., cyclopropyl, 1-ethylcyclopropyl, cyclopentyl, and cyclohexyl), an aryl group having 6 to 30 carbon atoms (e.g., phenyl and naphthyl), a heterocyclic group having 2 to 60 carbon atoms (a 3- to 8-membered monocyclic ring or condensed ring which has at least one oxygen atom, nitrogen atom, or sulfur atom as the hetero atom, e.g., 2-pyridyl, 2-furyl, 2-benzoxazolyl, and 2-thienyl), an acylamino group having 2 to 60 carbon atoms (e.g., acetylamino, n-butanoylamino, octanoylamino, 2-hexadecanoylamino, 2-(2',4'-di-t-amylphenoxy) butanoylamino, benzoylamino, and nicotinoylamino), another amino group having 0 to 60 carbon atoms (e.g., an unsubstituted amino group, a monoalkylamino group, a dialkylamino group, an arylamino group, and an alkylarylamino group, and specifically unsubstituted amino, diethylamino, n-octylamino, 3-(2',4'-di-t-amylphenoxy) propylamino, and morpholino), an alkoxy group having 1 to 60 carbon atoms (e.g., methoxy, ethoxy, butoxy, n-octyloxy, hexadecyloxy, and 2-methoxyethoxy), an aryloxy group having 6 to 60 carbon atoms (e.g., phenoxy, 2,4-t-amylphenoxy, 4-t-butylphenoxy, and naphthoxy), an alkylthio group having 1 to 60 carbon atoms (e.g, methylthio, ethylthio, butylthio, and hexadecylthio), an arylthio group having 6 to 60 carbon atoms (e.g., phenylthio and 4-dodecyloxyphenylthio), an acyl group having 1 to 60 carbon atoms (e.g., acetyl, benzoyl, butanoyl, and decanoyl), an acyloxy group having 6 to 60 carbon atoms (e.g., benzoyloxy, octanoyloxy, 2-hexadecanoyloxy, and 2-(2',4'-di-t-amylphenoxy)butanoyloxy), a sulfonyl group having 1 to 60 carbon atoms (e.g., methanesulfonyl, butanesulfonyl, and toluenesulfonyl), a sulfonylamino group having 1 to 60 carbon atoms (e.g., methanesulfonylamino and phenylsulfonylamino), a cyano group, an alkoxycarbonyl group having 2 to 60 carbon atoms (e.g., ethoxycarbonyl, hexyloxycarbonyl, and dodecyloxycarbonyl), an aryloxycarbonyl group having 7 to 30 carbon atoms (e.g., phenoxycarbonyl and naphthyloxycarbonyl), a carbamoyl group having 1 to 60 carbon atoms (e.g., N,N-dicyclohexylcarbamoyl), a sulfamoyl group having 0 to 60 carbon atoms (e.g., N,N-dimethylsulfamoyl), a carboxyl group, a halogen atom (e.g., fluorine, chlorine, and bromine), and a hydroxyl group.

Among these substituents, preferable ones are an alkyl group, a cycloalkyl group, an alkoxy group, an aryloxy group, an acylamino group, a sulfonylamino group, and a hydroxyl group, more preferable ones are an alkoxy group, an acylamino group, a sulfonylamino group, and a hydroxyl group, and particularly preferable ones are an alkoxy group and a hydroxy group.

If possible, these substituents may bond together to form a ring, such as a cyclopentene ring, a cyclohexane ring, a norbornene ring and a dihydrofuran ring.

Further, if possible, these substituents may have further a substituent, and the substituent includes those enumerated as a substituent on the above $Ar^1$ group, and it is preferably an alkyl group, an alkoxy group, an aryloxy group, an acyl group, an alkoxycarbonyl group, an aryloxycarbonyl group, a carbamoyl group, a sulfonyl group, a sulfamoyl group, a cyano group, a carboxyl group, or a hydroxyl group, and particularly preferably an alkyl group, an alkoxy group, a hydroxyl group, or a carboxyl group.

Preferably at least one of substituents on the $Ar^1$ group has a ballasting group built therein, which ballasting group is usually used in a nondiffusing photographic additive, such as a coupler. The ballasting group is a photographically inactive group having more than 7 carbon atoms, and it can be chosen, for example, from an alkyl group, an alkoxy group, an aryl group, an aryloxy group, an amido group, a ureido group, a sulfonamido group, an ester group, a sulfonyl group, an acyl group, and the like, or a combination of these, or a combination thereof with a hydroxyl group or the like.

In formula (1), $X^1$ is a substituted or unsubstituted methylene group, and the substituent thereof includes those on the $Ar^1$ group described above. $X^1$ is preferably an unsubstituted methylene group.

In formula (1), with respect to the position where $X^1$ is bonded to $Ar^1$, when the $Ar^1$ group is an aryl ring and the group represented by V is a formyl group, the position is the ortho position or the para position with respect to the formyl group; while when the $Ar^1$ group is a heterocyclic ring, the position is the 2-position or the 4-position, with it being assumed that the position of the formyl group is the 1-position; and the positional relationship of $X^1$ on the $Ar^1$ group is such that, after the formyl group is converted to a hydroxyl group, the photographically useful group (PUG) may be released by electron transfer.

In formula (1), $L^1$ represents a linking group, examples of which include a known timing group, such as a

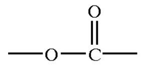

group described in DE-A-2 803 145. In this group, the (—O) atom bonds to the released compound (OHC—$Ar^1$—$X^1$), and the carbon atom bonds to the hetero atom in the photographically useful group (PUG), to link the released compound with the photographically useful group. Also, there can be mentioned, for example, a group as described in DE-A-2 855 697, that, when released from the compound of formula (1) whose photographically useful group is protected, undergoes an intramolecular nucleophilic reaction, to release the photographically useful group; and a group as described in DE-A-3 105 026, that, after being released from the compound of formula (1) whose photographically useful group is protected, allows electron transfer along the conjugated system, thereby leading to the release of the photographically useful group.

Further, $L^1$ may be such a group that, when it is released from the compound of formula (1), it itself takes part in a coupling reaction or a redox reaction, and as a result of the reaction, the PUG (e.g. PPD) can be released imagewise by the coupling reaction with the nucleophilic agent released imagewise or the imagewise redox reaction with a silver halide.

m1 is an integer of 0 to 3, with preference given to 1 or 2.

In formula (1), PUG represents a photographically useful group, and it is, for example, a halide ion (e.g., a chloride ion, a bromide ion, and an iodide ion) or a group to give a compound selected from a coupler, a developing agent, an auxiliary developing agent, a redox compound, a dye, a development inhibitor, a development accelerator, a stabilizer, an antioxidant, a bleach accelerator, and a fixing agent. In formula (1), PUG is particularly preferably a group to give a color-developing agent.

Among the compounds represented by formula (1), preferable compounds are those represented by formula (2).

In formula (2), R represents a hydrogen atom, a hydroxyl group, a halogen atom, an alkyl group, a cycloalkyl group, an aryl group, a heterocyclic group, an alkoxy group, an aryloxy group, an acylamino group, a sulfoynylamino group, or another amino group, and R's may bond together to form a ring in some cases. Specific examples of these groups are the same as the substituents on the $Ar^1$ group in formula (1). —$CH_2$— represents a methylene group positioned in the ortho or para position with respect to the formyl group, $L^1$ represents a linking group, and PUG represents a photographically useful group.

11 is an integer of 0 to 3, and n1 is an integer of 1 to 4. When n1 is 2 or more, R's are the same or different.

In formula (2), preferably R represents a hydroxyl group, an alkyl group, an aryl group, an alkoxy group, an aryloxy group, an acylamino group, a sulfonylamino group, or another amino group, more preferably a hydroxyl group, an alkyl group, an alkoxy group, an acylamino group, or another amino group, and particularly preferably a hydroxyl group, an alkoxy group, or another amino group.

11 is preferably 0 or 1, and n1 is preferably 1 or 2.

Further, if possible, R may further be substituted and the substituent is preferably an alkyl group, an alkoxy group, an aryloxy group, an alkoxycarbonyl group, an aryloxycarbonyl group, a carbamoyl group, a sulfamoyl group, a cyano group, a carboxyl group, or a hydroxyl group, and particularly preferably an alkyl group, an alkoxy group, an hydroxyl group, or a carboxyl group. Specific examples of these groups are the same as those described for the substituent on the $Ar^1$ group in formula (1).

Among the compounds represented by formula (2), more preferable compounds are those represented by formula (3).

In formula (3), $R^1$ represents a hydrogen atom, a hydroxyl group, a halogen atom, an alkyl group, a cycloalkyl group, an aryl group, a heterocyclic group, an alkoxy group, an aryloxy group, an acylamino group, a sulfoynylamino group, or another amino group, and $R^1$'s may bond together to form a ring in some cases. Specific examples of these groups are the same as the substituents on the $Ar^1$ group in formula (1). —$CH_2$— represents a methylene group positioned in the ortho or para position with respect to the formyl group, $L^1$ represents a linking group, and PUG represents a photographically useful group.

p is an integer of 1 to 3, and q is an integer of 0 to 3. When p is 2 or more, $R^1$'s are the same or different. Preferably $R^1$ is an alkoxy group. Preferably p is 0 or 1, and q is 1 or 2.

Further, if possible, $R^1$ may further be substituted, and the substituent is preferably an alkyl group, an alkoxy group, an aryloxy group, an alkoxycarbonyl group, an aryloxycarbonyl group, a carbamoyl group, a sulfamoyl group, a cyano group, a carboxyl group, or a hydroxyl group, and particularly preferably an alkyl group, an alkoxy group, an hydroxyl group, or a carboxyl group. Specific examples of these groups are the same as those described for the substituent on the $Ar^1$ group in formula (1).

The specific example of compounds included in formula (1) for use in the present invention are shown below, but the present invention is not limited to them.

(1)

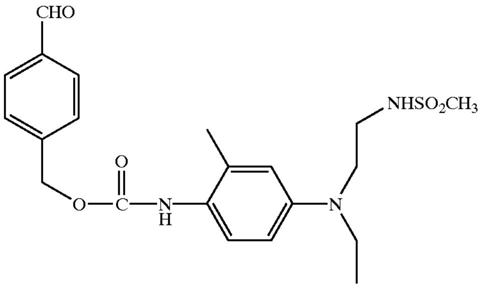

(2)

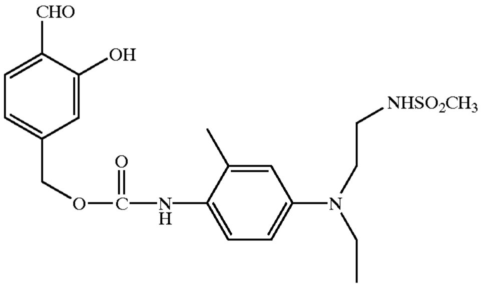

(3)

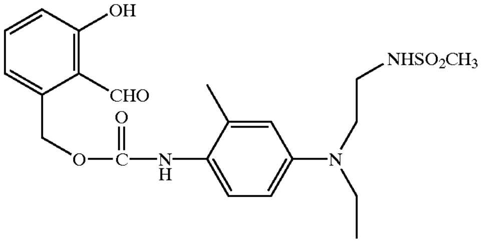

-continued (4)

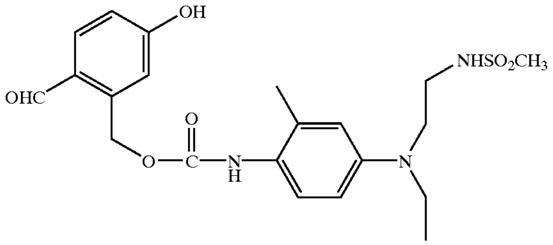

(5)

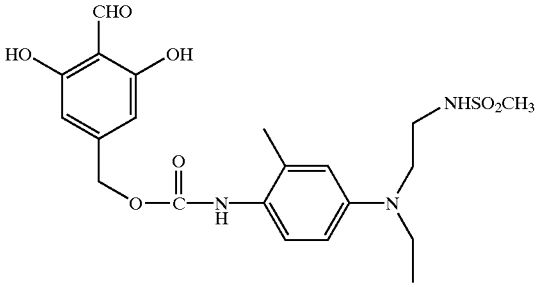

(6)

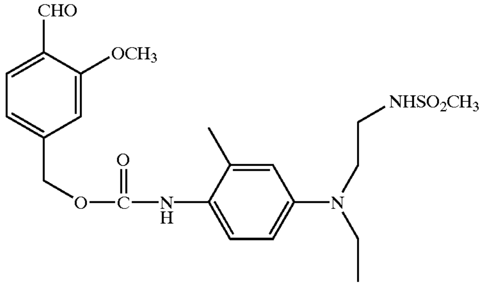

(7)

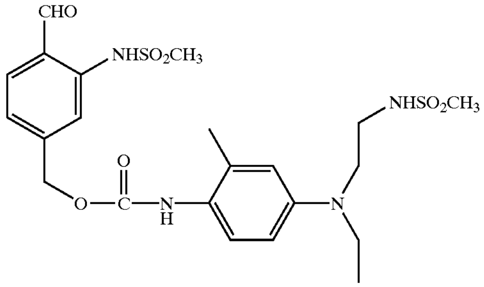

(8)

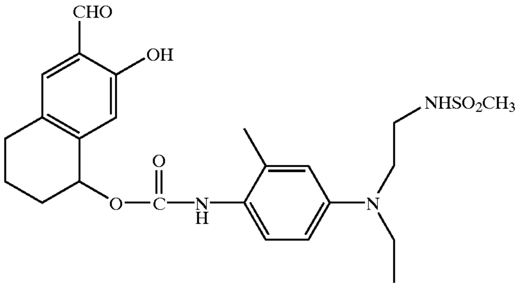

-continued
(9)
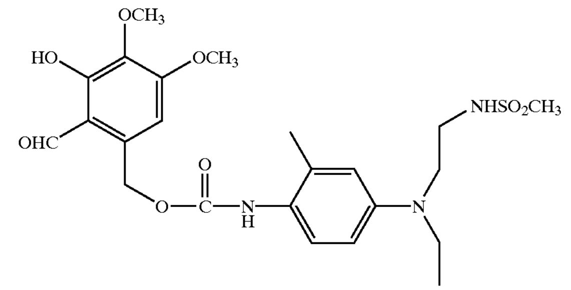
(10)
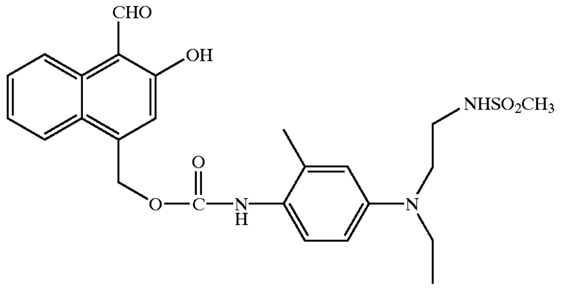
(11)
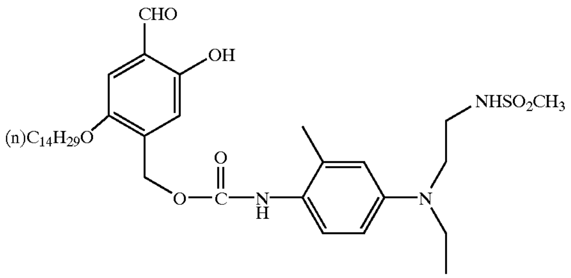
(12)
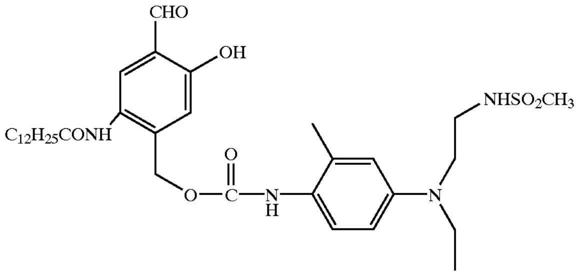
(13)
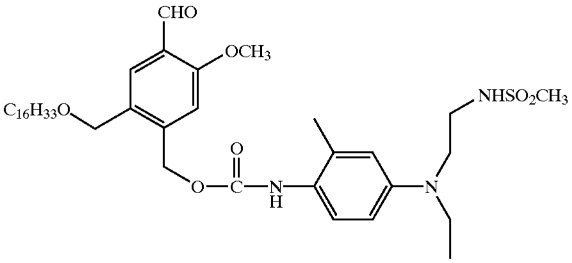
-continued
(14)
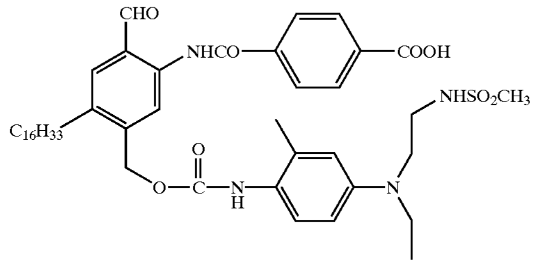
(15)
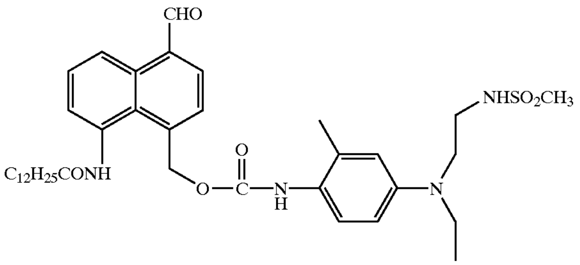
(16)
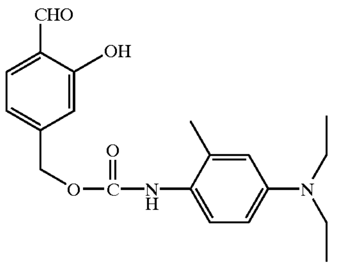
(17)
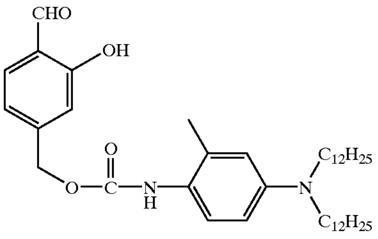
(18)
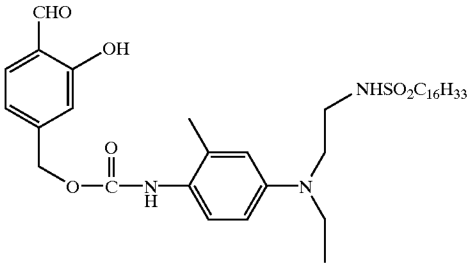

-continued (19)

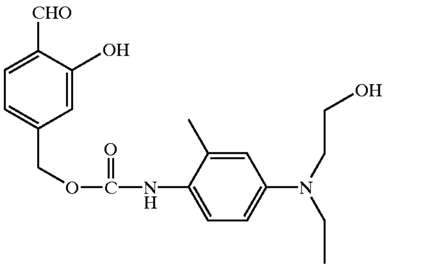

(20)

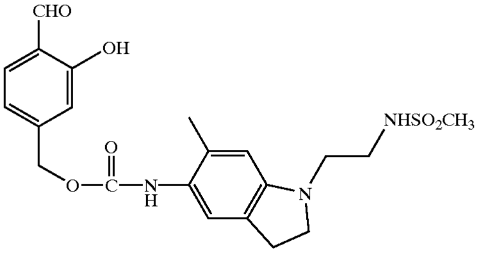

(21)

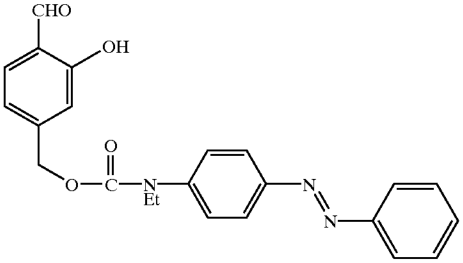

(22)

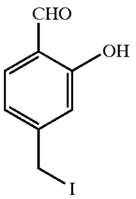

-continued (23)

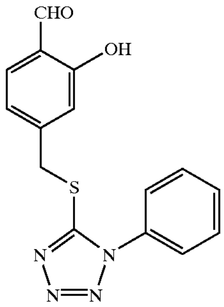

(24)

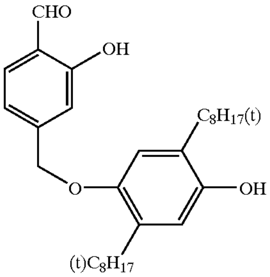

(25)

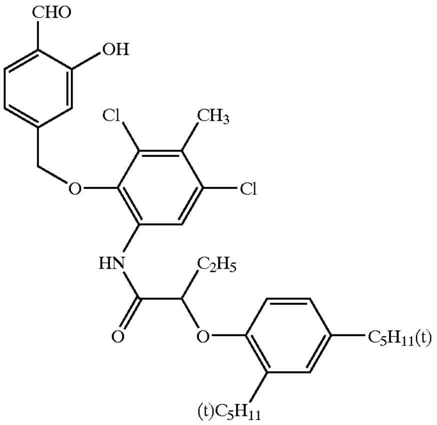

These compounds can be synthesized by the methods described below or those according to them. A typical Synthetic Example of the compound for use in the present invention is shown. The PUG component (PPD in the exemplified compound (1)) in the structural formula of the above (1) is 4-amino-3-methyl-N-ethyl-N-β-(methanesulfonamidoethyl)aniline, and the abbreviation of the methyl group and the ethyl group in other structural formulae is made similarly.

Exemplified Compound (2) was synthesized as follows:

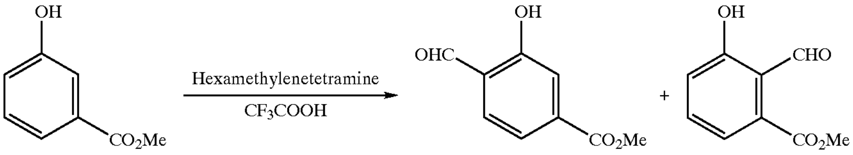

A

B

-continued

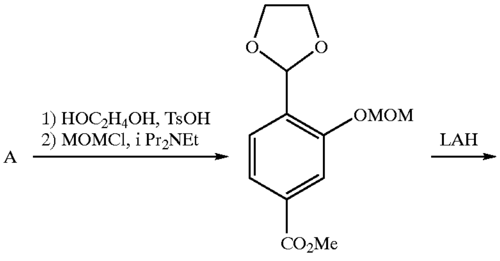

C

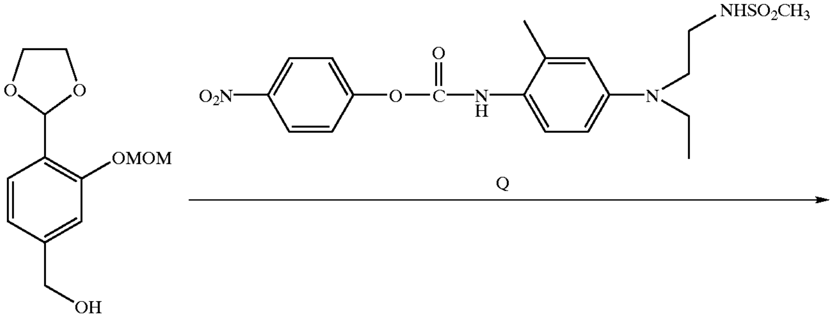

D

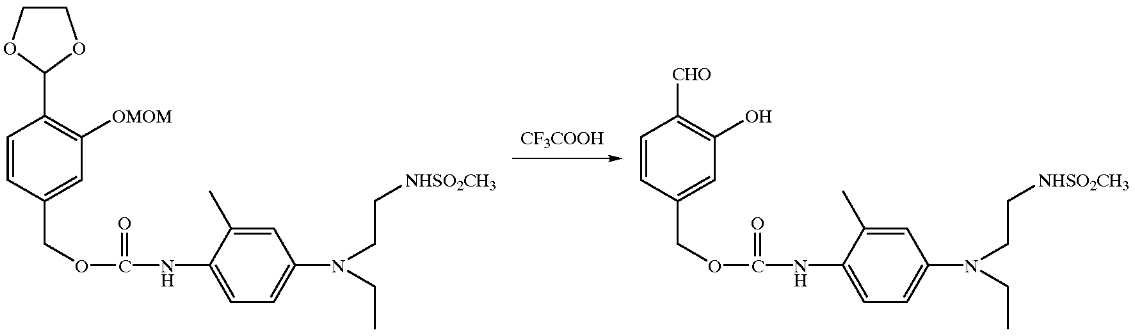

E (2)

Compound (A): 11.3 g of hexamethylenetetramine was added to 50 ml of a solution of methyl 3-hydroxybenzoate in trifluoroacetic acid, followed by stirring at 80° C. for 3 hours. The reaction liquid was added to 100 ml of water, and extraction with ethyl acetate was carried out in a usual manner. The extract liquid was concentrated, and the residue was purified by silica gel column chromatography (n-hexane/ethyl acetate), to obtain Compound (A) and Compound (B) (in an amount of 62.8 g; yield: 78%).

Compound (C): 1.9 g of ethylene glycol and 0.2 g of paratoluenesulfonic acid monohydrate were added to 50 ml of a solution of Compound (A) in toluene, and they were heated for 3 hours under reflux, with the water being removed. One hundred ml of water was added to the reaction liquid, and extraction with ethyl acetate was carried out in a usual manner.

The extract liquid was concentrated, to obtain a crude purified product. To 20 ml of a solution of this crude product in methylene chloride, were added 2.4 g of chloromethyl methyl ether and 5.2 g of diisopropylethylamine, followed by stirring for 3 hours at room temperature. Fifty ml of water was added to the reaction liquid, and extraction with ethyl acetate was carried out in a usual manner. The extract liquid was concentrated, and the residue was purified by silica gel column chromatography (n-hexane/ethyl acetate), to obtain Compound (C) (in an amount of 5.1 g; yield: 84%).

Compound (D): 0.7 g of lithium aluminum hydride was added to 50 ml of a solution containing 5.0 g of Compound (C) in THF, followed by stirring for 3 hours at room temperature. The reaction liquid was cooled with ice; then 1 ml of methanol, 1 ml of water, and 2 ml of a 10% aqueous sodium hydroxide solution were added to it, and extraction with ethyl acetate was carried out in a usual manner. The extract liquid was concentrated, and the residue was purified by silica gel column chromatography (n-hexane/ethyl acetate), to obtain Compound (D) (in an amount of 3.5 g; yield: 78%).

Compound (E): 5.8 g of Compound (Q) and 2 ml of triethylamine were added to 40 ml of a solution containing 3.2 g of Compound (D) in acetonitrile, followed by stirring at 60° C. for 3 hours. One hundred ml of water was added to the reaction liquid, and extraction with ethyl acetate was carried out in a usual manner. The extract liquid was concentrated, and the residue was purified by silica gel column chromatography (n-hexane/ethyl acetate), to obtain Compound (E) (in an amount of 6.5 g; yield: 92%).

Compound (2): 10 ml of trifluoroacetic acid was added to 50 ml of a solution containing 5 g of Compound (E) in methylene chloride, followed by stirring at room temperature for 3 hours. After the reaction liquid was neutralized with a saturated sodium bicarbonate solution, extraction with ethyl acetate was carried out in a usual manner. The extract liquid was concentrated, and the residue was purified by silica gel column chromatography (n-hexane/ethyl acetate), to obtain Compound (2) (in an amount of 2.6 g; yield: 63%).

The compound represented by formula (1) includes the aromatic-aldehyde-derivative compound represented by formula (4) that is a novel compound. The aromatic-aldehyde-derivative compound of the present invention represented by formula (4) is also useful as a synthetic intermediate compound for medicines, agricultural chemicals, materials for electronics, and the like. The manner of protection in the aromatic-aldehyde-derivative compound of the present invention can be used not only to protect a photographically useful group but also to be a protection group in general organic synthesis.

Hereinbelow, the compound represented by formula (4) is described.

The group represented by $R^2$ in formula (4) includes a hydroxyl group, a halogen atom, an alkyl group, a cycloalkyl group, an aryl group, a heterocyclic group, an alkoxy group, an aryloxy group, an acylamino group, a sulfonylamino group, an unsubstituted amino group, a monoalkylamino group, a dialkylamino group, an arylamino group, and an alkylarylamino group, specific examples of these groups are the same as those described for the substituent on the $Ar^1$ group in formula (1), and $R^2$'s may bond together to form a 5- or 6-membered ring in some cases, such as a cyclopentene ring and a cyclohexane ring.

Further, if possible, $R^2$ may further be substituted, and the substituent is preferably an alkyl group, an alkoxy group, an aryloxy group, an acyl group, an alkoxycarbonyl group, an aryloxycarbonyl group, a carbamoyl group, a sulfonyl group, a sulfamoyl group, a cyano group, a carboxyl group, or a hydroxyl group, and particularly preferably an alkyl group, an alkoxy group, an hydroxyl group, or a carboxyl group. Specific examples of these groups are the same as those described for the substituent on the $Ar^1$ group in formula (1).

Y represents a substituted methylene group that is positioned in the ortho or para position with respect to the formyl group.

In formula (4), examples of the substituent on the substituted methylene group represented by Y include a hydroxyl group, a halogen atom (e.g., fluorine, chlorine, and bromine), an alkoxy group (e.g., methoxy, ethoxy, butoxy, n-octyloxy, hexadecyloxy, and 2-methoxyethoxy), an aryloxy group (e.g., phenoxy, 2,4-t-amylphenoxy, 4-t-butylphenoxy, and naphthoxy), an alkylthio group (e.g., methylthio, ethylthio, butylthio, and hexadecylthio), an arylthio group (e.g., phenylthio and 4-methylphenylthio), an acyloxy group (e.g., acetoxy and benzoyloxy), a chlorocarbonyloxy group, an alkoxycarbonyloxy (e.g., methoxycarbonyloxy and phenoxycarbonyloxy), or an aminocarbonyloxy group (specifically an N,N-diethylaminocarbonyloxy group and an N-(4-octylphenyl)aminocarbonyloxy group), with preference given to an alkylthio group, an arylthio group, an aryloxy group, an alkoxycarbonyloxy group, and an aminocarbonyloxy group.

In formula (4), the substituted methylene group represented by Y is a methylene group substituted with PUG in formula (1), or a methylene group substituted with a group capable becoming PUG by modifying it. This is similarly applied to the following: the group $—CH_2—Y^1$ in formula (5), the group Z in formula (6), and the group $—CH_2—Z^1$ in formula (7). That is, the substituent on the substituted methylene group Y or Z, or the substituent $Y^1$ or $Z^1$ is the PUG itself, or a group capable becoming PUG by subjecting modification.

r1 is an integer of 0 to 3, and when r1 is 2 or more, $R^2$'s are the same or different.

Further, the compound represented by the following formula (5) that is a synthetic intermediate of the compound included in formula (4) of the present invention is also a novel compound.

In the compound represented by formula (5), $R^3$ is a hydroxyl group, an alkyl group, a cycloalkyl group, an aryl group, an alkoxy group, an aryloxy group, an acylamino group, a sulfonylamino group, an unsubstituted amino group, a monoalkylamino group, a dialkylamino group, an arylamino group, and an alkylarylamino group, specific examples of these groups are the same as those described for the substituent on the $Ar^1$ group in formula (1), and $R^3$'s may bond together to form a 5- or 6-membered ring in some cases, such as a cyclopentene ring and a cyclohexane ring.

Further, if possible, $R^3$ may further be substituted, and the substituent is preferably an alkyl group, an alkoxy group, an aryloxy group, an alkoxycarbonyl group, an aryloxycarbonyl group, a carbamoyl group, a sulfamoyl group, a cyano group, a carboxyl group, or a hydroxyl group, and particularly preferably an alkyl group, an alkoxy group, a hydroxyl group, or a carboxyl group. Specific examples of these groups are the same as those described for the substituent on the $Ar^1$ group in formula (1).

$—CH_2—$ is positioned in the ortho or para position with respect to the formyl group, and $Y^1$ represents an alkylthio group, an arylthio group, a chlorocarbonyloxy group, an alkoxycarbonyloxy group, an aminocarbonyloxy group, or the like. Specific examples of these substituents are the same as those described for the substituent on the substituted methylene group represented by Y in formula (4). s is an integer of 0 to 3, and when s is 2 or more, $R^3$'s are the same or different.

Specific examples of the compound included in formula (4) of the present invention are shown below, but the present invention is not limited to them.

(26)

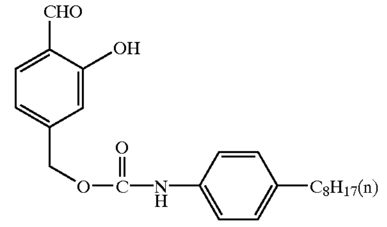

(27)

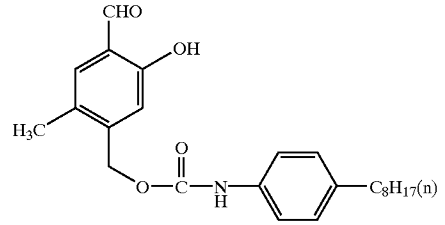

(28)

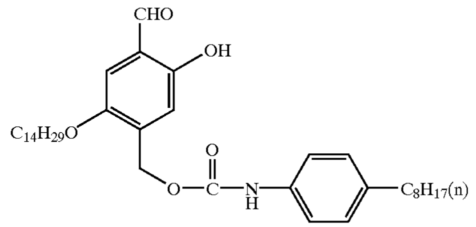

-continued
(29)
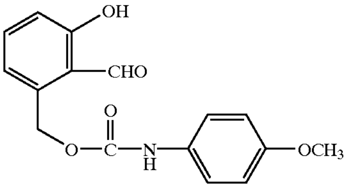
(30)
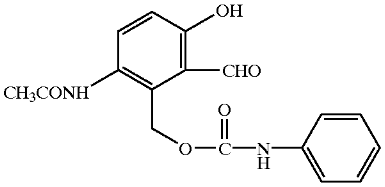
(31)
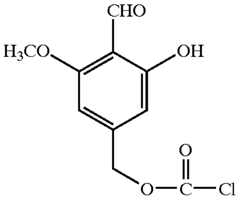
(32)
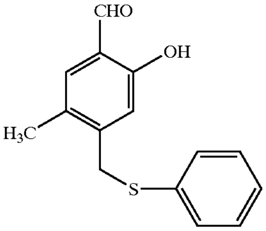
(33)
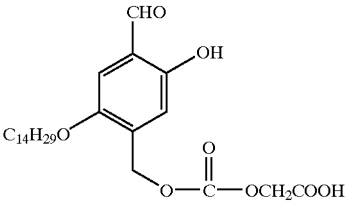
(34)
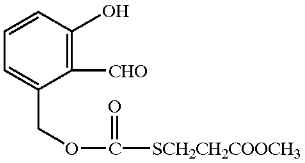
(35)
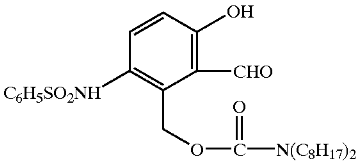
(36)
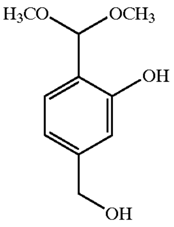
-continued
(37)
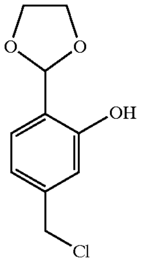
(38)
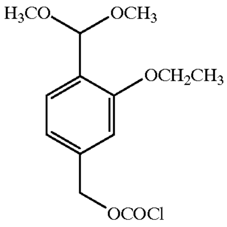
(39)
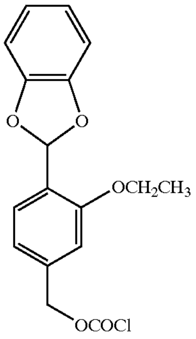
(40)
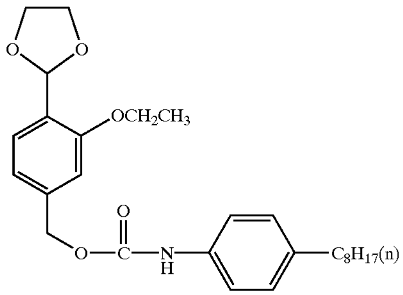
(41)
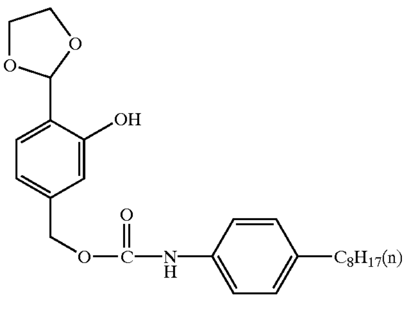

-continued (42)

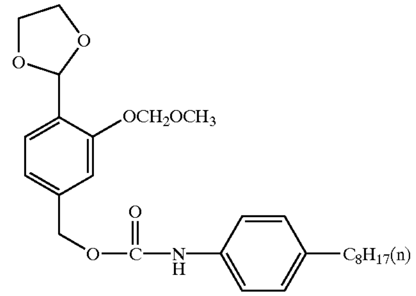

(43)

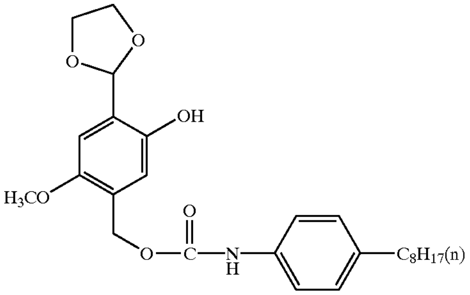

(44)

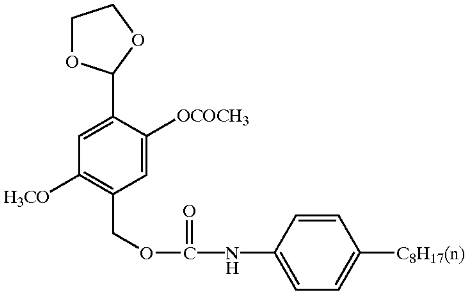

(45)

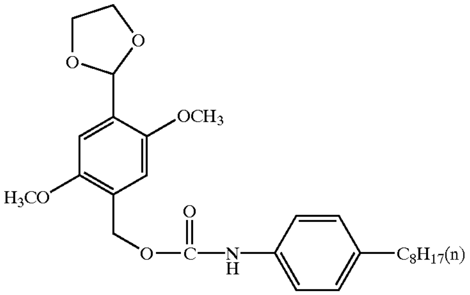

The following are NMR data of compounds (26) to (35) shown above.

| $^1$HNMR($CDCl_3$)δppm | |
|---|---|
| (26) | |
| δ 0.9 | (t, 3H) |
| δ 1.3 to 1.8 | (m, 12H) |
| δ 2.6 | (t, 2H) |
| δ 5.2 | (s, 2H) |
| δ 6.8 | (s, 1H) |
| δ 7.0 to 7.5 | (m, 7H) |
| δ 9.9 | (s, 1H) |

-continued

| $^1$HNMR($CDCl_3$)δppm | |
|---|---|
| δ 11.0 | (s, 1H) |
| (27) | |
| δ 0.9 | (t, 3H) |
| δ 1.3 to 1.8 | (m, 12H) |
| δ 2.6 | (t, 2H) |
| δ 2.3 | (s, 3H) |
| δ 5.1 | (s, 2H) |
| δ 6.5 | (s, 1H) |
| δ 7.0 to 7.5 | (m, 6H) |
| δ 9.8 | (s, 1H) |
| δ 11.2 | (s, 1H) |
| (28) | |
| δ 0.9 | (t, 3H) |
| δ 1.0 | (t, 3H) |
| δ 1.4 to 2.0 | (m, 36H) |
| δ 2.6 | (t, 2H) |
| δ 3.7 | (t, 2H) |
| δ 5.2 | (s, 2H) |
| δ 6.8 | (s, 1H) |
| δ 7.0 to 7.5 | (m, 6H) |
| δ 9.5 | (s, 1H) |
| δ 10.9 | (s, 1H) |
| (29) | |
| δ 0.9 | (t, 3H) |
| δ 1.2 to 1.7 | (m, 12H) |
| δ 2.6 | (t, 3H) |
| δ 5.4 | (s, 2H) |
| δ 6.7 | (s, 1H) |
| δ 7.0 to 7.6 | (m, 7H) |
| δ 10.3 | (s, 1H) |
| δ 11.8 | (s, 1H) |
| (30) | |
| δ 2.7 | (t, 3H) |
| δ 5.3 | (s, 2H) |
| δ 6.8 | (s, 2H) |
| δ 7.0 to 7.8 | (m, 7H) |
| δ 9.5 | (s, 1H) |
| δ 10.8 | (s, 1H) |
| (31) | |
| δ 3.8 | (S, 3H) |
| δ 5.8 | (s, 2H) |
| δ 7.1 | (s, 1H) |
| δ 7.3 | (s, 1H) |
| δ 9.2 | (s, 1H) |
| δ 11.0 | (S, 1H) |
| (32) | |
| δ 2.3 | (s, 3H) |
| δ 4.5 | (s, 2H) |
| δ 7.0 to 7.6 | (m, 7H) |
| δ 9.7 | (s, 1H) |
| δ 10.9 | (s, 1H) |
| (33) | |
| δ 0.9 | (t, 3H) |
| δ 1.4 to 2.0 | (m, 24H) |
| δ 5.0 | (s, 2H) |
| δ 5.3 | (s, 2H) |
| δ 7.1 | (s, 1H) |
| δ 7.3 | (s, 1H) |
| δ 9.5 | (s, 1H) |
| δ 10.9 | (s, 1H) |
| (34) | |
| δ 2.3 | (t, 3H) |
| δ 2.6 | (t, 3H) |
| δ 3.8 | (s, 3H) |
| δ 5.0 | (s, 2H) |
| δ 7.0 to 7.8 | (m, 3H) |
| δ 10.5 | (s, 1H) |
| δ 11.8 | (s, 1H) |

-continued

| $^1HNMR(CDCl_3)\delta ppm$ | |
|---|---|
| (35) | |
| δ 0.9 | (t, 6H) |
| δ 1.0 to 1.8 | (m, 24H) |
| δ 3.5 | (t, 4H) |
| δ 5.3 | (s, 2H) |
| δ 7.0 to 7.8 | (m, 7H) |
| δ 8.1 | (s, 1H) |
| δ 10.0 | (s, 1H) |
| δ 11.5 | (s, 1H) |

The compound represented by formula (1) includes the aromatic-aldehyde-derivative compound represented by formula (6) that is a novel compound. The aromatic-aldehyde-derivative compound of the present invention represented by formula (6) is also useful as a synthetic intermediate compound for medicines, agricultural chemicals, materials for electronics, and the like. The manner of protection in the aromatic-aldehyde-derivative compound of the present invention can be used not only to protect a photographically useful group but also to be a protection group in general organic synthesis.

Hereinbelow, the compound represented by formula (6) is described.

In the compound represented by formula (6), $R^4$ represents an alkyl group, an aryl group, or an acyl group, specific examples of these groups are the same as those described for the substituent on the $Ar^1$ group in formula (1), and $R^4$'s may bond together to form a 5- or 6-membered ring, such as a dioxane ring or a dioxolane ring, in some cases.

$R^5$ represents a hydroxyl group, a halogen atom, an alkyl group, a cycloalkyl group, an aryl group, a heterocyclic group, an alkoxy group, an aryloxy group, an acylamino group, a sulfonylamino group, an unsubstituted amino group, a monoalkylamino group, a dialkylamino group, an arylamino group, and an alkylarylamino group, specific examples of these groups are the same as those described for the substituent on the $Ar^1$ group in formula (1), and $R^5$'s may bond together to form a 5- or 6-membered ring in some cases, such as a cyclopentene ring and a cyclohexane ring.

Further, if possible, $R^5$ may further be substituted, and the substituent is preferably an alkyl group, an alkoxy group, an aryloxy group, an acyl group, an alkoxycarbonyl group, an aryloxycarbonyl group, a carbamoyl group, a sulfonyl group, a sulfamoyl group, a cyano group, a carboxyl group, or a hydroxyl group, and particularly preferably an alkyl group, an alkoxy group, an hydroxyl group, or a carboxyl group. Specific examples of these groups are the same as those described for the substituent on the $Ar^1$ group in formula (1).

$R^6$ represents a hydrogen atom, an alkyl group, or an acyl group, and specific examples of these groups are the same as those described for the substituent on the $Ar^1$ group in formula (1).

Z is positioned in the ortho or para position with respect to the $(R^4O)_2CH$ group, and it represents a methylene group substituted by at least one selected from the group consisting of a hydroxyl group, a halogen atom, an alkoxy group, an aryloxy group, an alkylthio group, an arylthio group, an acyloxy group, an alkoxycarbonyloxy group, and an aminocarbonyloxy group. Specific examples of these substituents are the same as those described for the substituent on the substituted methylene group represented by Y in formula (4).

t is an integer of 0 to 3, and when t is 2 or more, $R^5$'s are the same or different.

Among compounds represented by formula (6), preferable compounds are those represented by formula (7).

In the compound represented by formula (7), $R^7$ represents an alkyl group or an aryl group, specific examples of these groups are the same as those described for the substituent on the $Ar^1$ group in formula (1), and $R^7$'s may bond together to form a 5- or 6-membered ring in some cases, such as a dioxane ring and a dioxolane ring.

$R^8$ represents a hydroxyl group, an alkyl group, an aryl group, an alkoxy group, or an aryloxy group, specific examples of these groups are the same as those described for the substituent on the $Ar^1$ group in formula (1), and $R^8$'s may bond together to form a 5- or 6-membered ring in some cases, such as a cyclopentene ring and a cyclohexane ring.

Further, if possible, $R^8$ may further be substituted, and the substituent is preferably an alkyl group, an alkoxy group, an aryloxy group, an acyl group, an alkoxycarbonyl group, an aryloxycarbonyl group, a carbamoyl group, a sulfonyl group, a sulfamoyl group, a cyano group, a carboxyl group, or a hydroxyl group, and particularly preferably an alkyl group, an alkoxy group, a hydroxyl group, or a carboxyl group. Specific examples of these groups are the same as those described for the substituent on the $Ar^1$ group in formula (1).

—$CH_2$— is positioned in the ortho or para position with respect to the $(R^7O)_2CH$ group, $Z^1$ represents an alkylthio group, an arylthio group, an alkoxycarbonyloxy group, or an aminocarbonyloxy group. Specific examples of these substituents are the same as those described for the substituent on the substituted methylene group represented by Y in formula (4).

u is an integer of 0 to 3, and when u is 2 or more, $R^8$'s are the same or different.

Specific examples of the compound included in formula (6) of the present invention are shown below, but the present invention is not limited to them.

(36)

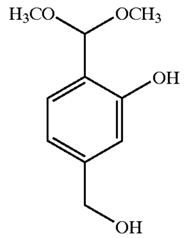

(37)

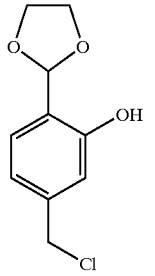

-continued
(38)
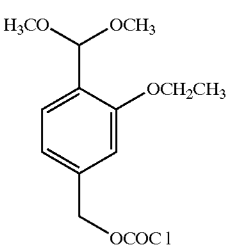
(39)
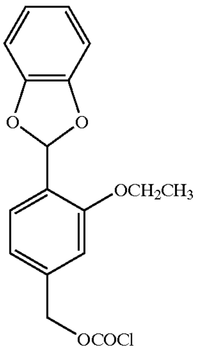
(40)
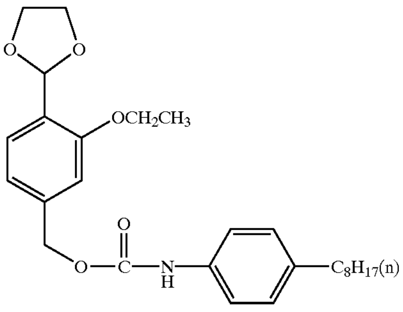
(41)
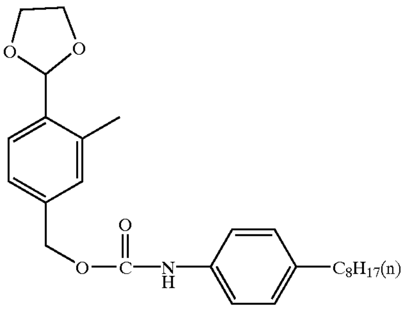
(42)
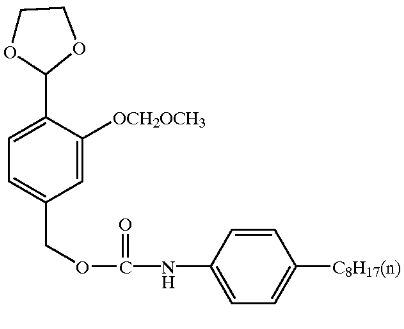
-continued
(43)
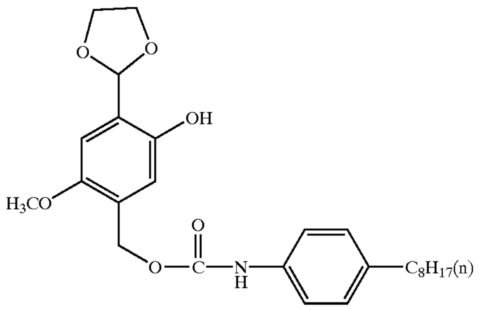
(44)
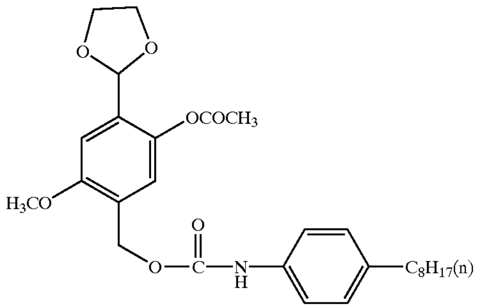
(45)
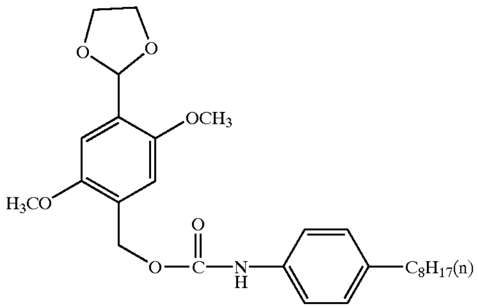
The following are NMR data of compounds (36) to (45) shown above.
| $^1HNMR(CDCl_3)\delta ppm$ | |
|---|---|
| (36) | |
| δ 3.8 | (s, 6H) |
| δ 4.7 | (s, 2H) |
| δ 6.1 | (s, 1H) |
| δ 6.8 | (d, 1H) |
| δ 7.1 | (s, 1H) |
| δ 7.5 | (d, 1H) |
| (37) | |
| δ 4.0 to 4.3 | (m, 4H) |
| δ 4.8 | (s, 2H) |
| δ 6.1 | (s, 1H) |
| δ 6.9 | (d, 1H) |
| δ 7.0 | (s, 1H) |
| δ 7.4 | (d, 1H) |
| (38) | |
| δ 1.3 | (t, 3H) |
| δ 3.7 | (s, 6H) |
| δ 4.0 | (q, 2H) |
| δ 5.3 | (s, 2H) |
| δ 6.0 | (s, 1H) |
| δ 6.8 | (d, 1H) |
| δ 7.1 | (d, 1H) |

-continued

| $^1$HNMR($CDCl_3$)δppm | |
|---|---|
| δ 7.5 | (d, 1H) |
| (39) | |
| δ 1.3 | (t, 3H) |
| δ 4.0 | (q, 2H) |
| δ 5.4 | (s, 2H) |
| δ 6.0 | (s, 1H) |
| δ 6.8 to 7.3 | (m, 7H) |
| (40) | |
| δ 0.9 | (t, 3H) |
| δ 1.0 to 1.8 | (m, 15H) |
| δ 2.5 | (t, 2H) |
| δ 3.6 | (q, 2H) |
| δ 4.0 to 4.4 | (m, 4H) |
| δ 5.2 | (s, 2H) |
| δ 6.1 | (s, 1H) |
| δ 6.5 | (s, 1H) |
| δ 7.0 to 7.5 | (m, 7H) |
| (41) | |
| δ 0.9 | (t, 3H) |
| δ 1.0 to 1.8 | (m, 12H) |
| δ 2.5 | (t, 2H) |
| δ 4.0 to 4.4 | (m, 4H) |
| δ 5.0 | (s, 2H) |
| δ 6.1 | (S, 1H) |
| δ 6.8 | (s, 1H) |
| δ 7.1 to 7.4 | (m, 7H) |
| (42) | |
| δ 0.9 | (t, 3H) |
| δ 1.0 to 1.8 | (m, 12H) |
| δ 2.5 | (t, 2H) |
| δ 3.5 | (s, 3H) |
| δ 4.0 to 4.4 | (m, 4H) |
| δ 5.1 | (s, 2H) |
| δ 5.5 | (s, 2H) |
| δ 6.4 | (s, 1H) |
| δ 6.8 | (s, 1H) |
| δ 7.1 to 7.4 | (m, 7H) |
| (43) | |
| δ 0.9 | (t, 3H) |
| δ 1.0 to 1.8 | (m, 12H) |
| δ 2.5 | (t, 2H) |
| δ 3.8 | (s, 3H) |
| δ 4.0 to 4.4 | (m, 4H) |
| δ 5.1 | (s, 2H) |
| δ 6.3 | (s, 1H) |
| δ 6.6 | (s, 1H) |
| δ 7.0 to 7.4 | (m, 6H) |
| (44) | |
| δ 0.9 | (t, 3H) |
| δ 1.0 to 1.8 | (m, 12H) |
| δ 2.0 | (s, 3H) |
| δ 2.5 | (t, 2H) |
| δ 3.9 | (s, 3H) |
| δ 4.0 to 4.4 | (m, 4H) |
| δ 5.3 | (s, 2H) |
| δ 6.3 | (s, 1H) |
| δ 6.8 | (s, 1H) |
| δ 7.0 to 7.3 | (m, 6H) |
| (45) | |
| δ 0.9 | (t, 3H) |
| δ 1.0 to 1.8 | (m, 12H) |
| δ 2.6 | (t, 2H) |
| δ 3.5 | (s, 3H) |
| δ 3.8 | (s, 3H) |
| δ 4.0 to 4.4 | (m, 4H) |
| δ 5.2 | (s, 2H) |
| δ 6.0 | (s, 1H) |
| δ 6.3 | (s, 1H) |
| δ 7.0 to 7.3 | (m, 6H) |

Now, the color-developing agent precursor represented by formula (D1) contained in the silver halide color photographic light-sensitive material of the present invention is described in detail below.

In formula (D1), the $Ar^2$ group is a substituted or unsubstituted aryl group, or a substituted or unsubstituted heterocyclic group. As the aryl group, preferably those having 6 to 30 carbon atoms and specifically a phenyl group, a naphthyl group, and the like can be mentioned. Further, as the heterocyclic group, preferably those that are 3- to 8-membered and have at least one oxygen atom, nitrogen atom, or sulfur atom as the hetero atom in the atoms constituting the ring can be mentioned. The heterocyclic group may form a condensed ring with another aromatic ring, and specifically a 2-pyridyl group, a 2-furyl group, a 2-benzoxazolyl group, a 2-thienyl group, and the like can be mentioned. As $Ar^2$, an phenyl group is particularly preferable.

In formula (D1), the $Ar^2$ group may have a substituent, and specific examples of the substituent include a hydroxyl group, a cyano group, a carboxyl group, a halogen atom (e.g., fluorine, chlorine, and bromine), a straight-chain or branched alkyl group preferably having 1 to 60 carbon atoms (e.g., methyl, ethyl, propyl, isopropyl, t-butyl, 2-ethylhexyl, nonyl, undecyl, pentadecyl, n-hexadecyl, and 3-decaneamidopropyl), a cycloalkyl group preferably having 3 to 60 carbon atoms (e.g., cyclopropyl, 1-ethylcyclopropyl, cyclopentyl, and cyclohexyl), an aryl group preferably having 6 to 30 carbon atoms (e.g., phenyl and naphthyl), a heterocyclic group preferably having 2 to 60 carbon atoms (a 3- to 8-membered monocyclic ring or condensed ring which has at least one oxygen atom, nitrogen atom, or sulfur atom as the hetero atom, e.g., 2-pyridyl, 2-furyl, 2-benzoxazolyl, and 2-thienyl), an alkoxy group preferably having 1 to 60 carbon atoms (e.g., methoxy, ethoxy, butoxy, n-octyloxy, hexadecyloxy, and 2-methoxyethoxy), an aryloxy group preferably having 6 to 60 carbon atoms (e.g., phenoxy, 2,4-t-amylphenoxy, 4-t-butylphenoxy, and naphthoxy), an acyloxy group preferably having 6 to 60 carbon atoms (e.g., benzoyloxy, octanoyloxy, 2-hexadecanoyloxy, and 2-(2',4'-di-t-amylphenoxy) butanoyloxy), an acylamino group preferably having 2 to 60 carbon atoms (e.g., acetylamino, n-butanoylamino, octanoylamino, 2-hexadecanoylamino, 2-(2',4'-di-t-amylphenoxy)butanoylamino, benzoylamino, and nicotinoylamino), a sulfonylamino group preferably having 1 to 60 carbon atoms (e.g., methanesulfonylamino and phenylsulfonylamino), another amino group preferably having 0 to 60 carbon atoms (e.g., an unsubstituted amino group, a monoalkylamino group, a dialkylamino group, an arylamino group, and an alkylarylamino group, and specifically unsubstituted amino, diethylamino, n-octylamino, 3-(2',4'-di-t-amylphenoxy)propylamino, and morpholino), an alkylthio group preferably having 1 to 60 carbon atoms (e.g, methylthio, ethylthio, butylthio, and hexadecylthio), an arylthio group preferably having 6 to 60 carbon atoms (e.g., phenylthio and 4-dodecyloxyphenylthio), an acyl group preferably having 1 to 60 carbon atoms (e.g., acetyl, benzoyl, butanoyl, and decanoyl), a sulfonyl group preferably having 1 to 60 carbon atoms (e.g., methanesulfonyl, butanesulfonyl, and toluenesulfonyl), an alkoxycarbonyl group preferably having 2 to 60 carbon atoms (e.g., ethoxycarbonyl, hexyloxycarbonyl, and dodecyloxycarbonyl), an aryloxycarbonyl group preferably having 7 to 30 carbon atoms (e.g., phenoxycarbonyl and naphthyloxycarbonyl), a carbamoyl group preferably having 1 to 60 carbon atoms (e.g., N,N-dicyclohexylcarbamoyl), and a sulfamoyl group preferably having 0 to 60 carbon atoms (e.g., N,N-dimethylsulfamoyl).

Among these substituents, preferable ones are a hydroxyl group, an alkyl group, an alkoxy group, an aryloxy group, an acylamino group, and a sulfonylamino group, and particularly preferable ones are a hydroxyl group, an alkoxy group, and a sulfonylamino group.

If possible, these substituents may bond together to form a ring. Further, if possible, these substituents may further have a substituent, and the substituent includes those enumerated as a substituent on the above $Ar^2$ group, and it is preferably an alkyl group, an alkoxy group, an aryloxy group, an acyl group, an alkoxycarbonyl group, an aryloxycarbonyl group, a carbamoyl group, a sulfonyl group, a sulfamoyl group, a cyano group, a carboxyl group, or a hydroxyl group, and particularly preferably an alkyl group, an alkoxy group, or an alkoxycarboxyl group.

Preferably at least one of substituents on the $Ar^2$ group has a ballasting group built therein, which ballasting group is usually used in a nondiffusing photographic additive, such as a coupler. The ballasting group is a photographically inactive group having, for example, more than 7 carbon atoms, and it can be chosen from an alkyl group, an alkoxy group, an aryl group, an aryloxy group, an amido group, a ureido group, a sulfonamido group, an ester group, a sulfonyl group, an acyl group, and the like, or a combination of these, or a combination thereof with a hydroxyl group or the like.

In formula (D1), $X^2$ is a substituted or unsubstituted methylene group, and the substituent thereof includes those on the $Ar^2$ group described above. With respect to the position where $X^2$ is bonded to $Ar^2$, when the Ar group is an aryl ring, the position is the ortho position or the para position with respect to the formyl group, while when the $Ar^2$ group is a heterocyclic ring, the position is the 2-position or the 4-position with it being assumed that the position of the formyl group is the 1-position; and the positional relationship of $X^2$ on the $Ar^2$ group is such that after the formyl group is converted to a hydroxyl group, the color-developing agent (PPD) may be released by electron transfer.

$L^2$ represents a linking group, examples of which include a known timing group, such as the group

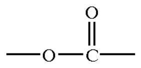

described in DE-A-2 803 145. In the case of this group, the (—O) atom bonds to the releasable compound (OHC—$Ar^2$—$X^2$—), and the carbon atom bonds to the hetero atom in the color-developing agent (PPD), to link the releasable compound to the color-developing agent.

Further, there can be mentioned, for example, a group as described in DE-A-2 855 697 that, when released from the color-developing agent precursor of formula (D1), undergoes an intramolecular nucleophilic reaction, to release the color-developing agent; and a group as described in DE-A-3 105 026 that, after being released from the color-developing agent precursor of formula (D1), allows electron transfer to take place along the conjugated system, to release the color-developing agent. Further, $L^2$ may represent a group that, when released from the compound of formula (D1), itself can take part in a coupling reaction or a redox reaction, to release PPD, imagewise, by a coupling reaction with a nucleophilic agent released imagewise as a result of the reaction, or by an imagewise redox reaction with a silver halide.

m2 is an integer of 0 to 3, with preference given to 1 or 2.

PPD represents a group to give a color-developing agent, and as the color-developing agent, a p-phenylenediamine derivative is preferable. Preferable examples include p-phenylenediamine derivatives described in JP-A-4-249244, page 7, left column, line 23, to right column, line 16, and in JP-A-4-443, page 4, right lower column, line 7, to page 6, line 20, and preferable specific examples include N,N-diethyl-p-phenylenediamine, 4-amino-N,N-diethyl-3-methylaniline, 4-amino-N-(β-hydroxyethyl)-N-methylaniline, 4-amino-N-ethyl-N-(β-hydroxyethyl)aniline, 4-amino-N-ethyl-N-(β-hydroxyethyl)-3-methylaniline, 4-amino-N-ethyl-N-(3-hydroxypropyl)-3-methylaniline, 4-amino-N-ethyl-N-(4-hydroxybutyl)-3-methylaniline, 4-amino-N-ethyl-N-(β-methanesulfonamidoethyl)-3-methylaniline, 4-amino-N,N-diethyl-3-(β-hydroxyethyl) aniline, 4-amino-N-ethyl-N-(β-methoxyethyl)-3-methylaniline, 4-amino-N-(β-ethoxyethyl)-N-ethyl-3-methylaniline, 4-amino-N-(3-carbamoylpropyl)-N-n-propyl-3-methylaniline, 4-amino-N-(3-carbamoylbutyl)-N-n-propyl-3-methylaniline, N-(4-amino-3-methylphenyl-3-hydroxypyrrolidine, N-(4-amino-3-methylphenyl-3-(hydroxymethyl)pyrrolidine, and N-(4-amino-3-methylphenyl)-3-pyrrolidinecarboxamide; among the above p-phenylenediamine derivatives, preferable ones are 4-amino-N-ethyl-N-(β-methanesulfonamidoethyl)-aniline, 4-amino-N-ethyl-N(β-hydroxyethyl)-3-methylaniline, 4-amino-N-ethyl-N-(3-hydroxypropyl)-3-methylaniline and 4-amino-N-ethyl-N-(4-hydroxybutyl)-3-methylaniline.

Among the compounds represented by formula (D1), preferable compounds are ones represented by formula (D2).

In formula (D2), $L^2$ and PPD have the same meanings to those of formula (D1). As a group represented by $R^{40}$, substituents mentioned for the substituent in formula (D1) can be applied. Preferably, $R^{40}$ represents a hydroxyl group, an alkyl group, an aryl group, an alkoxy group, an aryloxy group, an acyloxy group, an acylamino group, a sulfonylamino group, or another amino group, and particularly preferably, $R^{40}$ represents a hydroxyl group, an alkyl group, an alkoxy group, an acylamino group, or another amino group. —$CH_2$— represents a methylene group positioned at the ortho or para position with respect to the formyl group. 12 is an integer, and preferably, 12 is 0 or 1. n2 is an integer of 1 to 4, and preferably n2 is 1 or 2.

Among the compounds represented by formula (D2), preferable compounds are ones represented by formula (D3).

In formula (D3), $R^{41}$ represents a hydrogen atom, an alkyl group, an aryl group, or an acyl group, $R^{40}$ and PPD have the same meanings to those of formula (D2), and r2 is an integer of 1 to 3. —$CH_2$— represents a methylene group positioned at the ortho or para position with respect to the formyl group.

As specific examples of the compound included in formula (D1) for use in the present invention, can be mentioned the above exemplified compounds (1) to (20) and the following exemplified compounds (46) to (51), but the present invention is not limited to them.

(46)

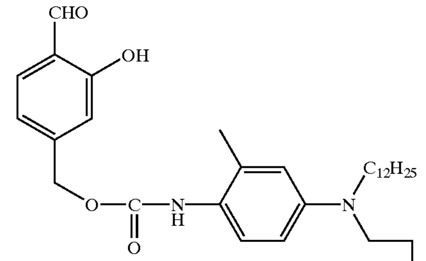

(47)

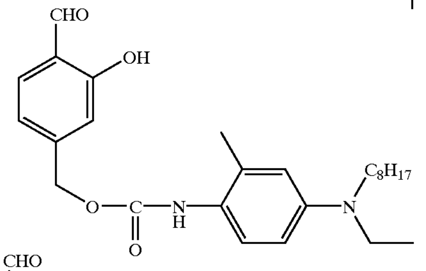

(48)

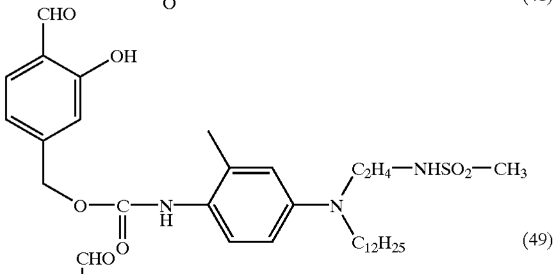

(49)

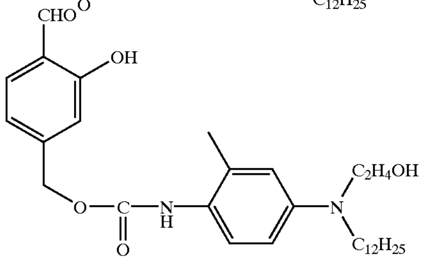

(50)

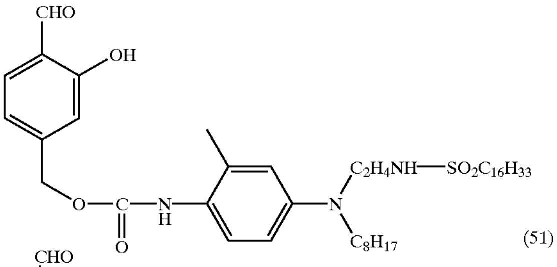

(51)

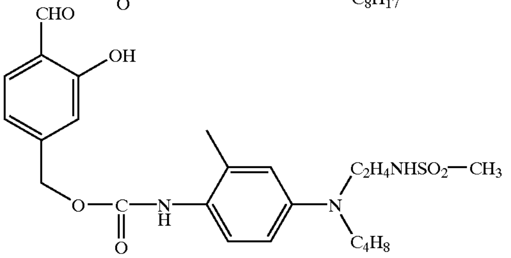

Next, a light-sensitive material containing the compound for use in the present invention is explained in detail.

When the compound for use in the present invention is added into a light-sensitive material, it is difficult for the compound represented by formula (1) or the color-developing agent precursor represented by formula (D1) to release the photographically useful group or the color-developing agent, respectively, if there is not a suitable peroxide; that is, if the compound of the formula (1) or (D1) is placed in a simple alkaline solution. Therefore, in the present invention, a processing solution, preferably an activator solution needs to contain a suitable peroxide. Herein a suitable peroxide, which includes a peracid, is, for example, a compound represented by the following formula:

ROOH

RCOOOH wherein R represents a hydrogen atom, or a substituted or unsubstituted alkyl group or aryl group.

When the peroxide represented by the above formula is added, for example, to an image-forming processing solution, the protected photographically useful group represented by formula (1) or the group represented by formula (D1) protected to give a color-developing agent reacts with a suitable peroxide in the processing solution during the processing, to release quickly the photographically useful group or the color-developing agent, so that its specific activity or development properties can be exhibited.

Suitable examples of the peroxide are shown below:

HOOH t—BuOOH

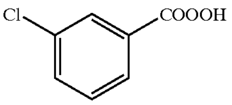

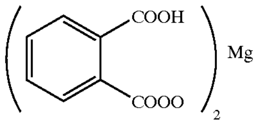

$K_2CO_4$ $Na_2CO_4$ $KBO_3 \cdot 1/2H_2O$ $NaBO_3 \cdot 4H_2O$

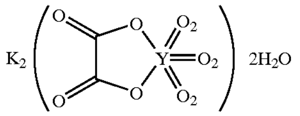

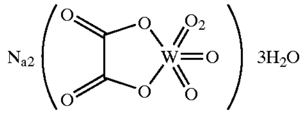

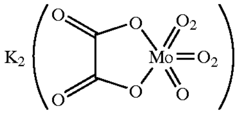

In the present invention, the amount of the peroxide to be added in a processing solution is preferably 0.1 mmol/liter to 1 mol/liter, and more preferably 0.1 mmol/liter to 0.5 mol/liter.

When the compound represented by formula (1) for use in the present invention is added into a light-sensitive material, it can be contained to use in at least one of a protective layer, a light-sensitive silver halide emulsion layer, a non-light-sensitive, fine-particle silver halide emulsion layer, an intermediate layer, a filter layer, an undercoat layer, an antihalation layer, and the like in the light-sensitive material, and preferably it is used in a light-sensitive emulsion layer. The compounds represented by formula (1) for use in the present invention can be used in the form of a combination of two or more.

Now, when, out of the compounds represented by formula (1), the compound in which PUG is a group to give a color-developing agent, PPD (hereinafter the compound is abbreviated to a color-developing agent precursor) is used, the light-sensitive material of the present invention that is applied is described, as well as the light-sensitive material of the present invention containing the color-developing agent precursor represented by formula (D1).

Herein, the light-sensitive material of the present invention means to include both of the above light-sensitive materials, unless otherwise specified.

As couplers that are preferably used in the present invention, compounds having structures described by the following formulae (8) to (19) are mentioned. They are compounds collectively generally referred to as active methylenes, pyrazolones, pyrazoloazoles, phenols, naphthols, and pyrrolotriazoles, respectively, which are compounds known in the art.

(8)

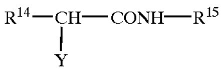

(9)

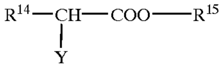

(10)

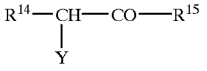

(11)

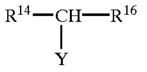

(12)

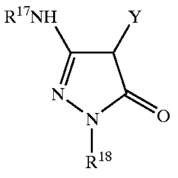

(13)

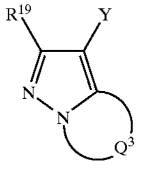

-continued (14)

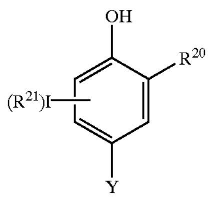

(15)

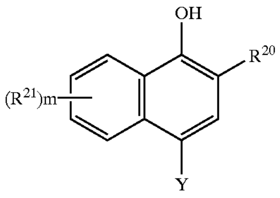

(16)

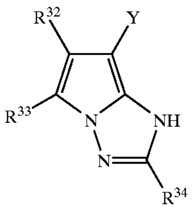

(17)

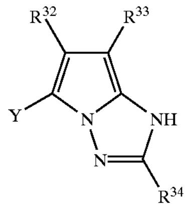

(18)

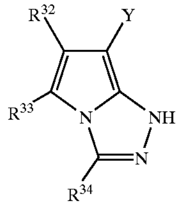

(19)

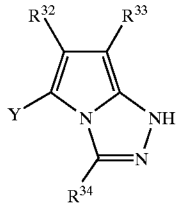

Formulae (8) to (11) represent couplers that are called active methylene couplers, and, in the formulae, $R^{14}$ represents an acyl group, a cyano group, a nitro group, an aryl group, a heterocyclic residue, an alkoxycarbonyl group, an aryloxycarbonyl group, a carbamoyl group, a sulfamoyl group, an alkylsulfonyl group, or an arylsulfonyl group, optionally substituted.

In formulae (8) to (10), $R^{15}$ represents an optionally substituted alkyl group, aryl group, or heterocyclic residue. In formula (11), $R^{16}$ represents an optionally substituted aryl group or heterocyclic residue.

Examples of the substituent that may be possessed by $R^{14}$, $R^{15}$, and $R^{16}$ include a hydrogen atom or a substituent. Examples of the substituent include a straight-chain or branched, chain or cyclic alkyl group having 1 to 50 carbon atoms (e.g. trifluoromethyl, methyl, ethyl, propyl, heptafluoropropyl, isopropyl, butyl, t-butyl, t-pentyl, cyclopentyl, cyclohexyl, octyl, 2-ethylhexyl, and dodecyl); a straight-chain or branched, chain or cyclic alkenyl group having 2 to 50 carbon atoms (e.g. vinyl, 1-methylvinyl, and cyclohexen-1-yl); an alkynyl group having 2 to 50 carbon atoms in all (e.g. ethynyl and 1-propinyl), an aryl group having 6 to 50 carbon atoms (e.g. phenyl, naphthyl, and anthryl), an acyloxy group having 1 to 50 carbon atoms (e.g. acetoxy, tetradecanoyloxy, and benzoyloxy), a carbamoyloxy group having 1 to 50 carbon atoms (e.g. N,N-dimethylcarbamoyloxy), a carbonamido group having 1 to 50 carbon atoms (e.g. formamido, N-methylacetamido, acetamido, N-methylformamido, and benzamido), a sulfonamido group having 1 to 50 carbon atoms (e.g. methanesulfonamido, dodecansulfonamido, benzenesulfonamido, and p-toluenesulfonamido), a carbamoyl group having 1 to 50 carbon atoms (e.g. N-methylcarbamoyl, N,N-diethylcarbamoyl, and N-mesylcarbamoyl), a sulfamoyl group having 0 to 50 carbon atoms (e.g. N-butylsulfamoyl, N,N-diethylsulfamoyl, and N-methyl-N-(4-methoxyphenyl) sulfamoyl), an alkoxy group having 1 to 50 carbon atoms (e.g. methoxy, propoxy, isopropoxy, octyloxy, t-octyloxy, dodecyloxy, and 2-(2,4-di-t-pentylphenoxy)ethoxy), an aryloxy group having 6 to 50 carbon atoms (e.g. phenoxy, 4-methoxyphenoxy, and naphthoxy), an aryloxycarbonyl group having 7 to 50 carbon atoms (e.g. phenoxycarbonyl and naphthoxycarbonyl), an alkoxycarbonyl group having 2 to 50 carbon atoms (e.g. methoxycarbonyl and t-butoxycarbonyl), an N-acylsulfamoyl group having 1 to 50 carbon atoms (e.g. N-tetradecanoylsulfamoyl and N-benzoylsulfamoyl), an alkylsulfonyl group having 1 to 50 carbon atoms (e.g. methanesulfonyl, octylsulfonyl, 2-methoxyethylsulfonyl, and 2-hexyldecylsulfonyl), an arylsulfonyl group having 6 to 50 carbon atoms (e.g. benzenesulfonyl, p-toluenesulfonyl, and 4-phenylsulfonylphenylsulfonyl), an alkoxycarbonylamino group having 2 to 50 carbon atoms (e.g. ethoxycarbonylamino), an aryloxycarbonylamino group having 7 to 50 carbon atoms (e.g. phenoxycarbonylamino and naphthoxycarbonylamino), an amino group having 0 to 50 carbon atoms (e.g. amino, methylamino, diethylamino, diisopropylamino, anilino, and morpholino), a cyano group, a nitro group, a carboxyl group, a hydroxyl group, a sulfo group, a mercapto group, an alkylsulfinyl group having 1 to 50 carbon atoms (e.g. methanesulfinyl and octanesulfinyl), an arylsulfinyl having 6 to 50 carbon atoms (e.g. benzenesulfinyl, 4-chlorophenylsulfinyl, and p-toluenesulfinyl), an alkylthio group having 1 to 50 carbon atoms (e.g. methylthio, octylthio, and cyclohexylthio), an arylthio group having 6 to 50 carbon atoms (e.g. phenylthio and naphthylthio), a ureido group having 1 to 50 carbon atoms (e.g. 3-methylureido, 3,3-dimethylureido, and 1,3-diphenylureido), a heterocyclic group having 2 to 50 carbon atoms (e.g. a 3-membered to 12-membered monocyclic ring or condensed ring having at least one hetero atom(s), such as nitrogen, oxygen, and sulfur, for example, 2-furyl, 2-pyranyl, 2-pyridyl, 2-thienyl, 2-imidazolyl, morpholino, 2-quinolyl, 2 -benzimidazolyl, 2-benzothiazolyl, and 2-benzoxazolyl), an acyl group having 1 to 50 carbon atoms (e.g. acetyl, benzoyl, and trifluoroacetyl), a sulfamoylamino group having 0 to 50 carbon atoms (e.g. N-butylsulfamoylamino and N-phenylsulfamoylamino), a silyl group having 3 to 50 carbon atoms (e.g. trimethylsilyl, dimethyl-t-butylsilyl, and triphenylsilyl), and a halogen atom (e.g. a fluorine atom, a chlorine atom, and a bromine atom). The above substituents may further have a substituent, and examples of such a substituent include those mentioned above.

Further, these substituents may bond together to form a condensed ring. As a condensed ring, a 5- to 7-membered ring is preferable, and a 5- or 6-membered ring is more preferable.

The number of carbon atoms of the substituent is preferably 50 or below, more preferably 42 or below, and most preferably 34 or below, and there is preferably 1 or more carbon atom(s).

In formulae (8) to (11), Y represents a hydrogen atom or a group capable of coupling split-off by coupling reaction with the oxidation product of the color-developing agent. Examples of Y are a heterocyclic group (a saturated or unsaturated 5-membered to 7-membered monocyclic or condensed ring having as a hetero atom at least one nitrogen atom, oxygen atom, sulfur atom, or the like, e.g. succinimido, maleinimido, phthalimido, diglycolimido, pyrrole, pyrazole, imidazole, 1,2,4-triazole, tetrazole, indole, benzopyrazole, benzimidazole, benzotriazole, imidazolin-2,4-dione, oxazolidin-2,4-dione, thiazolidin-2,4-dione, imidazolidin-2-one, oxazolin-2-one, thiazolin-2-one, benzimidazolin-2-one, benzoxazolin-2-one, benzthiazolin-2-one, 2-pyrrolin-5-one, 2-imidazolin-5-one, indolin-2,3-dione, 2,6-dioxypurine, parabic acid, 1,2,4-triazolidin-3,5-dione, 2-pyridone, 4-pyridone, 2-pyrimidone, 6-pyridazone, 2-pyrazone, 2-amino-1,3,4-thiazolidine, and 2-imino-1,3,4-thiazolidin-4-one), a halogen atom (e.g. a chlorine atom and a bromine atom), an aryloxy group (e.g. phenoxy and 1-naphthoxy), a heterocyclic oxy group (e.g. pyridyloxy and pyrazolyoxy), an acyloxy group (e.g. acetoxy and benzoyloxy), an alkoxy group (e.g. methoxy and dodecyloxy), a carbamoyloxy group (e.g. N,N-diethylcarbamoyloxy and morpholinocarbonyloxy), an aryloxycarbonyloxy group (e.g. phenoxylcarbonyloxy), an alkoxycarbonyloxy group (e.g. methoxycarbonyloxy and ethoxycarbonyloxy), an arylthio group (e.g. phenylthio and naphthylthio), a heterocyclic thio group (e.g. tetrazolylthio, 1,3,4-thiadiazolylthio, 1,3,4-oxadiazolylthio, and benzimidazolylthio), an alkylthio group (e.g. methylthio, octylthio, and hexadecylthio), an alkylsulfonyloxy group (e.g. methanesulfonyloxy), an arylsulfonyloxy group (e.g. benzenesulfonyloxy and toluenesulfonyloxy), a carbonamido group (e.g. acetamido and trifluoroacetamido), a sulfonamide group (e.g. methanesulfonamido and benzenesulfonamido), an alkylsulfonyl group (e.g. methanesulfonyl), an arylsulfonyl group (e.g. benzenesulfonyl), an alkylsulfinyl group (e.g. methanesulfinyl), an arylsulfinyl group (e.g. benzenesulfinyl), an arylazo group (e.g. phenylazo and naphthylazo), and a carbamoylamino group (e.g. N-methylcarbamoylamino).

Y may be substituted with a substituent, and examples of the substituent that may be possessed by Y include those mentioned for $R^{14}$, $R^{15}$, and $R^{16}$.

Preferably Y represents a halogen atom, an aryloxy group, a heterocyclic oxy group, an acyloxy group, an aryloxycarbonyloxy group, an alkoxycarbonyloxy group, or a carbamoyloxy group.

In formulae (8) to (11), $R^{14}$ and $R^{15}$, and $R^{14}$ and $R^{16}$, may bond together to form a ring.

Formula (12) represents a coupler that is called a 5-pyrazolone coupler, and in the formula, $R^{17}$ represents an alkyl group, an aryl group, an acyl group, or a carbamoyl group. $R^{18}$ represents a phenyl group or a phenyl group that is substituted by one or more halogen atoms, alkyl groups, cyano groups, alkoxy groups, alkoxycarbonyl groups, or acylamino groups.

Preferable 5-pyrazolone couplers represented by formula (12) are those wherein $R^{17}$ represents an aryl group or an acyl group, and $R^{18}$ represents a phenyl group that is substituted by one or more halogen atoms.

With respect to these preferable groups, more particularly, $R^{17}$ is an aryl group, such as a phenyl group, a 2-chlorophenyl group, a 2-methoxyphenyl group, a 2-chloro-5-tetradecaneamidophenyl group, a 2-chloro-5-(3-octadecenyl-1-succinimido)phenyl group, a 2-chloro-5-octadecylsulfonamidophenyl group, and a 2-chloro-5-[2-(4-hydroxy-3-t-butylphenoxy)tetradecaneamido]phenyl group; or $R_{17}$ is an acyl group, such as an acetyl group, a 2-(2,4-di-t-pentylphenoxy)butanoyl group, a benzoyl group, and a 3-(2,4-di-t-amylphenoxyacetamido)benzoyl group, any of which may have a substituent, such as a halogen atom or an organic substituent that is bonded through a carbon atom, an oxygen atom, a nitrogen atom, or a sulfur atom. Y has the same meaning as defined above.

Preferably $R^{18}$ represents a substituted phenyl group, such as a 2,4,6-trichlorophenyl group, a 2,5-dichlorophenyl group, and a 2-chlorophenyl group.

Formula (13) represents a coupler that is called a pyrazoloazole coupler, and, in the formula, $R^{19}$ represents a hydrogen atom or a substituent. $Q^3$ represents a group of nonmetal atoms required to form a 5-membered azole ring containing 2 to 4 nitrogen atoms, which azole ring may have a substituent (including a condensed ring).

Preferable pyrazoloazole couplers represented by formula (13), in view of spectral absorption characteristics of the color-formed dyes, are imidazo[1,2-b]pyrazoles described in U.S. Pat. No. 4,500,630, pyrazolo[1,5-b]-1,2,4-triazoles described in U.S. Pat. No. 4,500,654, and pyrazolo[5,1-c]-1,2,4-triazoles described in U.S. Pat. No. 3,725,067.

Details of substituents of the azole rings represented by the substituents $R^{19}$ and $Q^3$ are described, for example, in U.S. Pat. No. 4,540,654, the second column, line 41, to the eighth column, line 27. Preferable pyrazoloazole couplers are pyrazoloazole couplers having a branched alkyl group directly bonded to the 2-, 3-, or 6-position of the pyrazolotriazole group, as described in JP-A-61-65245; pyrazoloazole couplers containing a sulfonamide group in the molecule, as described in JP-A-61-65245; pyrazoloazole couplers having an alkoxyphenylsulfonamido ballasting group, as described in JP-A-61-147254; pyrazolotriazole couplers having an alkoxy group or an aryloxy group at the 6-position, as described in JP-A-62-209457 or 63-307453; and pyrazolotriazole couplers having a carbonamido group in the molecule, as described in JP-A-2-201443. Y has the same meaning as defined above.

Formulae (14) and (15) are respectively called phenol couplers and naphthol couplers, and in the formulae $R^{20}$ represents a hydrogen atom or a group selected from the group consisting of $—CONR^{22}R^{23}$, $—SO_2NR^{22}R^{23}$, $—NHCOR^{22}$ $—NHCONR^{22}R^{23}$, and $—NHSO_2NR^{22}R^{23}$. $R^{22}$ and $R^{23}$ each represent a hydrogen atom or a substituent. In formulae (14) and (15), R represents a substituent, l is an integer selected from 0 to 2, and m is an integer selected from 0 to 4. When l and m are 2 or more, $R^{21}$'s may be different. The substituents of $R^{21}$ to $R^{23}$ include those mentioned above as examples for $R^{14}$, $R^{15}$, and $R^{16}$ in the formulae (8) and (10) above. Y has the same meaning as defined above.

Preferable examples of the phenol couplers represented by formula (14) include 2-acylamino-5-alkylphenol couplers described, for example, in U.S. Pat. Nos. 2,369,929, 2,801,171, 2,772,162, 2,895,826, and 3,772,002; 2,5-diacylaminophenol couplers described, for example, in U.S. Pat. Nos. 2,772,162, 3,758,308, 4,126,396, 4,334,011, and 4,327,173, West Germany Patent Publication No. 3 329 729, and JP-A-59-166956; and 2-phenylureido-5-acylaminophenol couplers described, for example, in U.S. Pat. Nos. 3,446,622, 4,333,999, 4,451,559, and 4,427,767. Y has the same meaning as defined above.

Preferable examples of the naphthol couplers represented by formula (15) include 2-carbamoyl-1-naphthol couplers described, for example, in U.S. Pat. Nos. 2,474,293, 4,052,212, 4,146,396, 4,282,233, and 4,296,200; and 2-carbamoyl-5-amido-1-naphthol couplers described, for example, in U.S. Pat. No. 4,690,889. Y has the same meaning as defined above.

Formulas (16) to (19) are couplers called pyrrolotriazoles, and $R^{32}$, $R^{33}$, and $R^{34}$ each represent a hydrogen atom or a substituent. Y has the same meaning as defined above. Examples of the substituent of $R^{32}$, $R^{33}$, and $R^{34}$ include those mentioned for $R^{14}$, $R^{15}$, and $R^{16}$. Preferable examples of the pyrrolotriazole couplers represented by formulae (16) to (19) include those wherein at least one of $R^{32}$ and $R^{33}$ is an electron-attracting group, which specific couplers are described in EP-A-488 248 (A1), 491 197 (A1), and 545 300. Y has the same meaning as defined above.

Further, a fused-ring phenol, an imidazole, a pyrrole, a 3-hydroxypyridine, an active methylene other than the above, an active methine, a 5,5-ring-fused heterocyclic, and a 5,6-ring-fused heterocyclic coupler, can be used.

As the fused-ring phenol couplers, those described, for example, in U.S. Pat. Nos. 4,327,173, 4,564,586, and 4,904,575, can be used.

As the imidazole couplers, those described, for example, in U.S. Pat. Nos. 4,818,672 and 5,051,347, can be used.

As the 3-hydroxypyridine couplers, those described, for example, in JP-A-1-315736, can be used.

As the active methylene and active methine couplers, those described, for example, in U.S. Pat. Nos. 5,104,783 and 5,162,196, can be used.

As the 5,5-ring-fused heterocyclic couplers, for example, pyrrolopyrazole couplers described in U.S. Pat. No. 5,164,289, and pyrroloimidazole couplers described in JP-A-4-174429, can be used.

As the 5,6-ring-fused heterocyclic couplers, for example, pyrazolopyrimidine couplers described in U.S. Pat. No. 4,950,585, pyrrolotriazine couplers described in JP-A-4-204730, and couplers described in EP-556 700, can be used.

In the present invention, in addition to the above couplers, use can be made of couplers described, for example, in West Germany Patent Nos. 3 819 051A and 3 823 049, U.S. Pat. Nos. 4,840,883, 5,024,930, 5,051,347, and 4,481,268, EP-A-304 856 (A2), EP-329 036, EP-A-354 549 (A2), 374 781 (A2), 379 110 (A2), and 386 930 (A1), and JP-A-63-141055, 64-32260, 64-32261, 2-297547, 2-44340, 2-110555, 3-7938, 3-160440, 3-172839, 4-172447, 4-179949, 4-182645, 4-184437, 4-188138, 4-188139, 4-194847, 4-204532, 4-204731, and 4-204732.

Specific examples of the couplers that can be used in the present invention are shown below, but, of course, the present invention is not limited to them:

(C-1)
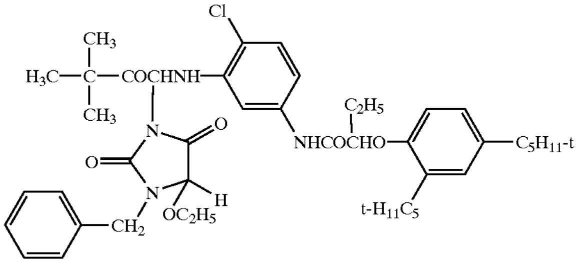
(C-2)
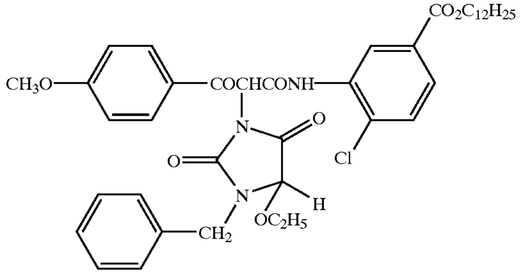
(C-3)
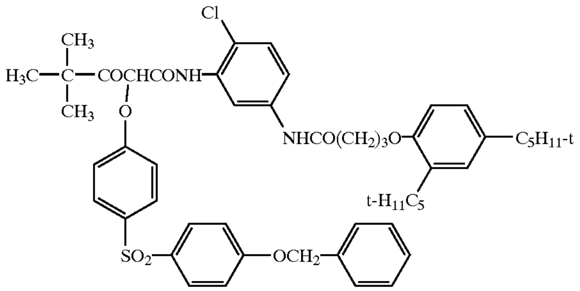
(C-4)
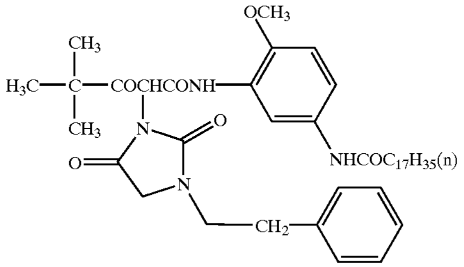
(C-5)
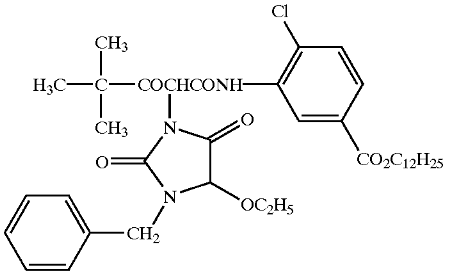
-continued
(C-6)
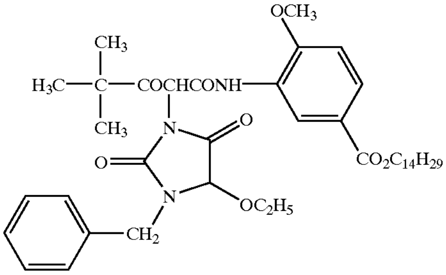
(C-7)
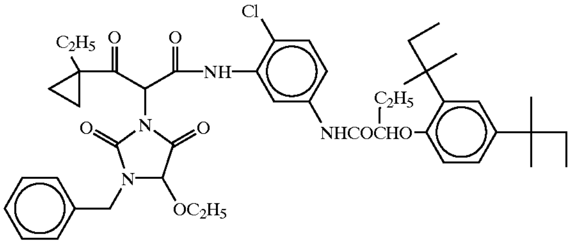
(C-8)
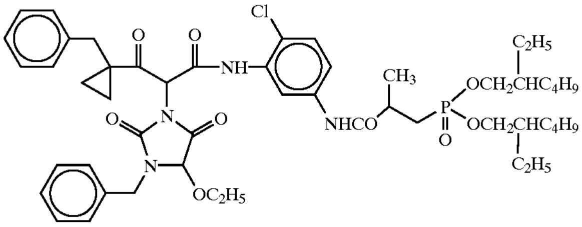
(C-9)
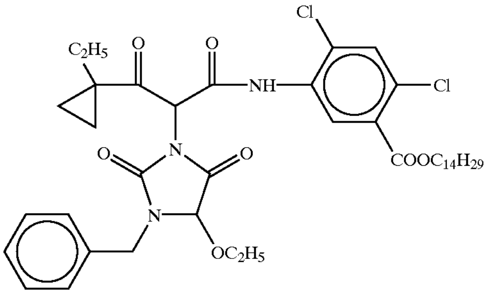
(C-10)
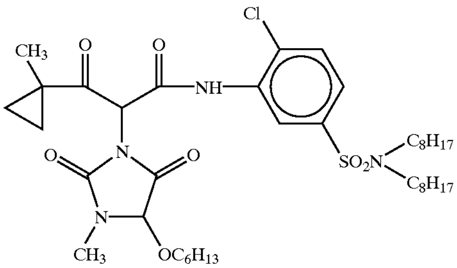

-continued
(C-11)
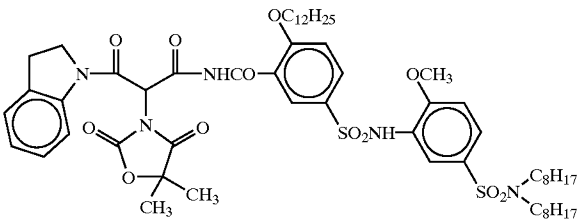
(C-12)
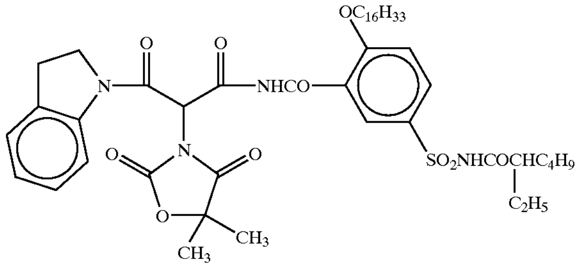
(C-13)
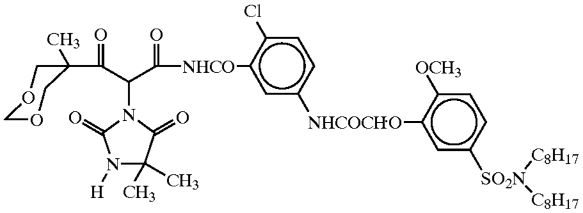
(C-14)
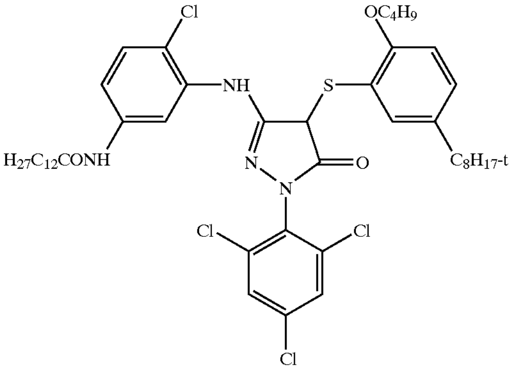
(C-15)
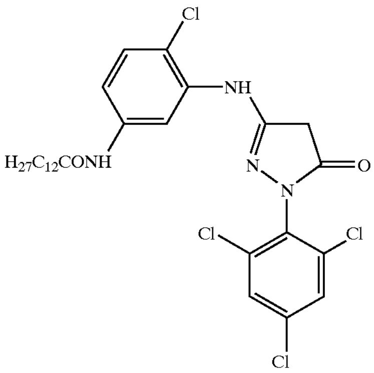
-continued
(C-16)
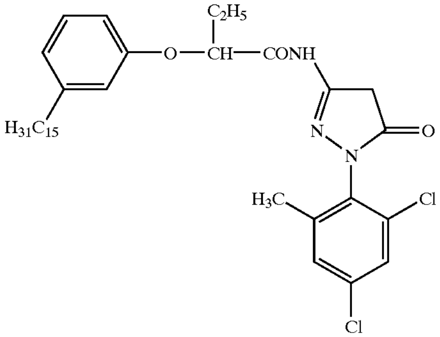
(C-17)
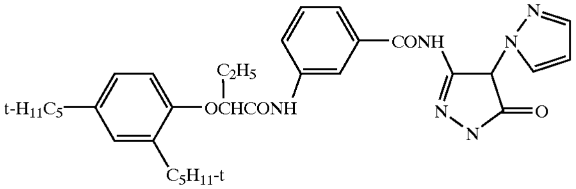
(C-18)
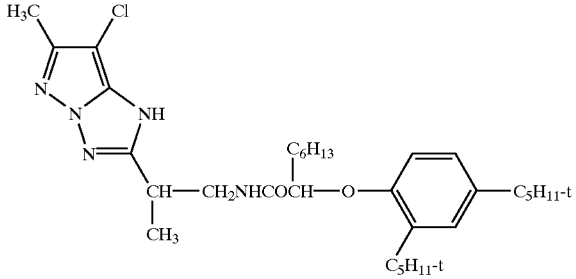
(C-19)
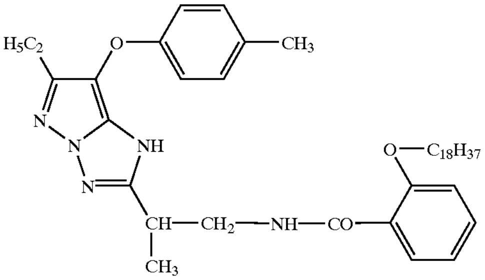
(C-20)
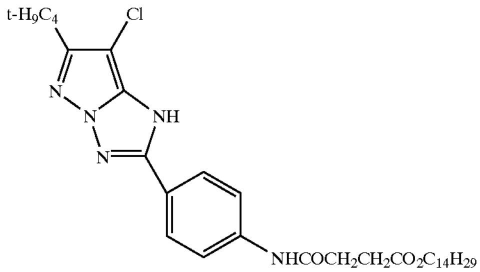

-continued
(C-21)
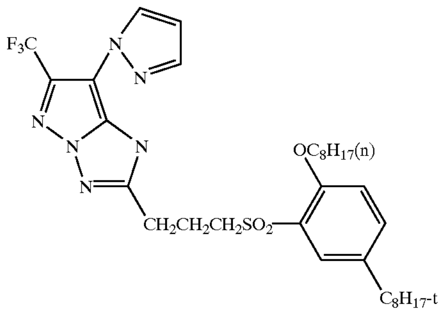
(C-22)
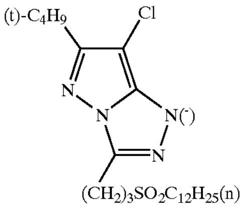
(C-23)
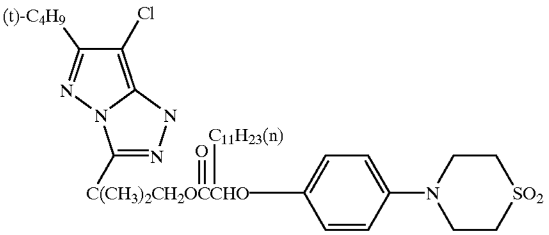
(C-24)
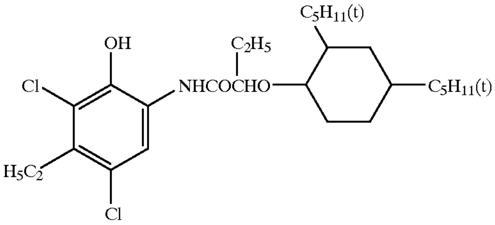
(C-25)
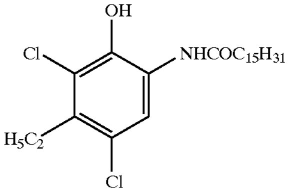
(C-26)
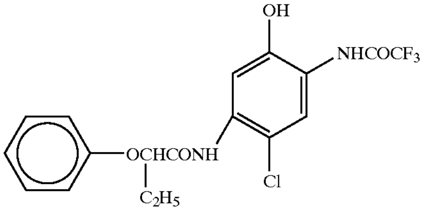
-continued
(C-27)
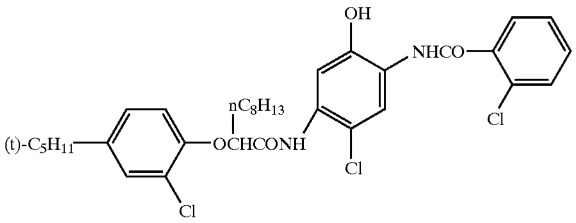
(C-28)
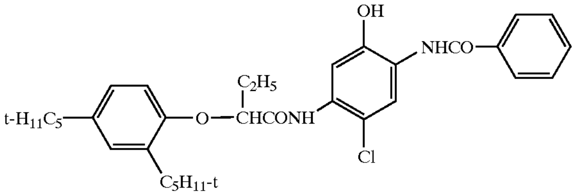
(C-29)
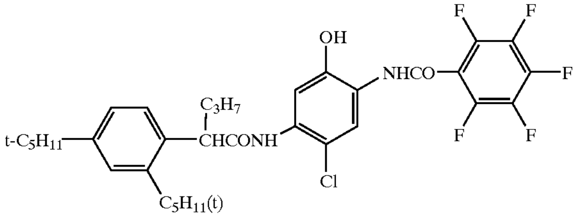
(C-30)
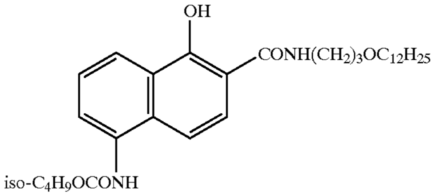
(C-31)
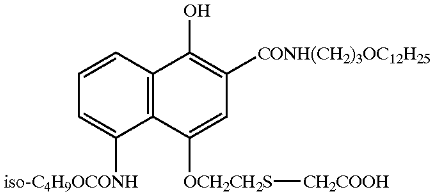
(C-32)
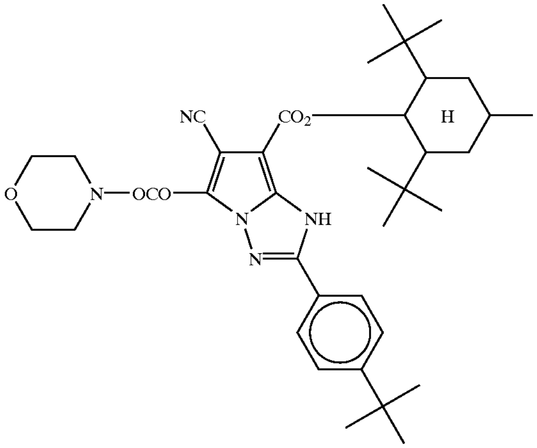

-continued
(C-33)
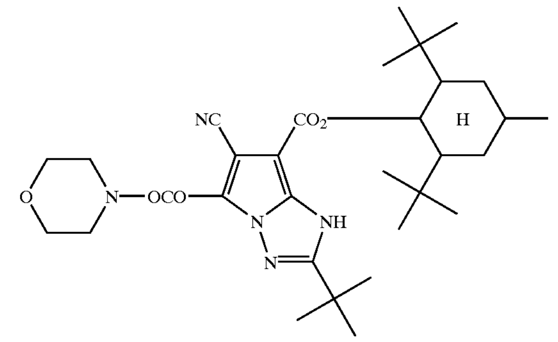
(C-34)
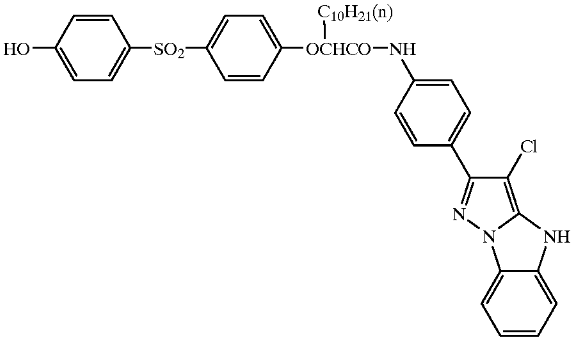
(C-35)
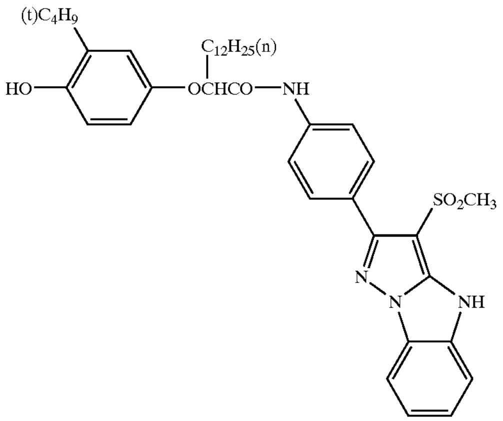
(C-36)
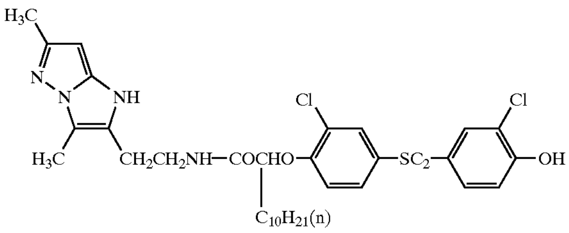
-continued
(C-37)
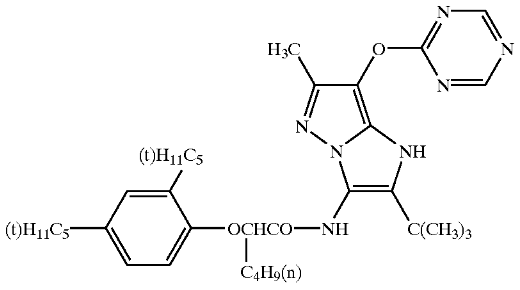
(C-38)
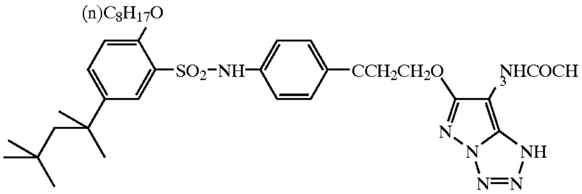
(C-39)
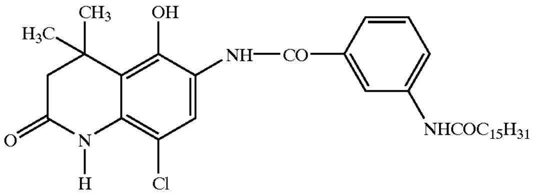
(C-40)
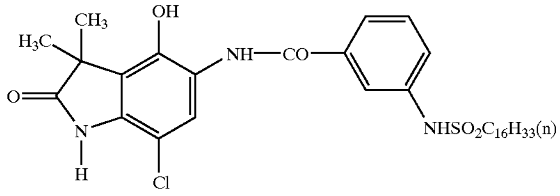
(C-41)
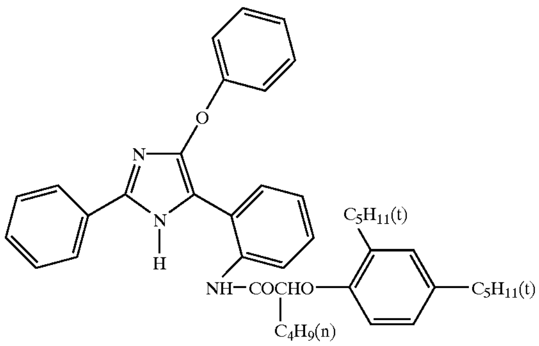

-continued
(C-42)
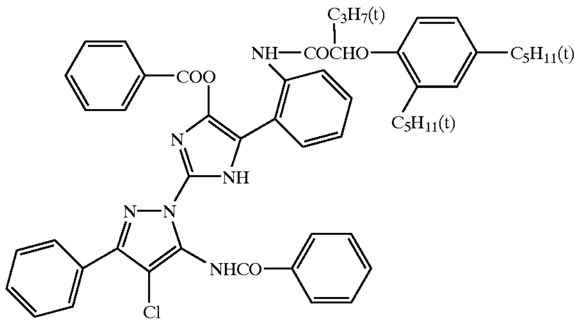
(C-43)
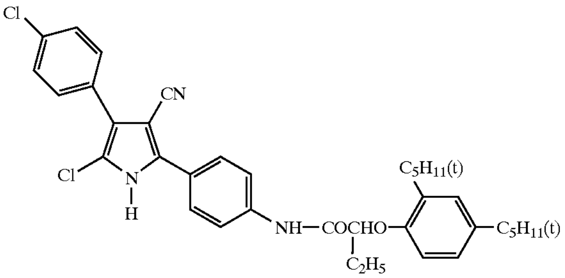
(C-44)
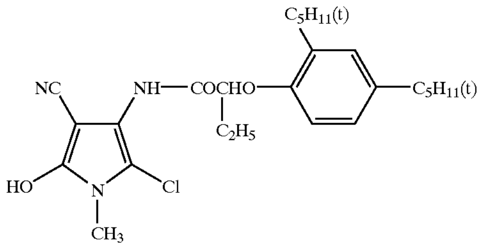
(C-45)
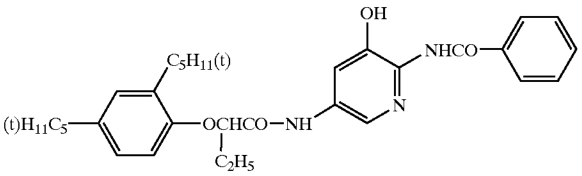
(C-46)
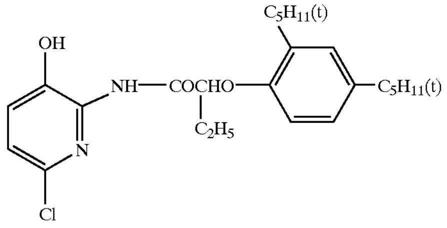
(C-47)
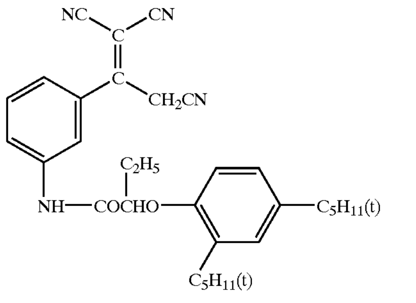
-continued
(C-48)
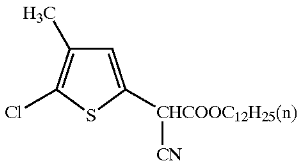
(C-49)
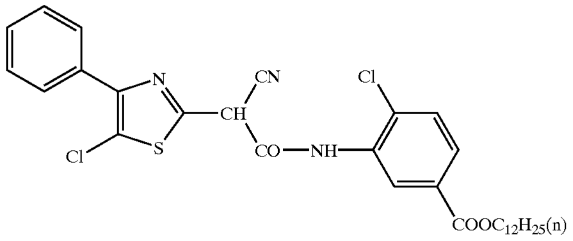
(C-50)
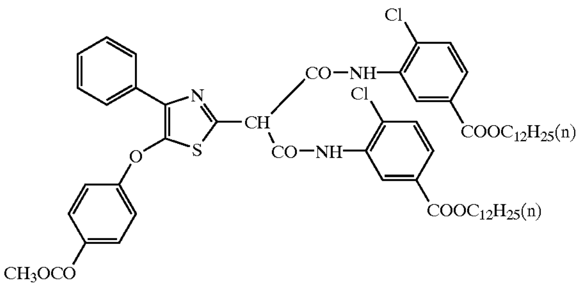
(C-51)
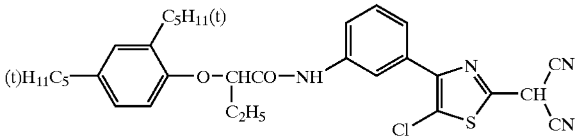
(C-52)
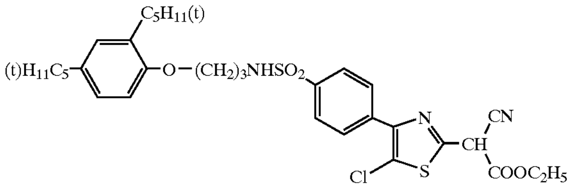
(C-53)
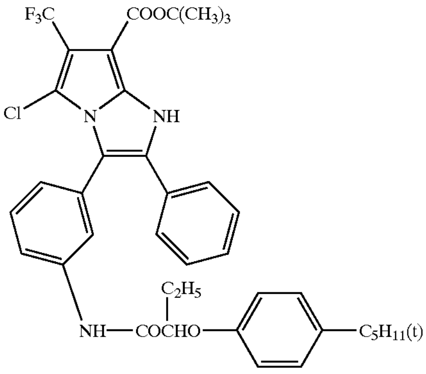

-continued
(C-54)
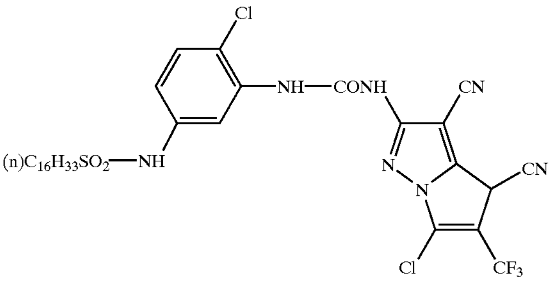
(C-55)
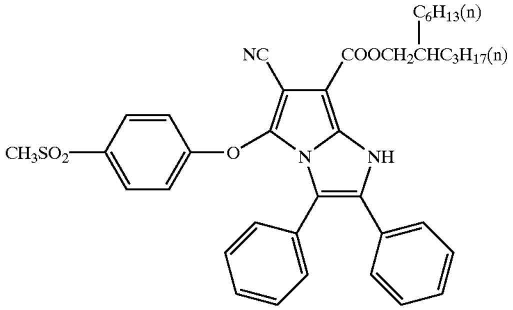
(C-56)
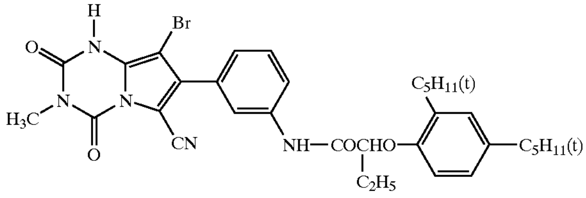
(C-57)
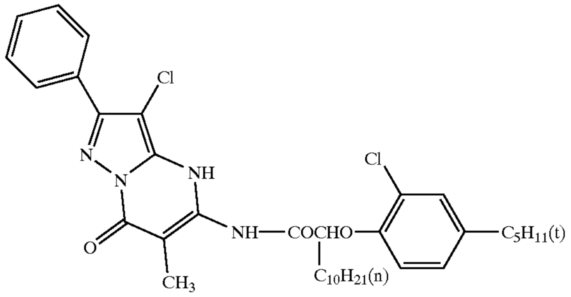
(C-58)
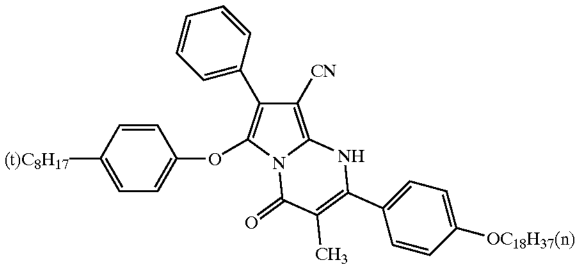
-continued
(C-59)
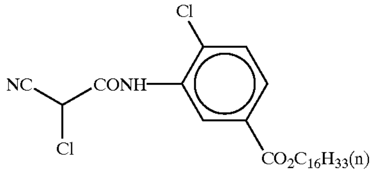
(C-60)
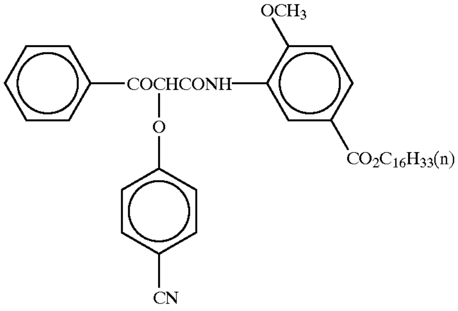
(C-61)
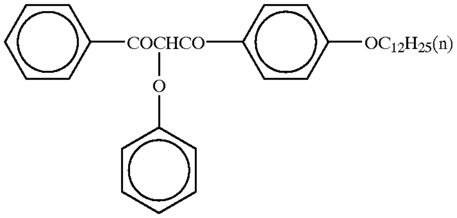
(C-62)
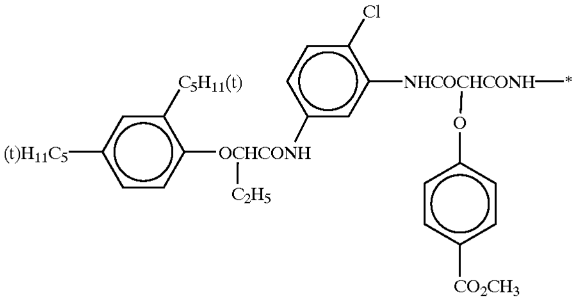
(C-63)
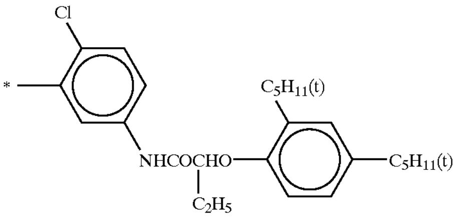
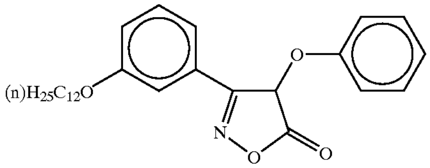

The couplers for use in the present invention may be added to any layer, but they are preferably added to layers containing a silver halide emulsion. Preferably the couplers for use in the present invention are added such that, with respect to emulsions different in light sensitivity, the dyes that will be produced have the relation of complementary colors to the colors of lights to which the silver halides are sensitive. For example, a yellow coupler is preferably added to a layer containing a blue-sensitive silver halide emulsion, a magenta coupler is preferably added to a layer containing a green-sensitive silver halide emulsion, and a cyan coupler is preferably added to a layer containing a red-sensitive silver halide emulsion. However, for example, when the light-sensitive material of the present invention is subjected to laser exposure, it is not important for the couplers to be added in a relation of complementary colors to the colors to which the silver halides are sensitive, as described above, and the couplers may be added without a relation of complementary colors; for example, a yellow coupler may be added to a layer containing a green-sensitive silver halide emulsion, a magenta coupler may be added to a layer containing a red-sensitive silver halide emulsion, and a cyan coupler may be added to a layer containing an infrared-sensitive silver halide emulsion.

As the yellow coupler, preferably a coupler of the active methylene type is used. As the magenta coupler, preferably a coupler of the pyrazolone type or the pyrazoloazole type is used, and particularly preferably a pyrazoloazole-type coupler is used. As the cyan coupler, preferably a phenol coupler, a naphthol coupler, and a pyrrolotriazole coupler are used, and particularly preferably a phenol coupler and a pyrrolotriazole coupler are used.

In the present invention, the color-developing agent precursor is preferably used in an amount of 0.01 mmol/$m^2$ to 10 mmol/$m^2$ per one color-forming layer, in order to obtain satisfactory color density. More preferably the amount to be used is 0.05 mmol/$m^2$ to 5 mmol/$m^2$, and particularly preferably 0.1 mmol/$m^2$ to 1 mmol/$m^2$. This range of amount is preferable in order to obtain satisfactory color density.

A preferable amount of the coupler to be used in the color-forming layer in which the color-developing agent precursor according to the present invention is used, is preferably 0.05 to 20 times, more preferably 0.1 to 10 times, and particularly preferably 0.2 to 5 times, the amount of the color-developing agent precursor in terms of mol. This range of amount is preferable in order to obtain satisfactory color density.

The color light-sensitive material of the present invention basically comprises photographic constitutional layers including at least one hydrophilic colloidal layer coated on a support; and a light-sensitive silver halide, a dye-forming coupler, and a color-developing agent precursor are contained in one or more photographic constitutional layers.

The dye-forming coupler and the color-developing agent precursors used in the present invention are added to an identical layer, in the most typical embodiment, but they can be added divisionally into separate layers, as long as they can react with each other. These ingredients are preferably added to a silver halide emulsion layer or a layer adjacent therewith in the light-sensitive material, and particularly preferably they are added together to an identical silver halide emulsion layer.

The color-developing agent precursor and coupler for use in the present invention can be introduced into the light-sensitive material by various known dispersion methods. Preferably the oil-in-water dispersion method is used, in which they are dissolved in a high-boiling organic solvent (and, if necessary, together with a low-boiling organic solvent), the solution is emulsified and dispersed in an aqueous gelatin solution, and the emulsified dispersion is added to a silver halide emulsion. The high-boiling organic solvent to be used in the present invention can be a compound nonmiscible with water, and having a melting point of 100° C. or below and a boiling point of 140° C. or higher, that is a good solvent for the color-developing agent precursors and couplers. The melting point of the high-boiling organic solvent is preferably 80° C. or below. The boiling point of the high-boiling organic solvent is preferably 160° C. or over, and more preferably 170° C. or over. Details of these high-boiling organic solvents are described in JP-A-62-215272, page 137, right lower column, to page 144, right upper column. In the present invention, when the high-boiling organic solvent is used, the amount of the high-boiling organic solvent to be used may be any amount, but preferably the amount is such that the weight ratio of the high-boiling organic solvent to the color-developing agent precursor (color-forming reducing agent) is from 20 or less: 1, more preferably from 0.02 to 5:1, and particularly preferably from 0.2 to 4:1.

Further, in the present invention, known polymer dispersion methods can be used. Specific examples of steps, effects, and latexes for impregnation of the latex dispersion method, which is one polymer dispersion method, are described, for example, in U.S. Pat. No. 4,199,363, West Germany Patent Application (OLS) Nos. 2,541,274 and 2,541,230, JP-B-53-41091 ("JP-B" means examined Japanese patent publication), and EP-029104. As another method, a dispersion method using a water-insoluble and organic solvent-soluble polymer is described in WO-A-88/00723.

The average particle size of the lipophilic fine particles containing the color-developing agent precursor for use in the present invention is not particularly limited, but, in view of the color-forming property, the average particle size is preferably 0.05 to 0.3 μm, and more preferably 0.05 to 0.2 μm.

To make the average particle size of lipophilic fine particles small is generally accomplished, for example, by choosing a type of surface-active agent, by increasing the amount of the surface-active agent to be used, by elevating the viscosity of the hydrophilic colloid solution, by lowering the viscosity of the lipophilic organic layer, through use of an additional low-boiling organic solvent, by increasing the rotational frequency of the stirring blades of an emulsifying apparatus, to increase the shearing force, or by prolonging the emulsifying time.

The particle size of lipophilic fine particles can be measured by an apparatus, such as a Nanosizer (trade name, manufactured by British Coulter Co.).

In the light-sensitive material of the present invention, by adding an auxiliary developing agent and/or its precursor, the sensitivity can be rendered high and the initial development will be quickened, and therefore it is preferable to contain an auxiliary developing agent and/or its precursor.

As the auxiliary developing agent for use in the present invention, pyrazolidones, dihydroxybenzenes, reductones, or aminophenols can be used preferably, with pyrazolidones being used particularly preferably. Preferably that the diffusibility of these compounds in a hydrophilic colloidal layer is low, and, for example, the solubility to water (25° C.) is preferably 0.1% or below, more preferably 0.05% or below, and particularly preferably 0.01% or below.

The precursor of the auxiliary developing agent used in the present invention is a compound that is present stably in the light-sensitive material, but it rapidly releases the auxiliary developing agent after it has been processed by a processing solution. Also in a case of using the compound, preferably the diffusibility in the hydrophilic colloidal layer is low. For example, the solubility to water (25° C.) is preferably 0.1% or below, more preferably 0.05% or below, and particularly preferably 0.01% or below. There is no particular restriction on the solubility of the auxiliary developing agent released from the precursor, but preferably the solubility of the auxiliary developing agent itself is low.

The auxiliary developing agent precursor for use in the present invention is preferably represented by formula (A).

$$A—(L)_n—PUG \qquad \text{formula (A)}$$

A represents a blocking group whose bond to $(L)_n$—PUG will be split off at the time of development processing; L represents a linking group whose right bond (in the above formula (A), the bond between L and PUG) will be split off after the bond on the left of L (the bond between A and L) is split off; n is an integer of 0 to 3; and PUG represents an auxiliary developing agent.

As the auxiliary developing agent, an electron-releasing compound that follows the Kendall-Pelz rule, other than the compounds of p-phenylenediamines, is used, and preferably the above pyrazolidones are used.

As the blocking group represented by A, the following already known groups can be used: blocking groups described, for example, in U.S. Pat. No. 3,311,476, such as an acyl group and a sulfonyl group; blocking groups that use the reverse Michael reaction, as described, for example, in JP-A-59-105642; blocking groups that use the formation of quinone methide, or a compound similar to quinone methide, by intramolecular electron transfer, as described, for example, in JP-A-2-280140; blocking groups that use intramolecular nucleophilic substitution reaction, as described, for example, in JP-A-63-318555 (EP-A-0295729); blocking groups that use the addition reaction of a nucleophilic reagent to a conjugated unsaturated bond, as described, for example, in JP-A-4-186344; blocking groups that use the β-elimination reaction, as described, for example, in JP-A-62-163051; blocking groups that use the nucleophilic substitution reaction of diarylmethanes, as described in JP-A-61-188540; blocking groups that uses the Lossen rearrangement reaction, as described in JP-A-62-187850; blocking groups that use the reaction between the N-acylated product of thiazolidin-2-thion and an amine, as described in JP-A-62-147457; and blocking groups that have two electrophilic groups to react with a di-nucleophilic agent, as described in WO-A-93/03419.

The group represented by L in the compound represented by formula (A) may be any linking group that can be split off from the group represented by A, at the time of development processing, and that then can split $(L)_{n-1}$—PUG.

Specific examples of the auxiliary developing agent or its precursor is shown below, but the compound that can be used in the present invention is not limited to them.

(ETA-1)

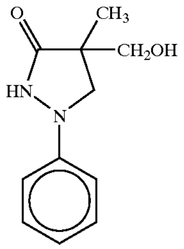

-continued (ETA-2)

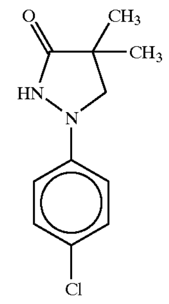

(ETA-3)

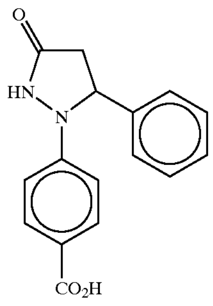

(ETA-4)

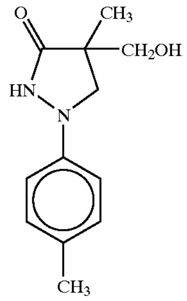

(ETA-5)

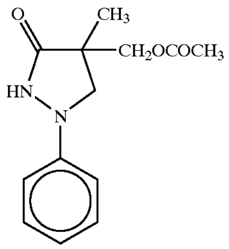

(ETA-6)

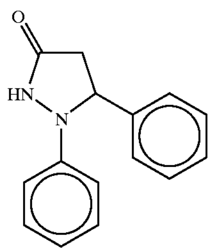

-continued
(ETA-7)
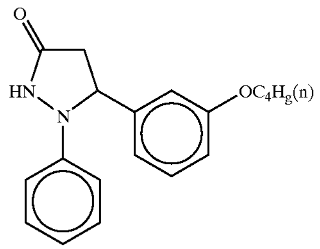
(ETA-8)
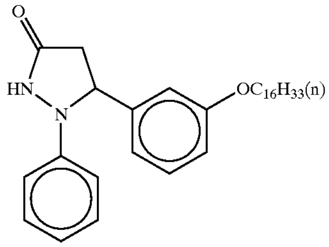
(ETA-9)
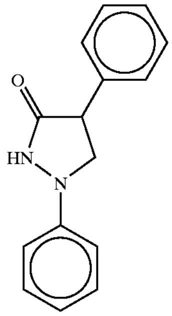
(ETA-10)
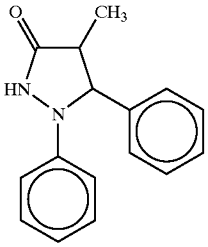
(ETA-11)
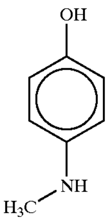
(ETA-12)
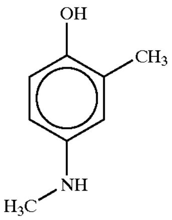
-continued
(ETA-13)
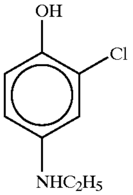
(ETA-14)
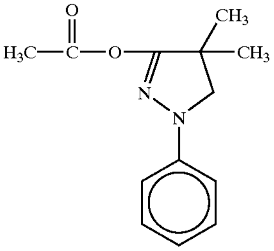
(ETA-15)
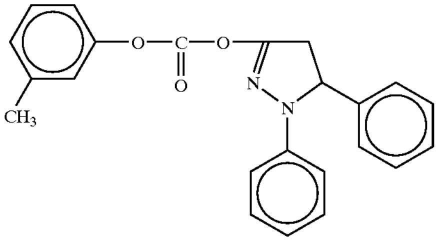
(ETA-16)
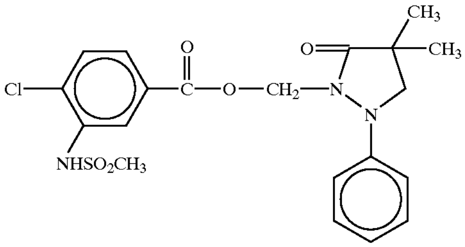
(ETA-17)
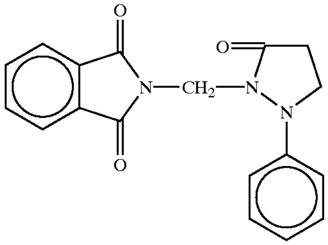
(ETA-18)
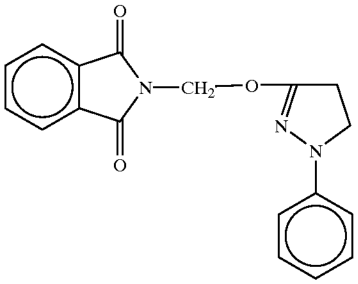

-continued (ETA-19)

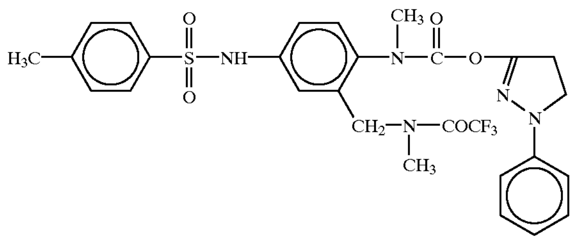

(ETA-20)

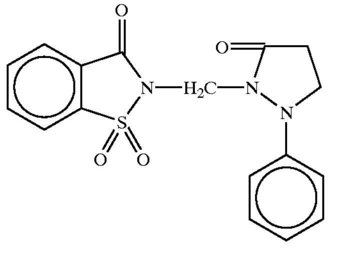

The above compound may be added to any of the light-sensitive layer, an intermediate layer, an undercoat layer, and a protective layer of a light-sensitive material, and preferably it is added to and used in a non-light-sensitive layer, when the auxiliary developing agent is contained in the light-sensitive material.

The methods of incorporating the compound into the light-sensitive material include, for example, a method of dissolving the compound in a water-miscible organic solvent, such as methanol, and directly adding this to a hydrophilic colloidal layer; a method of forming an aqueous solution or a colloidal dispersion of the compound, with a surface-active agent also contained, and adding the same; a method of dissolving the compound into a solvent or oil substantially immiscible with water, and then dispersing the solution into water or a hydrophilic colloid, and then adding the same; or a method of adding the compound, in a state of a dispersion of fine solid particles. The known methods may be applied singly or in combination. A method of preparing a dispersion of solid fine particles is described in detail on page 20 in JP-A-2-235044.

The amount of the compound to be added in a light sensitive material is generally 1 mol % to 200 mol %, preferably 5 mol % to 100 mol %, and more preferably 10 mol % to 50 mol %, based on the color-developing agent precursor.

As the support to be used in the present invention, any support can be used if it is a transmissible support or reflective support, on which a photographic emulsion layer can be coated, such as glass, paper, and plastic film. As the plastic film to be used in the present invention, for example, polyester films made, for example, of polyethylene terephthalates, polyethylene naphthalates, cellulose triacetate, or cellulose nitrate; polyamide films, polycarbonate films, and polystyrene films can be used.

"The reflective support" that can be used in the present invention refers to a support that increases the reflecting properties to make bright the dye image formed in the silver halide emulsion layer. Such a reflective support includes a support coated with a hydrophobic resin containing a light-reflecting substance, such as titanium oxide, zinc oxide, calcium oxide, and calcium sulfate, and a fluorescent whitening agent of a benzoxazole-series, cumarin-series, or pyrazoline-series, dispersed therein, or a support made of a hydrophobic resin itself containing a dispersed light-reflecting substance. Examples are a polyethylene-coated paper, a polyester-coated paper, a polypropylene-series synthetic paper, a support having a reflective layer or using a reflecting substance, such as a glass sheet; a polyester film made, for example, of a polyethylene terephthalate, cellulose triacetate, or cellulose nitrate; a polyamide film, a polycarbonate film, a polystyrene film, and a vinyl chloride resin. As the polyester-coated paper, particularly a polyester-coated paper whose major component is a polyethylene terephthalate, as described in EP-0 507 489, is preferably used.

The reflective support to be used in the present invention is preferably a paper support, both surfaces of which are coated with a water-resistant resin layer, and at least one of the water-resistant resin layers contains fine particles of a white pigment. Preferably the particles of a white pigment are contained in a density of 12% by weight or more, and more preferably 14% by weight or more. Preferably the light-reflecting white pigment is kneaded well in the presence of a surface-active agent, and the surface of the pigment particles is preferably treated with a dihydric to tetrehydric alcohol.

In the present invention, a support having the second kind diffuse reflective surface can also be used, preferably. "The second kind diffuse reflectivity" means diffuse reflectivity obtained by making a specular surface uneven, to form finely divided specular surfaces facing different directions. The unevenness of the second kind diffuse reflective surface has a three-dimensional average coarseness of generally 0.1 to 2 μm, and preferably 0.1 to 1.2 μm, for the center surface. Details about such a support are described in JP-A-2-239244.

In the light-sensitive material, photographic constitutional layers comprising the above photosensitive layers and various non-photosensitive layers, such as a protective layer, an underlayer, an intermediate layer, an antihalation layer, and a backing layer, can be provided. Further, in order to improve the color separation, various filter dyes can be added to the photographic constitutional layer.

As a binder or a protective colloid that can be used in the light-sensitive material according to the present invention, a gelatin is advantageously used, and other hydrophilic colloids can be used alone or in combination with a gelatin. The calcium content of gelatin is preferably 800 ppm or less, and more preferably 200 ppm or less. The iron content of gelatin is preferably 5 ppm or less, and more preferably 3 ppm or less. Further, in order to prevent the proliferation of various molds and bacteria that will proliferate in a hydrophilic colloid layer to deteriorate an image, preferably mildew-proofing agents, as described in JP-A-63-271247, are added.

The silver halide grains used in the present invention are made of silver bromide, silver chloride, silver iodide, silver chlorobromide, silver chloroiodide, silver iodobromide, or silver chloroiodobromide. Other silver salts, such as silver rhodanate, silver sulfide, silver selenide, silver carbonate, silver phosphate, or a silver salt of an organic acid, may be contained in the form of independent grains or as part of silver halide grains. If it is desired to make the development/desilvering (bleaching, fixing, and bleach-fix) step rapid, a so-called high-silver-chloride grains having the silver chloride content of 90 mol % or more are desirable. Further, if the development is to be restrained moderately, it is preferable to contain silver iodide. The preferable silver iodide content varies depending on the intended light-sensitive material.

In the high-silver-chloride emulsion used in the present invention, preferably there is provided a silver bromide localized phase having a layered structure or a non-layered structure in each silver halide grain and/or on each silver halide grain surface. The halogen composition of the localized phase has a silver bromide content of preferably at least 10 mol %, and more preferably over 20 mol %. Silver bromide contents of silver bromide localized phase can be analyzed by using a method such as X-ray diffraction (described in such books as "Shin-jikken Kagaku-koza 6/Kozo Kaiseki", edited by Nohonkagakukai, Maruzen). Further, these localized phase can be formed in the grain, at the edges, corners, or planes of surface of grain, as one of preferable examples, a phase which formed epitaxially on a corner of grain can be mentioned.

Further, for the purpose of lowering the replenishing rate of the development processing solution, it is also effective to increase the silver chloride content of the silver halide emulsion further. In such a case, an emulsion of almost pure silver chloride, having a silver chloride content, for example, of 98 to 100 mol %, is also preferably used.

The grains of the silver halide emulsion for use in the present invention preferably have a distribution or a structure with respect to the halogen composition. Typical examples thereof are disclosed in JP-B-43-13162 and in JP-A-61-215540, 60-222845, 60-143331, 61-75337, and 60-222844.

In order to make the inside of grains have a structure, not only the enclosing structure, as mentioned above, but also a so-call junctioned structure can be used to form grains. Examples thereof are disclosed, for example, in JP-A-59-133540 and 58-108526, EP-A-199 290 (A2), JP-B-58-24772, and JP-A-59-16254.

In the case of a Functioned structure, not only a combination of silver halides but also a combination of a silver halide with a silver salt compound having no rock salt structure, such as silver rhodanate and silver carbonate, can be used for the junctioned structure.

In the case of grains of silver iodobromide or the like having these structures, a preferable mode is that the core part is higher in silver iodide content than the shell part. Reversely, in some cases, grains having a lower silver iodide content in the core part than in the shell part are preferable. Similarly, in the case of grains having a junctioned structure, the silver iodide content of the host crystals is relatively higher than that of the junctioned crystals, or this may be reversed. The boundary part of the grains having these structures in which different halogen compositions are present, may be distinct or indistinct. Also preferable is a mode wherein the composition is continuously changed positively.

It is important that in the case of that two or more silver halides are present as mixed crystals, or as silver halide grains having structures, the halogen composition distribution between grains is controlled.

The method of measuring the halogen composition distribution between grains is described in JP-A-60 -254032. In particular, a highly uniform emulsion having a deviation coefficient of the halogen composition distribution of 20% or below is preferable.

It is important to control the silver halide composition near the surface of grains. An increase in the silver iodide content or the silver chloride content at the part near the surface changes the adsorption of a dye or the developing speed. Therefore the silver halide composition can be chosen in accordance with the purpose.

In the silver halide grains used in the present invention, in accordance with the purpose, any of regular crystals having no twin plane, and those described in "Shashin Kogyo no Kiso, Ginen Shashin-hen", edited by Nihon Shashin-gakkai (Corona Co.), page 163 (1979), such as single twins having one twin plane, parallel multiple twins having two or more parallel twin planes, and nonparallel multiple twins having two or more nonparallel twin planes, can be chosen and used. An example in which grains different in shape are mixed is disclosed in U.S. Pat. No. 4,865,964, and if necessary this method can be chosen. In the case of regular crystals, cubes having (100) planes, octahedrons having (111) planes, and dodecahedral grains having (110) planes, as disclosed in JP-B-55-42737 and JP-A-60-222842, can be used. Further, (hlm) plane grains as reported in "Journal of Imaging Science", Vol. 30, page 247 (1986), can be chosen and used in accordance with the purpose. Grains having two or more planes in one grain, such as tetradecahedral grains having (100) and (111) planes in one grain, grains having (100) and (110) planes in one grain, or grains having (111) and (110) planes in one grain, can be chosen and used in accordance with the purpose.

The value obtained by dividing the diameter of the projected area, which is assumed to be a circle, by the thickness of the grain, is called an aspect ratio, which defines the shape of tabular grains. Tabular grains having an aspect ratio grater than 1 can be used in the present invention. Tabular grains can be prepared by methods described, for example, by Cleave in "Photography Theory and Practice" (1930), page 131; by Gutof in "Photographic Science and Engineering", Vol. 14, pages 248 to 257 (1970); and in U.S. Pat. Nos. 4,434,226, 4,414,310, 4,433,048, and 4,439,520, and GB-2,112,157. When tabular grains are used, such merits are obtained that the covering power is increased and the color sensitization efficiency due to a sensitizing dye is increased, as described in detail in the above-mentioned U.S. Pat. No. 4,434,226. The average aspect ratio of 80% or more of all the projected areas of grains is desirably 1 or more but less than 100, more preferably 2 or more but less than 20, and particularly preferably 3 or more but less than 10. As the shape of tabular grains, a triangle, a hexagon, a circle, and the like can be chosen. A regular hexagonal shape having six approximately equal sides, described in U.S. Pat. No. 4,797,354, is a preferable mode.

In many cases, the grain size of tabular grains is expressed by the diameter of the projected area assumed to be a circle, and grains having an average diameter of 0.6 microns or below, as described in U.S. Pat. No. 4,748,106, are preferable, because the quality of the image is made high. An emulsion having a narrow grain size distribution, as described in U.S. Pat. No. 4,775,617, is also preferable. It is preferable to restrict the shape of tabular grains so that the thickness of the grains may be 0.5 microns or below, and more preferably 0.3 microns or below, because the sharpness is increased. Further, an emulsion in which the grains are highly uniform in thickness, with the deviation coefficient of grain thickness being 30% or below, is also preferable. Grains in which the thickness of the grains and the plane distance between twin planes are defined, as described in JP-A-63-163451, are also preferable.

In accordance with the purpose, it is preferable to choose grains having no dislocation lines, grains having several dislocation lines, or grains having many dislocation lines. Dislocation introduced straight in a special direction in the crystal orientation of grains, or curved dislocation, can be chosen, and it is possible to choose from, for example, dislocation introduced throughout grains, and dislocation introduced in a particular part of grains, such as dislocation introduced limitedly to the fringes of grains. In addition to the case of introduction of dislocation lines into tabular grains, also preferable is the case of introduction of dislocation lines into regular crystalline grains or irregular grains, represented by potato grains.

The silver halide emulsion used in the present invention may be subjected to a processing for making grains round, as disclosed, for example, in EP-B-96 727 (B1) and 64 412 (B1), or it may be improved in the surface, as disclosed in West Germany Patent No. 2,306,447C2 and JP-A-60-221320.

Generally, the grain surface has a flat structure, but it is also preferable in some cases to make the grain surface uneven intentionally. Examples are described in JP-A-58-106532, 60-221320, and U.S. Pat. No. 4,643,966.

The grain size of the emulsion used in the present invention is evaluated, for example, by the diameter of the projected area equivalent to a circle (the diameter of a circle assuming the projected area to be the circle) using an electron microscope; by the diameter of the grain volume equivalent to a sphere, calculated from the projected area and the grain thickness; or by the diameter of a volume equivalent to a sphere, using the Coulter Counter method. A selection can be made from ultrafine grains having a sphere-equivalent diameter (the diameter of a sphere assuming the grain volume to be a sphere) of 0.01 μm or below, and coarse grains having a sphere-equivalent diameter of 10 μm or more. Preferably grains of 0.1 μm or more but 3 μm or below are used as photosensitive silver halide grains.

As the emulsion used in the present invention, an emulsion having a wide grain size distribution, that is, a so-called polydisperse emulsion, or an emulsion having a narrow grain size distribution, that is, a so-called monodisperse emulsion, can be chosen and used in accordance with the purpose. As the scale for representing the size distribution, the diameter of the projected area of the grain equivalent to a circle, or the deviation coefficient of the sphere-equivalent diameters, is used. If a monodisperse emulsion is used, it is suitable to use an emulsion having such a size distribution that the deviation coefficient is generally 25% or below, more preferably 20% or below, and further more preferably 15% or below.

Further, in order to allow the photographic material to satisfy the intended gradation, in an emulsion layer having substantially the same color sensitivity, two or more monodisperse silver halide emulsions different in grain size are mixed and applied to the same layer or are applied as overlaid layers. Further, two or more polydisperse silver halide emulsions can be used as a mixture; or they can be used to form overlaid layers; or a combination of a monodisperse emulsion and a polydisperse emulsion can be used as a mixture; or the combination can be used to form overlaid layers.

The photographic emulsion used in the present invention can be prepared by a method described, for example, by P. Glafkides in "Chemie et Phisique Photographique," Paul Montel, 1967; by G. F. Duffin in "Photographic Emulsion Chemistry," Focal Press, 1966; or by V. L. Zelikman et al. in "Making and Coating Photographic Emulsion," Focal Press, 1964. A method wherein grains are formed in the presence of excess silver ions (the so-called reverse precipitation process) can also be used. As one type of the double-jet method, a method wherein pAg in the liquid phase, in which a silver halide will be formed, is kept constant, that is, the so-called controlled double-jet method, can also be used. According to this method,. a silver halide emulsion wherein the crystals are regular in shape and whose grain size is approximately uniform, can be obtained.

A method in which previously precipitated and formed silver halide grains are added to a reaction vessel for the preparation of an emulsion, and the methods described, for example, in U.S. Pat. Nos. 4,334,012, 4,301,241, and 4,150,994, are preferable in some cases. These can be used as seed crystals, or they are effective when they are supplied as a silver halide for growth. Further, in some cases, it is also effective to add fine grains having different halogen compositions in order to modify the surface.

The method in which a large part or only a small part of the halogen composition of silver halide grains is converted by the halogen conversion method is disclosed, for example, in U.S. Pat. Nos. 3,477,852 and 4,142,900, EP-B-273,429 and 273,430, and West German Publication Patent No. 3,819,241. To convert to a more hardly soluble silver salt, it is possible to add a solution of a soluble halogen or to add silver halide grains.

In addition to the method in which the grain growth is made by adding a soluble silver salt and a halogen salt at constant concentrations and at constant flow rates, grain formation methods wherein the concentration is changed or the flow rate is changed, as described in GB-1,469,480 and U.S. Pat. Nos. 3,650,757 and 4,242,445, are preferable methods. By increasing the concentration or increasing the flow rate, the amount of the silver halide to be supplied can be changed as a linear function, a quadratic function, or a more complex function, of the addition time.

A mixing vessel that is used when a solution of a soluble silver salt and a solution of a soluble halogen salt are reacted can be selected for use from methods described in U.S. Pat. Nos. 2,996,287, 3,342,605, 3,415,650, and 3,785,777, and West German Publication Patent Nos. 2,556,885 and 2,555,364.

For the purpose of promoting the ripening, a silver halide solvent is useful. For example, it is known to allow an excess amount of halide ions to be present in the reaction vessel, to promote the ripening. Further, another ripening agent can also be used. All of the amount of these ripening agents may be blended in the dispersion medium in the reaction vessel before silver salt and halide salt are added, or their introduction into the reaction vessel may be carried out together with the addition of a halide salt, a silver salt, or a peptizer.

As examples of these, ammonia, thiocyanates (e.g. potassium rhodanate and ammonium rhodanate), organic thioether compounds (e.g. compounds described, for example, in U.S. Pat. Nos. 3,574,628, 3,021,215, 3,057,724, 3,038,805, 4,276,374, 4,297,439, 3,704,130, and 4,782,013, and JP-A-57-104926), thion compounds (e.g. tetra-substituted thioureas described, for example, in JP-A-53-82408 and 55-77737, and U.S. Pat. No. 4,221,863; and compounds described in JP-A-53-144319), mercapto compounds capable of promoting the growth of silver halide grains, as described in JP-A-57-202531, and amine compounds (e.g. described in JP-A-54-100717), can be mentioned.

As a protective colloid and as a binder of other hydrophilic colloid layers that are used when the emulsion according to the present invention is prepared, gelatin is used advantageously, but another hydrophilic colloid can also be used.

Use can be made of, for example, a gelatin derivative, a graft polymer of gelatin with another polymer, a protein, such as albumin and casein; a cellulose derivative, such as hydroxyethylcellulose, carboxymethylcellulose, and cellulose sulfate ester; sodium alginate, a saccharide derivative, such as a starch derivative; and many synthetic hydrophilic polymers, including homopolymers and copolymers, such as a polyvinyl alcohol, a polyvinyl alcohol partial acetal, a poly-N-vinylpyrrolidone, a polyacrylic acid, a polymethacrylic acid, a polyacrylamide, a polyvinylimidazole, and a polyvinylpyrazole.

As the gelatin, in addition to lime-processed gelatin, acid-processed gelatin, and enzyme-processed gelatin described in Bull. Soc. Sci. Photo. Japan, No. 16, page 30 (1966), may also be used, and a hydrolyzate or enzymolyzate of gelatin can also be used. For the preparation of tabular grains, it is preferable to use a low-molecular-weight gelatin described in JP-A-1-158426.

Preferably, the silver halide emulsion according to the present invention is washed with water for desalting and is dispersed in a freshly prepared protective colloid. The temperature at which the washing with water is carried out can be selected in accordance with the purpose, and preferably the temperature is selected in the range of 5 to 50° C. The pH at which the washing is carried out can be selected in accordance with the purpose, and preferably the pH is selected in the range of 2 to 10, and more preferably in the range of 3 to 8. The pAg at which the washing is carried out can be selected in accordance with the purpose, and preferably the pAg is selected in the range of 5 to 10. As a method of washing with water, one can be selected from the noodle washing method, the dialysis method using a diaphragm, the centrifugation method, the coagulation settling method, and the ion exchange method. In the case of the coagulation settling method, selection can be made from, for example, the method wherein sulfuric acid salt is used, the method wherein an organic solvent is used, the method wherein a water-soluble polymer is used, and the method wherein a gelatin derivative is used.

When the silver halide emulsion is prepared, in accordance with the purpose, it is preferable to allow a salt of a metal ion to be present, for example, at the time when grains are formed, in the step of desalting, at the time when the chemical sensitization is carried out, or before the application. When the grains are doped, the addition is preferably carried out at the time when the grains are formed; or after the formation of the grains but before the completion of the chemical sensitization, when the surface of the grains is modified or when the salt of a metal ion is used as a chemical sensitizer. As to the doping of grains, selection can be made from a case in which the whole grains are doped, one in which only the core parts of the grains are doped, one in which only the shell parts of the grains are doped, one in which only the epitaxial parts of the grains are doped, and one in which only the substrate grains are doped. For example, Mg, Ca, Sr, Ba, Al, Sc, Y, La, Cr, Mn, Fe, Co, Ni, Cu, Zn, Ga, Ru, Rh, Pd, Re, Os, Ir, Pt, Au, Cd, Hg, Tl, In, Sn, Pb, and Bi can be used. These metals can be added if they are in the form of a salt that is soluble at the time when grains are formed, such as an ammonium salt, an acetate, a nitrate, a sulfate, a phosphate, a hydroxide, a six-coordinate complex, and a four-coordinate complex. Examples include $CdBr_2$, $CdCl_2$, $Cd(NO_3)_2$, $Pd(NO_3)_2$, $Pb(CH_3COO)_2$, $K_3[Fe(CN)_6]$, $(NH_4)_4[Fe(CN)_6]$, $K_3IrCl_6$, $(NH_4)_3RhCl_6$, and $K_4Ru(CN)_6$. As a ligand of the coordination compound, one can be preferably selected from halo, aquo, cyano, cyanate, thiocyanate, nitrosyl, thionitrosyl, oxo, and carbonyl. With respect to these metal compounds, only one can be used, but two or more can also be used in combination. In some cases, a method wherein a chalcogen compound is added during the preparation of the emulsion, as described in U.S. Pat. No. 3,772,031, is also useful. In addition to S, Se, and Te, a cyanate, a thiocyanate, a selenocyanate, a carbonate, a phosphate, or an acetate may be present.

The silver halide grains for use in the present invention can be subjected to at least one of sulfur sensitization, selenium sensitization, tellurium sensitization (these three are called chalcogen sensitization, collectively), noble metal sensitization, and reduction sensitization, in any step of the production for the silver halide emulsion. A combination of two or more sensitizations is preferable. Various types of emulsions can be produced, depending on the steps in which the chemical sensitization is carried out. There are a type wherein chemical sensitizing nuclei are embedded in grains, a type wherein chemical sensitizing nuclei are embedded at parts near the surface of grains, and a type wherein chemical sensitizing nuclei are formed on the surface. In the emulsion for use in the present invention, the location at which chemical sensitizing nuclei are situated can be selected in accordance with the purpose.

Chemical sensitizations that can be carried out preferably in the present invention are chalcogen sensitization and noble metal sensitization, which may be used singly or in combination; and the chemical sensitization can be carried out by using active gelatin, as described by T. H. James in "The Theory of the Photographic Process," 4th edition, Macmillan, 1997, pages 67 to 76, or by using sulfur, selenium, tellurium, gold, platinum, palladium, or iridium, or a combination of these sensitizing agents, at a pAg of 5 to 10, a pH of 5 to 8, and a temperature of 30 to 80° C., as described in Research Disclosure, Item 12008 (April 1974); Research Disclosure, Item 13452 (June 1975); Research Disclosure, Item 307105 (November 1989); U.S. Pat. Nos. 2,642,361, 3,297,446, 3,772,031, 3,857,711, 3,901,714, 4,266,018, and 3,904,415, and GB-1,315,755.

In the sulfur sensitization, an unstable sulfur compound is used, and specifically, thiosulfates (e.g. hypo), thioureas (e.g. diphenylthiourea, triethylthiourea, and allylthiourea), rhodanines, mercaptos, thioamides, thiohydantoins, 4-oxo-oxazolidin-2-thions, di- or poly-sulfides, polythionic acids, and elemental sulfur, and known sulfur-containing compounds as described in U.S. Pat. Nos. 3,857,711, 4,266,018, and 4,054,457 can be used. In many cases, sulfur sensitization is used in combination with noble metal sensitization.

A preferable amount of a sulfur sensitizing agent used for the silver halide grains according to the present invention is $1\times10^{-7}$ to $1\times10^{-3}$ mol, and more preferably $5\times10^{-7}$ to $1\times10^{-4}$ mol, per mol of the silver halide.

In the selenium sensitization, known unstable selenium compounds are used, such as those described, for example, in U.S. Pat. Nos. 3,297,446 and 3,297,447, specific such selenium compounds are colloidal metal selenium, selenoureas (e.g. N,N-dimethylselenourea and tetramethylselenourea), selenoketones (e.g. selenoacetone), selenoamides (e.g. selenoacetamide), selenocarboxylic acids and esters, isoselenocyanates, selenides (e.g. diethylselenides and triphenylphosphine selenide), and selenophosphates (e.g. tri-p-tolylselenophosphate). In some cases, preferably the selenium sensitization is used in combination with one or both of sulfur sensitization and noble metal sensitization.

The amount of the selenium sensitizing agent to be used varies depending on the selenium compound, the silver halide grains, the chemical ripening conditions, and the like that are used, and the amount is generally of the order of $10^{-8}$ to $10^{-4}$ mol, and preferably $10^{-7}$ to $10^{-5}$ mol, per mol of the silver halide.

As the tellurium sensitizing agent used in the present invention, compounds described in CA-800 958, GB-1 295 462 and 1 396 696, and JP-A-2-333819 and 3-131598 can be used.

In the noble metal sensitization, a salt of a noble metal, such as gold, platinum, palladium, and iridium, can be used, and specifically gold sensitization, palladium sensitization, and a combination thereof are particularly preferable. In the case of gold sensitization, a known compound, such as chloroauric acid, potassium chloroaurate, potassium auriothiocyanate, gold sulfide, and gold selenide, can be used. The palladium compound means salts of divalent or tetravalent palladium salt. A preferable palladium compound is represented by $R_2PdX_6$ or $R_2PdX_4$, wherein R represents a hydrogen atom, an alkali metal atom, or an ammonium group; and X represents a halogen atom, i.e. a chlorine atom, a bromine atom, or an iodine atom.

Specifically, $K_2PdCl_4$, $(NH_4)_2PdCl_6$, $Na_2PdCl_4$, $(NH_4)_2PdCl_4$, $Li_2PdCl_4$, $Na_2PdCl_6$, or $K_2PdBr_4$ is preferable. Preferably a gold compound and a palladium compound are used in combination with a thiocyanate or a selenocyanate.

Preferably the emulsion that can be used in the present invention is used in combination with gold sensitization. A preferable amount of the gold sensitizing agent is $1\times10^{-7}$ to $1\times10^{-3}$ mol, and more preferably $5\times10^{-7}$ to $5\times10^{-4}$ mol, per mol of the silver halide. A preferable amount of the palladium compound is in the range of $5\times10^{-7}$ to $1\times10^{-3}$ mol. per mol of the silver halide. A preferable amount of the thiocyan compound and the selenocyan compound is in the range of $1\times10^{-6}$ to $5\times10^{-2}$ mol, per mol of the silver halide.

Preferably that the silver halide emulsion according to the present invention is subjected to reduction sensitization during the formation of the grains, after the formation of the grains but before the chemical sensitization, or during or after the chemical sensitization.

Herein, the reduction sensitization can be selected from a method wherein a reduction sensitizer is added to a silver halide emulsion; a method called silver ripening, wherein the growth or ripening is made in an atmosphere having a pAg as low as 1 to 7; and a method called high-pH ripening, wherein the growth or ripening is made in an atmosphere having a pH as high as 8 to 11. Two or more methods can also be used in combination.

As the reduction sensitizer, known reduction sensitizers can be selected and used, such as stannous salts, ascorbic acid and its derivatives, amines and polyamines, hydrazine and its derivatives, formamidinesufinic acid, sillane compounds, and boran compounds; and two or more compounds can be used in combination. As the reduction sensitizer, preferable compounds are stannous chloride, aminoiminomethanesulfinic acid (popularly called thiourea dioxide), dimethylamineboran, and ascorbic acid and its derivatives.

The chemical sensitization can be carried out in the presence of a so-called chemical sensitization auxiliary. As a useful chemical sensitization auxiliary, a compound is used that is known to suppress fogging and to increase the sensitivity in the process of chemical sensitization, such as azaindenes, azapyridazines, and azapyrimidines. Examples of the chemical sensitization auxiliary are described in U.S. Pat. Nos. 2,131,038, 3,411,914, and 3,554,757, JP-A-58-126526, and by G. F. Duffin in "Photographic Emulsion Chemistry" mentioned above, pages 138 to 143.

Preferably an oxidizing agent for silver is added during the process of the production of the emulsion according to the present invention. The oxidizing agent for silver refers to a compound that acts on metal silver to convert it to silver ions. Particularly useful is a compound that converts quite fine silver grains, which are concomitantly produced during the formation of silver halide grains and during the chemical sensitization, to silver ions. The thus produced silver ions may form a silver salt that is hardly soluble in water, such as a silver halide, silver sulfide, and silver selenide, or they may form a silver salt that is readily soluble in water, such as silver nitrate. The oxidizing agent for silver may be inorganic or organic. Example inorganic oxidizing agents include ozone, hydrogen peroxide and its adducts (e.g. $NaBO_2.H_2O_2.3H_2O$, $2NaCO_3.3H_2O_2$, $Na_4P_2O_7.2H_2O_2$, and $2Na_2SO_4.H_2O_2.2H_2O$); oxygen acid salts such as peroxyacid salts (e.g. $K_2S_2O_8$, $K_2C_2O_6$, and $K_2P_2O_8$), peroxycomplex compounds (e.g. $K_2[Ti(O_2)C_2O_4].3H_2O$, $4K_2SO_4.Ti(O_2)OH.SO_4.2H_2O$, and $Na_3[VO(O_2)(C_2H_4)_2].6H_2O$), permanganates (e.g. $KMnO_4$), and chromates (e.g. $K_2Cr_2O_7$); halogen elements, such as iodine and bromine; perhalates (e.g. potassium periodate), salts of metals having higher valences (e.g. potassium hexacyanoferrate (III), and thiosulfonates.

Examples of the organic oxidizing agents include quinones, such as p-quinone; organic peroxides, such as peracetic acid and perbenzoic acid; and compounds that can release active halogen (e.g. N-bromosuccinimido, chloramine T, and chloramine B).

It is a preferably mode that the above-described reduction sensitization and the oxidizing agent for silver are used in combination.

In the photographic emulsion used in the present invention, various compounds can be incorporated for the purpose of preventing fogging during the process of the production of the photographic material, during the storage of the photographic material, or during the photographic processing, or for the purpose of stabilizing the photographic performance. That is, various compounds known as antifoggants or stabilizers can be added, such as thiazoles including benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (e.g., 1-phenyl-5-mercaptotetrazole and 1-(5-methylureidphenyl)-5-mercaptotetrazole); mercaptopyrimidines; mercaptotriazines; thioketo compounds, such as oxazolinthione; and azaindenes, such as triazaindenes, tetraazaindenes (particularly 4-hydroxy-6-methyl(1,3,3a,7)tetraazaindenes), and pentaazaindenes. For examples, those described in U.S. Pat. Nos. 3,954,474 and 3,982,947, and JP-B-62-28660, can be used. A preferable compound is a compound described in JP-A-63-212932. These antifoggants and stabiliziers can be added, in accordance with the purpose, at various steps of before, during or after the grain formation, during the washing step, during the dispersing after washing, before, during or after the chemical sensitization, or before the applying.

The photographic emulsion to be used in the present invention is generally sensitized with methine dyes and the like. Dyes that can be used include a cyanine dye, a merocyanine dye, a composite cyanin dye, a composite merocyanine dye, a halopolar cyanine dye, a hemicyanine dye, a styryl dye, and a hemioxonol dye. Particularly useful dyes are those belonging to a cyanine dye, a merocyanine dye, and a composite merocyanine dye. In these dyes, any of nuclei generally used in cyanine dyes as basic heterocyclic nuclei can be applied. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, and a pyridine nucleus; and a nucleus formed by fusing an cycloaliphatic hydrocarbon ring or an aromatic hydrocarbon ring to these nuclei, that is, such as an indolenine nucleus, a benzindolenine nucleus, an indole nucleus, a benzoxazole nucleus, a naphthooxazole nucleus, a benzothiazole nucleus, a naphthothiazole nucleus, a benzoselenazole nucleus, a benzimidazole nucleus, a quinoline nucleus, can be applied. These nuclei may be substituted on the carbon atom.

In the merocyanine dye or the composite merocyanine dye, as a nucleus having a ketomethylene structure, a 5- to 6-membered heterocyclic nucleus, such as a pyrazolin-5-one nucleus, a thiohydantoine nucleus, a 2-thiooxazolidin-2,4-dione nucleus, a thiazolidin-2,4-dione nucleus, a rhodanine nucleus, and a thiobarbituric acid nucleus, can be applied.

These sensitizing dyes can be used singly or in combination, and a combination of these sensitizing dyes is often used, particularly for the purpose of supersensitization. Typical examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862, and 4,026,707, GB-1,344,218 and 1,507,803, JP-B-43-4,936 and 53-12,375, and JP-A-52-110,618 and 52-109,925.

Together with the sensitizing dye, a dye having no spectral sensitizing action itself, or a substance that does not substantially absorb visible light and that exhibits supersensitization, may be included in the emulsion.

The timing when the sensitizing dye is added to the emulsion may be at any stage known to be useful in the preparation of emulsions. The addition is carried out most usually at a time after the completion of chemical sensitization and before coating, but it can be carried out at the same time as the addition of a chemical sensitizer, to carry out spectral sensitization and chemical sensitization simultaneously, as described in U.S. Pat. Nos. 3,628,969 and 4,225,666; it can be carried out prior to chemical sensitization, as described in JP-A-58-113928; or it can be carried out before the completion of the formation of the precipitate of silver halide grains to start spectral sensitization. Further, as taught in U.S. Pat. No. 4,255,666, these foregoing compounds may be added in portions, i.e., part of these compounds is added prior to chemical sensitization, and the rest is added after the chemical sensitization, and also the addition may be carried out at any time during the formation of silver halide grains, as disclosed, for example, in U.S. Pat. No. 4,183,756.

Generally the amount of the sensitizing dye to be added is of the order of $4\times10^{-6}$ to $8\times10^{-3}$ mol per mol of the silver halide, but when the silver halide grain size is 0.2 to 1.2 $\mu$m, which is more preferable, the amount of the sensitizing dye to be added is more effectively about $5\times10^{-5}$ to $2\times10^{-3}$ mol per mol of the silver halide.

To the photographic material for use in the present invention, may be added the above-mentioned various additives, and also other various additives in accordance with the purpose.

These additives are described in more detail in Research Disclosure, Item 17643 (December 1978); Research Disclosure, Item 18176 (November 1979); and Research Disclosure, Item 307105 (November 1989), and the particular parts are given below in a table.

| | Additive | RD 17643 | RD 18716 | RD 18716 |
|---|---|---|---|---|
| 1 | Chemical sensitizers | p. 23 | p. 648 (right column) | p. 996 |
| 2 | Sensitivity-enhancing agents | | p. 648 (right column) | — |
| 3 | Spectral sensitizers and Supersensitizers | pp. 23–24 | pp. 648 (right column) –649 (right column) | pp. 996 (right column) –998 (right column) |
| 4 | Brightening agents | p. 24 | — | p. 998 (right column) |
| 5 | Antifogging agents and Stabilizers | pp. 24–25 | p. 649 (right column) | pp. 998 (right column) –1000 (right column) |
| 6 | Light absorbers, Filter dyes, and UV Absorbers | pp. 25–26 | pp. 649 (right column) –650 (left column) | p. 1003 (left to right column) |
| 7 | Stain-preventing agents | p. 25 (right column) | p. 650 (left to right column) | — |
| 8 | Image dye stabilizers | p. 25 | — | — |
| 9 | Hardeners | p. 26 | p. 651 (left column) | pp. 1004 (right column) –1005 (left column) |
| 10 | Binders | p. 26 | p. 651 (left column) | pp. 1003 (right column) –1004 (right column) |
| 11 | Plasticizers and Lubricants | p. 27 | p. 650 (right column) | p. 1006 (left to right column) |
| 12 | Coating aids | pp. 26–27 | p. 650 (right column) | pp. 1005 (left column) –1006 (left column) |
| 13 | Antistatic agents | p. 27 | p. 650 (right column) | pp. 1006 (right column) –1007 (left column) |

The total coated amount of silver of the light-sensitive material of the present invention is preferably 0.003 to 12 g per $m^2$ in terms of silver. In the case of transmission-type materials, such as color negative films, that amount is preferably 1 to 12 g, and more preferably 3 to 10 g. In the case of reflection-type materials, such as color print papers, that amount is preferably 0.003 to 1 g, in view of rapid processing or lowering of the replenishing rate, and in that case the amount of addition in each light-sensitive layer is preferably 0.001 to 0.4 g.

In the present invention, if the coating amount of silver in each light-sensitive layer is too small, the dissolution of the silver salt proceeds, and therefore a satisfactory color density cannot be obtained.

The total amount of gelatin of the light-sensitive material of the present invention is generally 1.0 to 30 g, and preferably 2.0 to 20 g, per $m^2$. In the swelling of the light-sensitive material in an alkali solution having a pH of 12, the time for the swelled film thickness to reach ½ of its saturated swelled film thickness (90% of the maximum swelled thickness) is preferably 15 sec or less, and more preferably 10 sec or less. Further, the swelling rate [(maximum swelled film thickness−film thickness)/film thickness×100] is preferably 50 to 300%, and particularly preferably 100 to 200%.

As an anti-fungus agent and a mildew-proofing agent that can be used in the present invention, those described in JP-A-63-271247 are useful. As a hydrophilic colloid used in the photographic layers constituting the light-sensitive material, gelatin is preferable, and particularly, the content of heavy metals contained therein as impurities, such as iron, copper, zinc, and manganese, is preferably 5 ppm or less, and more preferably 3 ppm or less.

The light-sensitive material of the present invention is for use in not only printing systems that use usual negative printers, it is also suitable for scanning exposure systems using cathode rays (CRT).

In comparison with apparatuses using lasers, cathode ray tube exposure apparatuses are simple and compact and make the cost low. Further, the adjustment of optical axes and colors is easy.

For the cathode ray tubes used for image exposure, use is made of various emitters that emit light in spectral regions as required. For example, any one of, or a mixture of two or more of, a red-color emitter, a green-color emitter, and a blue-color emitter may be used. The spectral region is not limited to the above red, green, and blue, and an emitter that emits a color in the yellow, orange, purple, or infrared region may also be used. In particular, a cathode ray tube that emits white light by mixing these phosphors is often used.

When the light-sensitive material has multiple light-sensitive layers different in spectral sensitivity distributions, and the cathode ray tube has phosphors that show light emission in multiple spectral regions, multiple colors may be exposed at a time; namely, image signals of multiple colors are inputted into the cathode ray tube, to emit lights from the tube surface. A method in which exposure is made in such a manner that image signals for respective colors are inputted successively, to emit the respective colors successively, and they are passed through filters (films) for cutting out other colors (surface-successive exposure), may be employed, and generally the surface-successive exposure is preferred to make image quality high, since a high-resolution cathode ray tube can be used.

The light-sensitive material of the present invention is preferably used for digital scanning exposure system that uses monochromatic high-density light, such as a second harmonic generating light source (SHG) that comprises a combination of a nonlinear optical crystal with a semiconductor laser or a solid state laser using a semiconductor laser as an excitation light source, a gas laser, a light-emitting diode, or a semiconductor laser. To make the system compact and inexpensive, it is preferable to use a semiconductor laser or a second harmonic generating light source (SHG) that comprises a combination of a nonlinear optical crystal with a semiconductor laser or a solid state laser. Particularly, to design an apparatus that is compact, inexpensive, long in life, and high in stability, the use of a semiconductor laser is preferable.

If such a scanning exposure light source is used, the spectral sensitivity maximum wavelength of the light-sensitive material of the present invention can arbitrarily be set by the wavelength of the light source for the scanning exposure to be used. In an SHG light source obtained by combining a nonlinear optical crystal with a semiconductor laser or a solid state laser that uses a semiconductor laser as an excitation light source, since the emitting wavelength of the laser can be halved, blue light and green light can be obtained. Therefore, the spectral sensitivity maximum of the light-sensitive material can be present in each of the usual three wavelength regions, the blue region, the green region and the red region.

If the exposure time in this scanning exposure is defined as the time for which a picture element size is exposed to light with the density of the picture element being 400 dpi, preferably the exposure time is $10^{-4}$ sec or less, more preferably $10^{-6}$ sec or less. Particularly preferably, the exposure is carried out by scanning exposure, wherein the exposure time is $10^{-8}$ to $10^{-4}$ sec per picture element and adjacent rasters are overlapped, because improvement is made with respect to the reciprocity law failure.

Preferable scanning exposure systems that can be applied to the present invention are described in detail in the JP-A-7-104448, from line 6 on column 76 to line 41 on column 77.

As the image-forming method using the light-sensitive material having the color-developing agent precursor built therein of the present invention, there are an activator processing method, in which, after the exposure to light, development processing is carried out with an alkaline processing solution free from a color-developing agent; a method in which processing is carried out with a processing solution containing an auxiliary developing agent/a base; a method in which the above alkaline processing solution in the diffusion transfer process is developed and processed onto the light-sensitive material for the processing, and a method in which the processing is carried out by heat development. When activator processing is carried out, the light-sensitive material is subjected to activator development (color development), desilvering, and washing or stabilization processing.

By the term "activator processing" is meant a processing method in which a color-developing agent precursor is built into a light-sensitive material and the light-sensitive material is subjected to development processing with a processing solution free from a color-developing agent precursor. The present invention is characterized in that "the activator solution" is substantially free from any color-developing agent, and the activator solution may contain other components (e.g. an alkali, a halogen, and a chelating agent). Further, in some cases, preferably in order to keep the processing stability, a reducing agent is not contained, and in that case, preferably an auxiliary developing agent, hydroxylamines, sulfites, and the like are substantially not contained.

Herein, the term "substantially free from" means that in each case the content is preferably 0.5 mmol/liter or less, more preferably 0.1 mmol/liter or less, and particularly preferably zero (not contained at all). The pH of the alkaline processing solution (aqueous solution) is preferably 9 to 14, and particularly preferably 10 to 13.

With respect to light-sensitive materials for activator processing and their processing, those described, for example, in JP-A-8-234388, JP-A-7-334190, JP-A-7-334192, JP-A-7-334197, and JP-A-7-344396 can be applied, instead of a built-in-type hydrazine compound, by using the color-developing agent precursor for use in the present invention alone or in combination with the built-in-type hydrazine compound.

In the activator solution, halide ions, such as chloride ions, bromide ions, and iodide ions, can be contained, but they are preferably not contained therein. Herein the halide ions may be added directory to the activator solution, or they may be dissolved out from the photographic material into the activator solution during the development processing using the activator solution. The pH of the activator solution used in the present invention is preferably 8 to 13, and more preferably 9 to 12.

To retain a pH of the activator solution in the above range, it is preferable to use various buffers, such as carbonates, phosphates, tetraborates, and hydroxybenzoates. The amount of the buffer to be added to the activator solution is preferably 0.05 mol/liter or more, and particularly preferably 0.1 to 0.4 mol/liter.

In addition, in the activator solution, as a sediment-preventive agent against calcium and magnesium, or as an agent for stabilizing the activator solution, various chelating agents can be used. With respect to the amount of the chelating agent to be added, preferably the amount is enough to sequester the metal ions in the activator solution, and, for example, these chelating agents are used in an amount in the order of 0.1 to 10 g per liter.

In the present invention, if required, an arbitrary antifoggant can be added. As the antifoggant, nitrogen-containing heterocyclic compounds, and alkali metal halide, such as sodium chloride, potassium bromide, and potassium iodide, can be used. The amount of the nitrogen-containing heterocyclic compound to be added is generally $1\times10^{-5}$ to $1\times10^{-2}$ mol/liter, and preferably $2.5\times10^{-5}$ to $1\times10^{-3}$ mol/liter.

In the activator solution, if necessary, an arbitrary development accelerator can be added. Further, the activator solution preferably contains a fluorescent whitening agent, and particularly preferably 4,4'-diamino-2,2'-disulfostilbene-series compounds can be added.

The processing temperature of the activator solution to be applied to the present invention is generally 20 to 50° C., and preferably 30 to 45° C. The processing time is generally 5 sec to 2 min, and preferably 10 sec to 1 min. With respect to the replenishing rate, although a small amount is preferable, the replenishing rate is generally 15 to 600 ml, preferably 25 to 200 ml, and more preferably 35 to 100 ml, per $m^2$ of the photographic material.

After the development, a desilvering process can be carried out. The desilvering process comprises a fixing process, or both bleaching process and a fixing process. When both the bleaching and fixing processes are carried out, the bleaching process and the fixing process may be carried out separately or simultaneously (bleach-fix process). Also, according to the purpose, the processing may be carried out in a bleach-fix bath having two successive tanks; or the fixing process may be carried out before the bleach-fix process; or the bleaching process may be carried out after the bleach-fix process. Further, in some cases, it is preferable that after the development, the stabilizing process is carried out without desilvering, to stabilize a dye image and silver salts.

Example bleaching agents for use in the bleaching solution or the bleach-fix solution include, for example, compounds of polyvalent metals, such as iron(III), cobalt(III), chromium(IV), and copper(II); peracids; quinones; and nitro compounds. Among them, aminopolycarboxylic acid iron (III) of ethylenediaminetetraacetic acid iron(III) complex salt and 1,3-diaminopropanetetraacetic acid iron(III) complex salt, hydrogen peroxide, persulfates, and the like are preferred, in view of rapid processing and the prevention of environmental pollution.

The bleaching solution and bleach-fix solution that use these aminopolycarboxylic acid irons(III) complex salts are generally used at a pH of 3 to 8, and preferably 5 to 7. The bleaching solution that uses persulfates or hydrogen peroxide is generally used at a pH of 4 to 11, and preferably 5 to 10. In the bleaching solution, the bleach-fix solution, and the bath preceding them, if required, a bleach-accelerating agent can be used. In the bleaching solution, the bleach-fix solution, and the fixing solution, use can be made of known additives, such as a rehalogenating agent, a pH buffering agent, and a metal corrosion-preventive agent. In particular, it is preferable to contain an organic acid having an acid dissociation constant (pKa) of 2 to 7, to prevent bleach stain. Example fixing agents for use in the fixing solution and the bleach-fix solution include thiosulfates, thiocyanates, thioureas, a large amount of iodide salts, nitrogen-containing heterocyclic compounds, having a sulfide group, as described in JP-A-4-365037, pages 11 to 21, and JP-A-5-66540, pages 1088 to 1092; metho-ionic compounds, and thioether compounds.

Preferable preservatives for the fixing solution and the bleach-fix solution are sulfites, bisulfites, carbonylbisulfite abducts, and sulfinic acid compounds described in EP-A-294 769. In the fixing solution and the bleach-fix solution, further, for example, any of various fluorescent whitening agents, antifoaming agents, surface-active agents, polyvinylpyrolidones, and methanol can be contained.

The processing temperature of the desilvering step is generally 20 to 50° C., and preferably 30 to 45° C. The processing time is generally 5 sec to 2 min, and preferably 10 sec to 1 min. Although a small replenishing rate is preferable, the replenishing rate is generally 15 to 600 ml, preferably 25 to 200 ml, and more preferably 35 to 100 ml, per $m^2$ of the photographic material. The processing is also preferably carried out without replenishment in such a way that the evaporated amount is supplemented with water.

The light-sensitive material of the present invention, after being subjected to a desilvering process, is generally subjected to a washing step. If a stabilizing process is carried out, the washing process can be omitted. As the stabilizing process, any known processes described in JP-A-57-8543, 58-14834, 60-220345, JP-A-58-127926, 58-137837, and 58-140741 can be used. Also, a washing process/stabilizing process that uses, as a final bath, a stabilizing bath containing a dye stabilizing agent and a surface-active agent, which process is representatively used for processing photographing color light-sensitive materials, can be carried out.

In the washing water and the stabilizing solution, use can be made, for example, of a sulfite; a water softener, such as inorganic phosphoric acids, polyaminocarboxylic acids, and organic aminophosphonic acids; a metal salt, such as Mg salts, Al salts, and Bi salts; a surface-active agent; a hardener; a pH buffer; a fluorescent whitening agent; and a silver-salt-forming agent, such as nitrogen-containing heterocyclic compounds.

As the dye stabilizing agent in the stabilizing solution, aldehydes, such as formaldehyde and glutaraldehyde; N-methylol compounds, hexamethylenetetramine, or aldehyde sulfite adducts can be mentioned.

The pH of the washing water and the stabilizing solution is generally 4 to 9, and preferably 5 to 8. The processing temperature is generally 15 to 45° C., and preferably 25 to 40° C. The processing time is generally 5 sec to 2 min, and preferably 10 sec to 40 sec.

The overflow involved in the replenishment of the washing solution and/or the stabilizing solution can be used again in some other process, such as the desilvering process. The amount of the washing water and/or the stabilizing solution can be set in a wide range depending on various conditions, and the replenishing rate is preferably 15 to 360 ml, and more preferably 25 to 120 ml, per $m^2$ of the photographic material. To reduce the replenishing rate, it is preferable to use multiple tanks and a multi-stage countercurrent system.

In the present invention, in order to save water, water can be used that has been obtained by treating the overflow or the in-tank solution using a reverse osmosis membrane. For example, the treatment by reverse osmosis is preferably carried out for water from the second tank, or the more latter tank of the multi-stage countercurrent washing process and/or the stabilizing process.

In the present invention, preferably the stirring is intensified as much as possible. To intensify the stirring, specifically a method wherein a jet stream of a processing solution is caused to impinge on the emulsion surface of a photographic material, as described in JP-A-62-183460 and 62-183461; a method wherein a rotating means is used to increase the stirring effect, as described in JP-A-62-183461; a method wherein a photographic material is moved, with the emulsion surface of the material being in contact with a wiper blade provided in a solution, so that a turbulent flow may occur near the emulsion surface, to improve the stirring effect; and a method wherein the total amount of a processing solution to be circulated is increased, can be mentioned. These means of improving the stirring are useful in any of the activator solution, the bleaching solution, the fixing solution, the bleach-fix solution, the stabilizing solution, and the washing water. These methods are effective in that the effective constituents in the solution are supplied to the photographic material and the diffusion of unnecessary components in the photographic material is promoted.

In the present invention, any state of the liquid opening rate [contact area of air ($cm^2$)/liquid volume ($cm^3$)] of any of the baths can exhibit excellent performance, but in view of the stability of the liquid components, preferably the liquid opening rate is 0 to 0.1 $cm^{-1}$. In the continuous processing, from a practical point of view, the liquid opening rate is preferably 0.001 to 0.05 $cm^{-1}$, and more preferably 0.002 to 0.03 $cm^{-1}$.

The automatic developing machine (automatic processor) that can be used for the photographic material of the present invention, is preferably provided with a means of transporting a photographic material, as described in JP-A-60-191257, 60-191258, and 60-191259. Such a transporting means can reduce remarkably the carry-in of the processing solution from a preceding bath to a succeeding bath. Therefore it is high in the effect of preventing the performance of a processing solution from being deteriorated. Such an effect is particularly effective in shortening the processing time of each process and in reducing the replenishing rate of the processing solutions. To shorten the processing time, it is preferable to shorten the crossover time (the aerial time), and a method wherein a photographic material is transported between processes through a blade having a screening effect, as described, for example, in JP-A-4-86659, FIG. 4, 5, or 6, and JP-A-5-66540, FIG. 4 or 5, is preferable.

Further, if each of the processing solutions in the continuous process is concentrated due to evaporation, preferably water is added to compensate for the evaporation.

The processing time in each process according to the present invention means the time required from the start of the processing of the photographic material at any process, to the start of the processing in the next process. The actual processing time in an automatic processor is determined generally by the linear speed and the volume of the processing bath, and in the present invention, as the linear speed, 500 to 4,000 mm/min can be mentioned as a guide. Particularly in the case of a small-sized processor, 500 to 2,500 mm/min is preferable.

The processing time in the whole processing steps, that is, the processing time from the activator development process to the drying process, is preferably 360 sec or below, more preferably 120 sec or below, and particularly preferably 90 to 30 sec. Herein the processing time means the time from the dipping of the photographic material into the activator solution, till the emergence from the drying part of the processor.

In the processing applied to the present invention, various additives can be used, and more details are described in Research Disclosure Item 36544 (September 1994), whose related section is summarized below.

| Processing agents | Page |
|---|---|
| Antifoggants | 537 |
| Chelating agents | 537, right column |
| Buffers | 537, right column |
| Surface-active agents | 538, left column, and 539, left column |
| Bleaching agents | 538 |
| Bleach-accelerating agents | 538, right column to 539, left column |
| Chelating agents for bleaching | 539, left column |
| Rehalogenating agents | 539, left column |
| Fixing agents | 539, right column |
| Preservatives for fixing agents | 539, right column |
| Chelating agents for fixing | 540, left column |
| Surface-active agents for stabilizing | 540, left column |
| Scum-preventing agents for stabilizing | 540, right column |
| Chelating agents for stabilizing | 540, right column |
| Anti-fungus/mildew-preventing agents | 540, right column |
| Image-dye stabilizers | 540, right column |

The developing (applying) and processing of the activator solution (developing-processing solution) in the diffusion transfer system is known as an instant processing system in the art, and it means that the activator solution is developed and processed onto a light-sensitive material having a light-sensitive element composed of at least one light-sensitive layer/dye-forming layer (preferably the light-sensitive layer and the dye-forming layer constitutes one same layer) and an image-receiving element having a mordant layer for capturing and fixing the diffusible dye produced from the above light-sensitive layer/dye-forming layer, with the light-sensitive element and the image-receiving element on the same base, or separate bases, so as to have a liquid thickness of generally 500 μm or less, and preferably 50 to 200 μm.

If an auxiliary developing agent is built in, preferably the activator solution for production or storage of the processing solution does not contain any auxiliary developing agent.

In the case of the diffusion transfer system, preferably the pH of the activator solution is 10 to 14, and particularly preferably 12 to 14.

The process of instant light-sensitive materials is described in "The Theory of Photographic Process," Vol. 4 (1997, Macmillan), and the specific constitution of the film unit is described in JP-A-63-226649.

The dye-image-receiving layers and mordants contained therein are described in JP-A-61-252551, U.S. Pat. Nos. 2,548,564, 3,756,814, 4,124,386, and 3,625,694. The neutralizing layer for lowering the pH of the light-sensitive material after the development (application) of the activator solution is described in JP-B-7-122753, U.S. Pat. No. 4,139,383, and RD No. 16102, and the timing layer used in combination with the neutralizing layer is described in JP-A-54-136328, U.S. Pat. Nos. 4,267,262, 4,009,030, and 4,268,604. As the emulsion, any emulsion may be used, and preferable auto-positive emulsions for light-sensitive materials for photographing (shooting) that can be mentioned are those described, for example, in JP-A-7-333770 and JP-A-7-333771.

Further, if necessary, a light-shielding layer (a backing layer), a reflective layer, an intermediate layer, a separating layer, an ultraviolet-absorbing layer, a filter layer, an overcoat layer, an adhesion-improving layer, and the like may be provided.

The processing solution for processing the above light-sensitive material contains processing components necessary for the development; generally a thickening agent is incorporated into the processing solution, and the resulting solution is developed (applied) uniformly onto the light-sensitive material. As the thickening agent, a thixotropic one, such as carboxymethylcellulose and hydroxyethylcellulose, is preferable. Details of the light-sensitive layers and the processing solution are described in JP-A-7-333771.

The heating treatment in the heat development of light-sensitive materials is known in the art, and it can be applied to the light-sensitive material of the present invention. The heat-development light-sensitive materials and the process thereof are described, for example, in "Shashin Kogaku no Kiso" (published by Corona-sha, 1979), pages 553 to 555; "Eizo Joho" (published April 1978), page 40; "Nobletts Handbook of Photography and Reprography," 7th edition (Van Nostrand and Reinhold Company), pages 32 to 33; U.S. Pat. Nos. 3,152,904, 3,301,678, 3,392,020, and 3,457,075, GB-1,131,108 and GB-1,167,777, and Research Disclosure (June 1978), pages 9 to 15 (RD-17029).

To the light-sensitive material of the present invention, is preferably applied a base precursor described, for example, in U.S. Pat. Nos. 4,514,493, 4,657,848, and Kochi Gijutsu No. 5 (Mar. 22, 1991, Azutech Yugen-kaisha), pages 55 to 86, or a base-generating method described in EP-A-0 210 660 and U.S. Pat. No. 4,740,445, for the purpose of accelerating the development of silver or the reaction of the dye-formation.

To the light-sensitive material of the present invention may be added a heat solvent described in U.S. Pat. Nos. 3,347,675 and 3,667,959, for the purpose of accelerating the heat development.

When the light-sensitive material of the present invention is heat-processed, for acceleration of the development and/or diffusion transfer of the materials for processing, it is also preferable to incorporate water, an aqueous solution containing an inorganic alkali metal salt or an organic base, a low-boiling solvent, or a mixed solvent of a low-boiling solvent with water or with the above aqueous basic solution, into the light-sensitive material or the processing sheet, and to carry out the heat processing. The method wherein water is used is described, for example, in JP-A-63-144354, JP-A-63-14435, JP-A-62-38460, JP-A-3-210555, JP-A-62-253159, JP-A-63-85544, EP-A-0 210 660, and U.S. Pat. No. 4,740,445.

The present invention can also be applied to heat-development light-sensitive materials and heat-development image-forming methods described, for example, in JP-A-7-261336, JP-A-7-268045, JP-A-8-30103, JP-A-8-46822, and JP-A-8-97344.

The heating temperature in the heat-developing process is generally about 50 to 200° C., and particularly 60 to 150° C. is useful, and if a solvent is used, the heating temperature in the heat-developing process is preferably lower than its boiling point.

A technique for saving water that can be applied to the present invention is described in detail in Research Disclosure, Item 36544 (September, 1994), page 540, right column, to page 541, left column.

The novel aromatic-aldehyde-derivative compound of the present invention is a useful compound that can react only in the presence of a peroxide, to release an intended photographically useful group, and it is stable in the absence of any peroxide, thereby securing both activity at the time of processing and stability by storage. Further, the silver halide photographic light-sensitive material and the image-forming method of the present invention can provide an image that, when stored for one week under forced thermal storage conditions of temperature 50° C. and humidity 70%, brings about little stain due to the formation of dyes, the image is great in density difference between the maximum color density and the minimum color density, and the image is excellent in discrimination.

Further, the silver halide color photographic light-sensitive material and the image-forming method of the present invention can be processed with an activator solution substantially free from any p-phenylenediamine derivative apt to be deteriorated over time, they are stable in long-term storage of the light-sensitive material, they can form an image quickly by processing, they bring about little stain due to the dye-formation, and they can give an image high in difference in density between the maximum color density and the minimum color density, and excellent in discrimination.

Next, the present invention will be described in more detail with reference to the following examples, but the present invention is not restricted to them. cl EXAMPLES Example 1

Using model compounds, the stability in an alkaline solution (THF/Brinton.Robinson buffer=3/2; pH: 10; 25° C.) was observed by HPLC.

The model compounds used were, as a comparative compound, the following compound (A), having a skeleton structure described in U.S. Pat. No. 5,538,834, and the following compounds (I) and (II), having skeleton structures included in the present invention, and the decomposition thereof and 4-octylaniline that resulted therefrom were measured quantitatively.

(A)

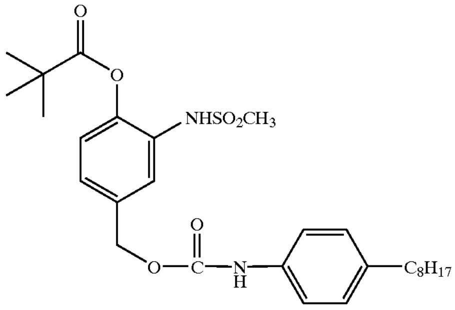

(I)

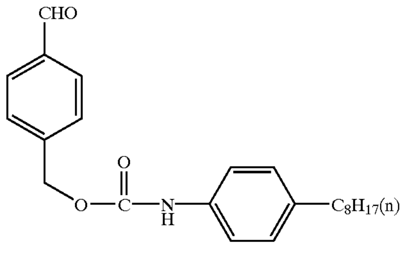

(II)

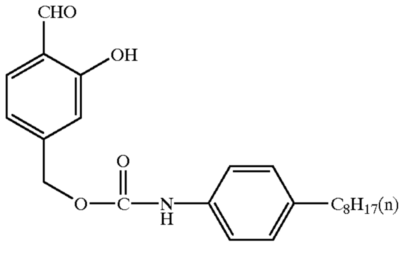

The results of the measurement are shown in FIG. 1. In FIG. 1, the line A indicates the residual amount of the comparative compound (A), the line B indicates the amount of the aniline released from the comparative compound (A), the line C indicates the residual of the compound (II) according to the present invention, and the line D indicates the amount of the aniline released from the compound (II) according to the present invention.

As is apparent from the results shown in FIG. 1, while the comparative compound was decomposed gradually in an alkaline solution, the compound included in the present invention was stable in an alkaline solution and did not release the aniline.

Example 2

Using model compounds, the reactivity in an alkaline 0.3% hydrogen peroxide solution (THF/Brinton.Robinson buffer=3/2; pH: 10; 25° C.) was observed by HPLC.

Figure 2:
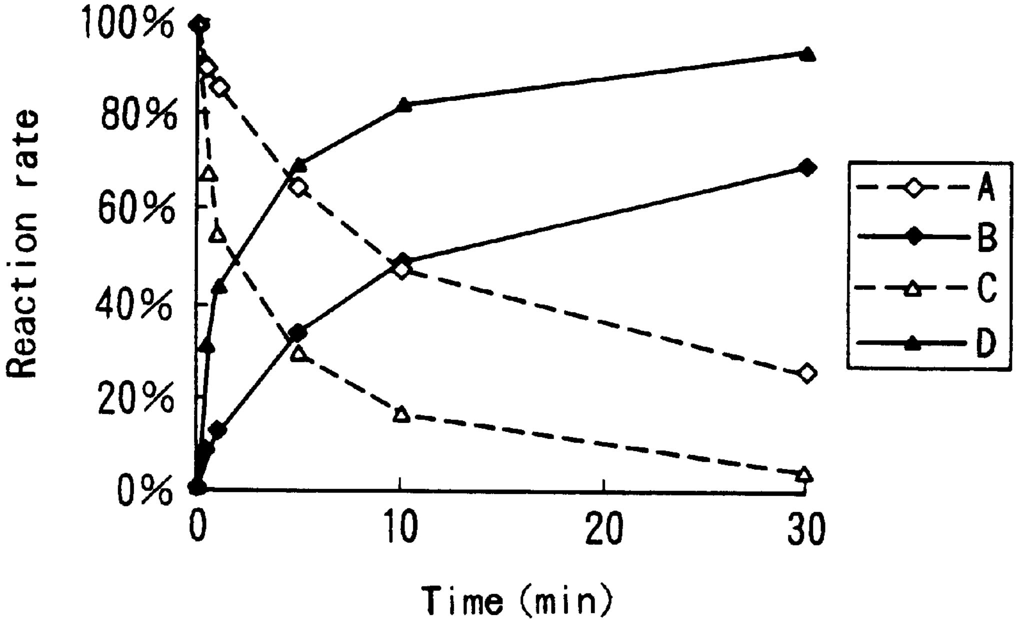
FIG. 2 is a diagram showing the results of the reactivity in a 0.3-% alkaline hydrogen peroxide solution measured by HPLC using a model compound.

The results of the measurement are shown in FIG. 2. In FIG. 2, the line A indicates the residual amount of the compound (I) according to the present invention, the line B indicates the amount of the aniline released from the compound (I) according to the present invention, the line C indicates the residual amount of the compound (II) according to the present invention, and the line D indicates the amount of the aniline released from the compound (II) according to the present invention.

As is apparent from the results shown in FIG. 2, the compound included in the present invention released an aniline compound in an alkaline hydrogen peroxide solution.

Example 3

As a peracid, m-chloroperbenzoic acid (m-CPBA) or magnesium monoperoxyphthalate (MPPM) was used, and the state of the reaction in a 0.1% solution (THF/Brinton.Robinson buffer=3/2; pH: 10; 25° C.) of each of them was observed over time by HPLC.

Figure 3:
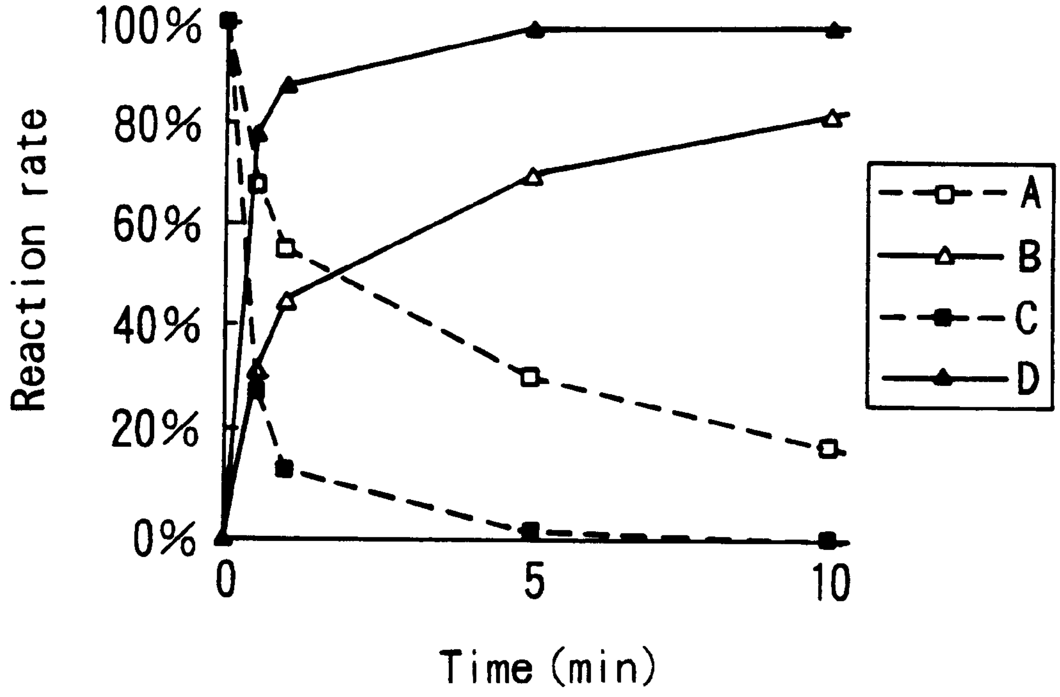
FIG. 3 is a diagram showing the results of the state of the reaction of the compound for use in the present invention in a 0.1% solution of m-chloroperbenzoic acid (m-CPBA) or magnesium monoperoxyphthalate (MPPM), measured over time by HPLC.

The results of the measurement are shown in FIG. 3. In FIG. 3, the line A indicates the residual amount of the compound (II) according to the present invention when m-CPBA was used, the line B indicates the amount of the aniline released from the compound (II) according to the present invention when m-CPBA was used, the line C indicates the residual amount of the compound (II) according to the present invention when MPPM was used, and the line D indicates the amount of the aniline released from the compound (II) according to the present invention when MPPM was used.

As is apparent from the results shown in FIG. 3, the compound included in the present invention released an aniline compound, which was a decomposition product, in the presence of not only hydrogen peroxide but also a peracid.

Example 4

A paper base, both surfaces of which had been laminated with a polyethylene, was subjected to surface corona discharge treatment; then it was provided with a gelatin undercoat layer containing sodium dodecylbenzensulfonate, and it was coated with two photographic constitutional layers, to prepare a photographic printing paper (100) having the two-layer constitution shown below. The coating solutions were prepared as follows. Hereinafter, the average grain size is defined as an average value of a diameter of a circle which corresponds to the projected area of each grain.

First-Layer Coating Solution 4.88 g of a coupler (ExY1), and 5.00 g of a solvent (Solv-1) were dissolved in ethyl acetate, and the resulting solution was emulsified and dispersed into 40 g of a 16% gelatin solution containing 10% sodium dodecylbenzensulfonate and citric acid, to prepare an emulsified dispersion A.

On the other hand, a silver chlorobromide emulsion A (cubes, a mixture of a large-size emulsion A having an average grain size of 0.88 μm, and a small-size emulsion A having an average grain size of 0.70 μm (3:7 in terms of mol of silver), the deviation coefficients of the grain size distributions being 0.08 and 0.10 respectively, and each emulsion having 0.3 mol % of silver bromide locally contained in part of the grain surface whose substrate was made up of silver chloride) was prepared. To the large-size emulsion A of this emulsion, had been added $1.4\times10^{-4}$ mol, per mol of silver, of each of blue-sensitive sensitizing dyes A, B, and C shown below, and to the small-size emulsion A of this emulsion, had been added $1.7\times10^{-4}$ mol, per mol of silver, of each of blue-sensitive sensitizing dyes A, B, and C shown below. The chemical ripening of this emulsion was carried out optimally with a sulfur sensitizer and a gold sensitizer being added. The above emulsified dispersion A and this silver chlorobromide emulsion A were mixed and dissolved, and a first-layer coating solution was prepared so that it would have the composition shown below. The coating amount of the emulsion is in terms of silver.

The coating solution for the second layer was prepared in the similar way as that for the first-layer coating solution. As the gelatin hardener for each layer, 1-oxy-3,5-dichloro-s-triazine sodium salt was used.

Further, to each layer, were added Cpd-2, Cpd-3, Cpd-4, and Cpd-5, so that the total amounts would be 15.0 mg/m$^2$, 60.0 mg/m$^2$, 50.0 mg/m$^2$, and 10.0 mg/m$^2$, respectively.

For the silver chlorobromide emulsion of the first layer, the following spectral sensitizing dyes were used.

Sensitizing dye A

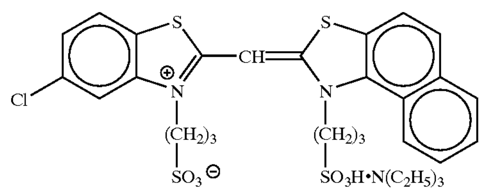

Sensitizing dye B

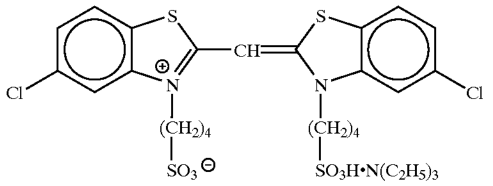

Sensitizing dye C

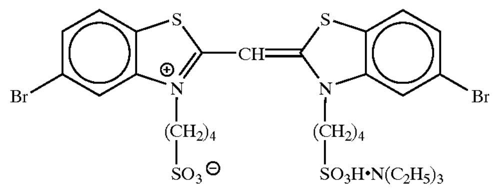

Further, 1-(5-methylureidophenyl)-5-mercaptotetrazole was added in an amount of $3.0\times10^{-3}$ mol per mol of the silver halide.

(Layer Constitution)

The composition of each layer is shown below. The numbers show coating amounts (g/m$^2$). In the case of the silver halide emulsion, the coating amount is in terms of silver.

Base A

Polyethylene-Laminated Paper

[The polyethylene on the first layer side contained a white pigment ($TiO_2$) and a blue dye (ultramarine)]

| | |
|---|---|
| First Layer | |
| The above silver chlorobromide emulsion A | 0.20 |
| Gelatin | 1.50 |
| Yellow coupler (ExY1) | 0.61 |
| Solvent (Solv-1) | 0.63 |
| Second Layer (Protective Layer) | |
| Gelatin | 1.01 |
| Acryl-modified copolymer of polyvinyl alcohol (modification degree: 17%) | 0.04 |
| Liquid paraffin | 0.02 |
| Surface-active agent (Cpd-1) | 0.01 |

Samples (101) to (108) were prepared in the same manner as in Sample (100), except that instead of the yellow coupler in the coating solution for the first layer, each yellow coupler shown in Table 2, was used, in the same molar amount, and except that each of the developing-agent precursors shown in Table 2 was added in the same molar amount to the coupler.

Further, Samples (200) to (204) were prepared in the same manner as in Sample (100), except that, in the coating solution of the first layer, the silver chlorobromide emulsion A was changed to the silver chlorobromide emulsion B shown below, in the same amount of silver, and the yellow coupler was changed to the magenta coupler shown in Table 2 in the same molar amount, and the developing agent precursor shown in Table 2 was added in the same molar amount to the coupler.

A silver chlorobromide emulsion B: cubes, a mixture of a large-size emulsion B having an average grain size of 0.55 μm, and a small-size emulsion B having an average grain size of 0.39 μm (1:3 in terms of mol of silver). The deviation coefficients of the grain size distributions were 0.10 and 0.08, respectively, and each emulsion had 0.8 mol % of AgBr contained locally in part of the grain surface whose substrate was made up of silver chloride.

For the silver chlorobromide emulsion B, the following spectral sensitizing dyes were used.

Sensitizing dye D

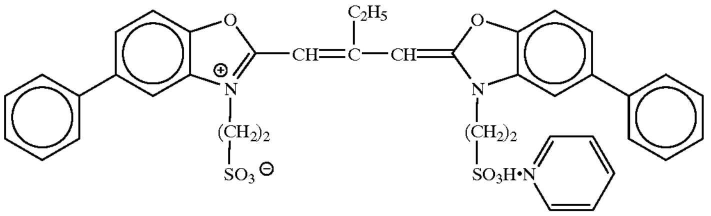

Sensitizing dye E

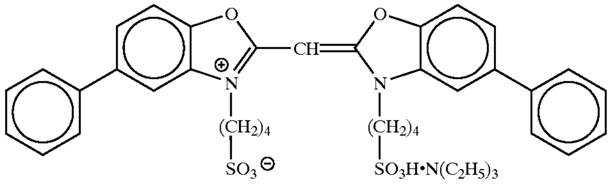

Sensitizing dye F

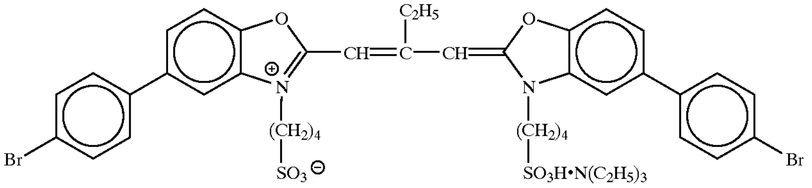

(The sensitizing dye D was added to the large-size emulsion in an amount of $3.0\times10^{-4}$ mol per mol of the silver halide, and to the small-size emulsion in an amount of $3.6\times10^{-4}$ mol per mol of the silver halide; the sensitizing dye E was added to the large-size emulsion in an amount of $4.0\times10^{-5}$ mol per mol of the silver halide, and to the small-size emulsion in an amount of $7.0\times10^{-5}$ mol per mol of the silver halide; and the sensitizing dye F was added to the large-size emulsion in an amount of $2.0\times10^{-4}$ mol per mol of the silver halide, and to the small-size emulsion in an amount of $2.8\times10^{-4}$ mol per mol of the silver halide.)

Further, Samples (300) to (304) were prepared in the same manner as in Sample (100), except that, in the coating solution of the first layer, the silver chlorobromide emulsion A was changed to the silver chlorobromide emulsion C shown below, in the same amount of silver, and the yellow coupler was changed to the cyan coupler shown in Table 2 in the same molar amount, and the developing agent precursor shown in Table 2 was added in the same molar amount to the coupler.

A silver chlorobromide emulsion C: cubes, a mixture of a large-size emulsion C having an average grain size of 0.5 μm, and a small-size emulsion C having an average grain size of 0.41 μm (1:4 in terms of mol of silver). The deviation coefficients of the grain size distributions were 0.09 and 0.11, respectively, and each emulsion had 0.8 mol % of AgBr contained locally in part of the grain surface whose substrate was made up of silver chloride.

For the silver chlorobromide emulsion C, the following spectral sensitizing dyes were used.

Sensitizing dye G

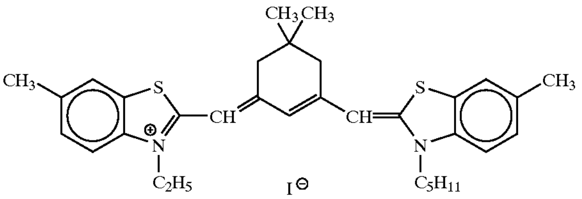

Sensitizing dye H

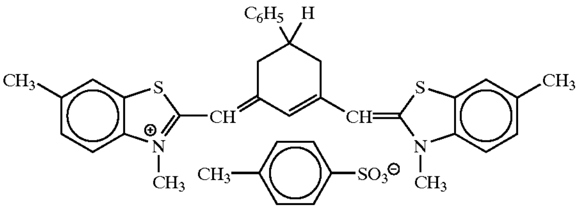

(The sensitizing dyes G and H were added to the large-size emulsion in an amount of $5.0\times10^{-5}$ mol per mol of the silver halide, and to the small-size emulsion in an amount of $8.0\times10^{-5}$ mol per mol of the silver halide, respectively.)

(Cpd-1)

Surface-active agent
A mixture in 7:3 (weight ratio) of

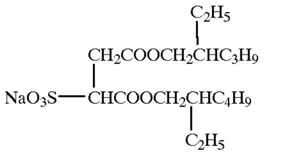

and

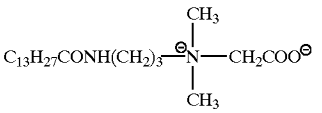

(Cpd-2)

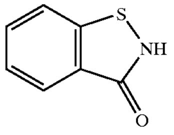

Antiseptics

-continued (Cpd-3)

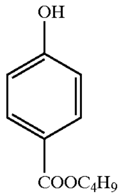

Antiseptics (Cpd-4)

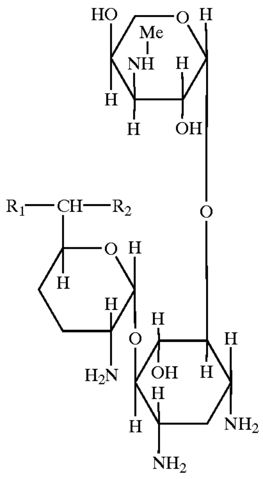

| | $R_1$ | $R_2$ |
|---|---|---|
| a | —Me | —NHMe |
| b | —Me | $—NH_2$ |
| c | —H | $—NH_2$ |
| d | —H | —NHMe |

1:1:1:1 mixture of a,b,c,d

Antiseptics (Cpd-5)

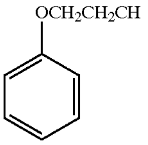

Antiseptics (Solv-1)

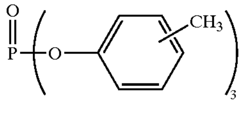

Solvent (EXY 1)

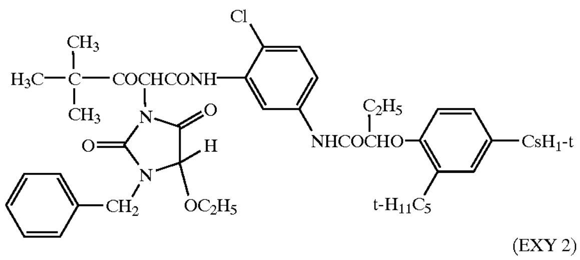

(EXY 2)

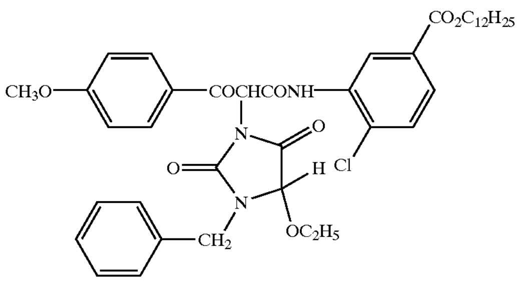

-continued (EXM 1)

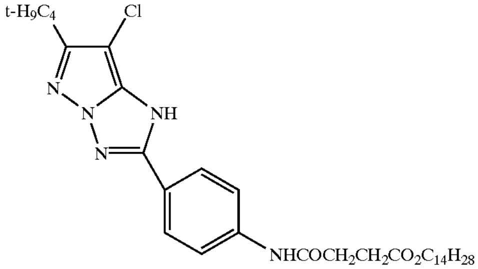

(EXM 2)

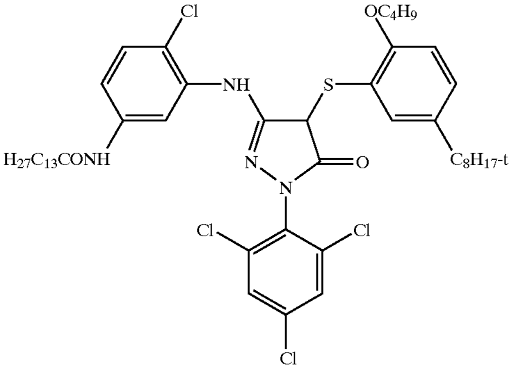

(EXC 1)

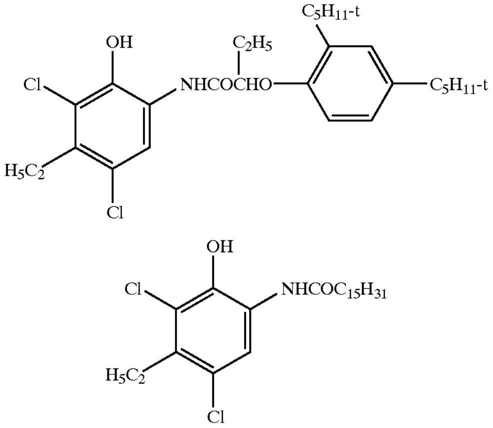

15:85 (molar ratio)

(EXC 2)

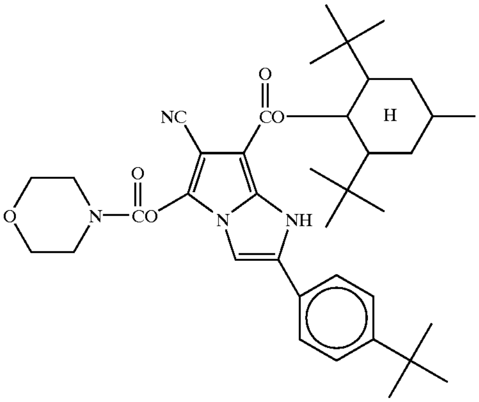

-continued (EXD 1)

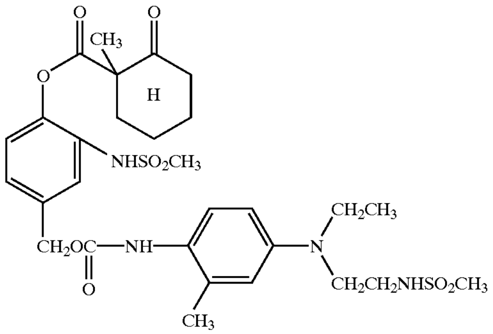

(EXD 2)

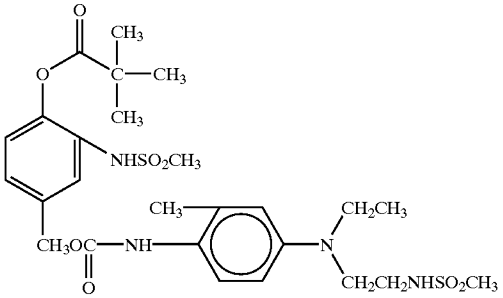

Two sheets of each of the thus-prepared samples were provided, one sheet was placed under forced thermal conditions of temperature 50° C. and humidity 70% for one week, and at the same time the other was stored under refrigeration. After the samples subjected to the thermal test and the samples stored under refrigeration were processed in the following processing step 1, the density difference $\Delta_D{}^{B}$min of yellow between the samples subjected to the thermal test, and the samples stored under refrigeration, with respect to Samples (100) to (108); the density difference $\Delta_D{}^{G}$min of magenta, with respect to Samples (200) to (204); and the density difference $\Delta_D{}^{R}$min of cyan, with respect to Samples (300) to (304), were measured, respectively. The results are shown in Table 2. It is meant that the smaller these values are, the less the stain due to long-term storage is.

| Processing step 1 | | |
|---|---|---|
| Processing step | Temperature | Time |
| Bleach-fix | 40° C. | 45 sec |
| Rinse | room temperature | 90 sec |

(Bleach-fix Solution)

| | |
|---|---|
| Water | 600 ml |
| Ammonium thiosulfate (700 g/liter) | 93 ml |
| Ammonium sulfite | 40 g |
| Ethylenediaminetetraacetic acid iron (III) ammonium | 55 g |
| Ethylenediaminetetraacetic acid | 2 g |
| Nitric acid (67%) | 30 g |
| Water to make | 1,000 ml |
| pH (at 25° C. by using acetic acid and aqueous ammonia) | 5.8 |

(Rinsing Solution)

| | |
|---|---|
| Sodium chloroisocyanurate | 0.02 g |
| Deionized water | |
| (having a conductivity of 5 μS/cm or below) | 1000 ml |
| pH | 6.5 |

Using each sample unprocessed with an FWH-type sensitometer (color temperature of the light source: 3,200° K.), manufactured by Fuji Photo Film Co., Ltd., gradation exposure was given to the thus prepared Samples (100) to (108) through a blue filter for sensitometry, to the thus prepared Samples (200) to (204) through a green filter for sensitometry, and to the thus prepared Samples (300) to (304) through a red filter for sensitometry.

The thus exposed Samples were processed with the following processing solutions in the following processing step 2.

Processing step 2

| Processing step | Temperature | Time |
|---|---|---|
| Development | 40° C. | 45 sec |
| Bleach-fix | 40° C. | 45 sec |
| Rinse | room temperature | 90 sec |

(Developing Solution (alkali activator solution containing hydrogen peroxide))

| | |
|---|---|
| Water | 600 ml |
| Potassium carbonate | 30 g |
| Hydrogen peroxide (30%) | 20 ml |
| Potassium chloride | 5 g |
| Hydroxylethylidene-1,1-diphosphonic acid (30%) | 4 ml |
| pH (at 25° C. by using sulfuric acid) | 10.5 |

The bleach-fix solution and the rinsing solution used in the above were used.

The maximum color density (Dmax) part and the minimum color density (Dmin) part of each of the processed Samples were measured, using blue light for Samples (100) to (108), green light for Samples (200) to (204), and red light for Samples (300) to (304), respectively. The difference between the maximum color density and the minimum color density (ΔDmax) are shown in Table 2.

TABLE 2

| Sample No. | Coupler | Color-developing agent percursor | Δ Dmin | Δ Dmax | Remarks |
|---|---|---|---|---|---|
| 100 | ExY1 | — | 0 | 0 | Comparative example |
| 101 | " | ExD1 | 0.21 | 0.59 | Comparative example |
| 102 | " | ExD2 | 0.18 | 0.42 | Comparative example |
| 103 | " | (2) | 0.02 | 0.98 | This invention |
| 104 | " | (3) | 0.03 | 0.99 | This invention |
| 105 | " | (4) | 0.02 | 0.96 | This invention |
| 106 | " | (11) | 0.04 | 1.01 | This invention |
| 107 | ExY2 | (2) | 0.02 | 0.99 | This invention |
| 108 | " | (3) | 0.03 | 1.00 | This invention |
| 200 | ExM1 | — | 0 | 0 | Comparative example |
| 201 | " | (2) | 0.01 | 1.01 | This invention |
| 202 | " | (3) | 0.01 | 1.03 | This invention |
| 203 | ExM2 | (2) | 0.01 | 0.93 | This invention |
| 204 | " | (3) | 0.01 | 0.94 | This invention |

TABLE 2-continued

| Sample No. | Coupler | Color-developing agent percursor | Δ Dmin | Δ Dmax | Remarks |
|---|---|---|---|---|---|
| 300 | ExC1 | — | 0 | 0 | Comparative example |
| 301 | " | (2) | 0.01 | 1.01 | This invention |
| 302 | " | (3) | 0.01 | 1.01 | This invention |
| 303 | ExC2 | (2) | 0.01 | 1.36 | This invention |
| 304 | " | (3) | 0.01 | 1.28 | This invention |

As is apparent from the results shown in Table 2, when the processing is carried out with a processing solution free from any color-developing agent without using any color-developing agent precursor, color formation did not take place. When Comparative Compound EXD1 or EXD2 was used, color formation took place, but stain (ΔDmin) due to the formation of a dye resulted by the storage. On the other hand, it is understood that the light-sensitive material and the image-forming method of the present invention using the color-developing agent precursor for use in the present invention resulted in little stain due to the dye-formation under such storage conditions, and an image whose density difference between the maximum color density and the minimum color density was great, and whose discrimination was excellent, could be obtained.

Example 5

With respect to Samples (100) to (104), (200) to (202), and (300) to (302) in the Example 4, the evaluation of ΔDmax was carried out in the same manner as in Example 4, except that 20 ml of hydrogen oxide (30%) in the developing solution was changed to 2 g of magnesium monoperoxyphthalate. The results are shown in Table 3.

TABLE 3

| Sample No. | Coupler | Color-developing agent percursor | Δ Dmax | Remarks |
|---|---|---|---|---|
| 100 | ExY1 | — | 0 | Comparative example |
| 101 | " | ExD1 | 0.60 | Comparative example |
| 102 | " | ExD2 | 0.43 | Comparative example |
| 103 | " | (2) | 1.21 | This invention |
| 104 | " | (3) | 1.23 | This invention |
| 200 | ExM1 | — | 0 | Comparative example |
| 201 | " | (2) | 1.26 | This invention |
| 202 | " | (3) | 1.29 | This invention |
| 300 | ExC1 | — | 0 | Comparative example |
| 301 | " | (2) | 1.27 | This invention |
| 302 | " | (3) | 1.27 | This invention |

It is also understood that, when the developing (activator) solution to which magnesium monoperoxyphthalate was added instead of hydrogen peroxide was used, the sample in which the color-developing agent precursor for use in the present invention was used gave an image excellent in discrimination and exhibited much better color-forming property than when hydrogen peroxide was used.

Example 6

Preparation of Sample (600)

A paper base, both surfaces of which had been laminated with a polyethylene, was subjected to surface corona discharge treatment; then it was provided with a gelatin undercoat layer containing sodium dodecylbenzensulfonate, and it was coated with seven photographic constitutional layers, to prepare a photographic printing paper (600) having the seven-layer constitution shown below. The coating solutions were prepared as follows. Hereinafter, the average grain size is defined as an average value of a diameter of a circle which corresponded to the projected area of each grain.

First-Layer Coating Solution 4.88 g of a yellow coupler (Y-1), 0.64 g of a color-image stabilizer (Cpd-1), 0.32 g of a color-image stabilizer (Cpd-2), 0.64 g of a color-image stabilizer (Cpd-3), and 1.74 g of a solvent (Solv-1) were dissolved in ethyl acetate, and the resulting solution was emulsified and dispersed into 40 g of a 16% gelatin solution containing 10% sodium dodecylbenzensulfonate and citric acid, to prepare an emulsified dispersion C.

On the other hand, a silver chlorobromide emulsion A (cubes, a mixture of a large-size emulsion A having an average grain size of 0.88 μm, and a small-size emulsion A having an average grain size of 0.70 μm (3:7 in terms of mol of silver), the deviation coefficients of the grain size distributions being 0.08 and 0.10 respectively, and each emulsion having 0.3 mol % of silver bromide locally contained in part of the grain surface whose substrate was made up of silver chloride) was prepared. To the large-size emulsion A of this emulsion, had been added $1.4\times10^{-4}$ mol, per mol of silver, of each of blue-sensitive sensitizing dyes A, B, and C shown below, and to the small-size emulsion A of this emulsion, had been added $1.7\times10^{-4}$ mol, per mol of silver, of each of blue-sensitive sensitizing dyes A, B, and C shown below. The chemical ripening of this emulsion was carried out with a sulfur sensitizer and a gold sensitizer being added. The above emulsified dispersion A and this silver chlorobromide emulsion A were mixed and dissolved, and a first-layer coating solution was prepared so that it would have the composition shown below. The coating amount of the emulsion is in terms of silver.

The coating solutions for the second layer to seventh layer were prepared in the similar way as that for the first-layer coating solution. As the gelatin hardener for each layer, 1-oxy-3,5-dichloro-s-triazine sodium salt was used.

Further, to each layer, were added Cpd-12, Cpd-13, Cpd-14, and Cpd-15, so that the total amounts would be 15.0 mg/m$^2$, 60.0 mg/m$^2$, 5.0 mg/m$^2$, and 10.0 mg/m$^2$, respectively.

For the silver chlorobromide emulsion of each photosensitive emulsion layer, the following spectral sensitizing dyes were used.

(Blue-Sensitive Emulsion Layer)

Sensitizing dye A

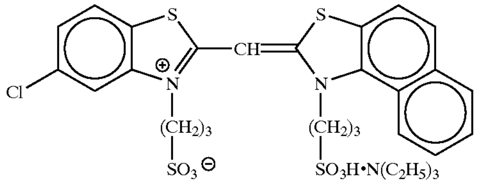

Sensitizing dye B

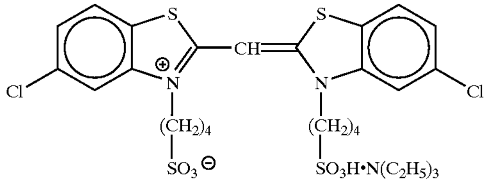

Sensitizing dye C

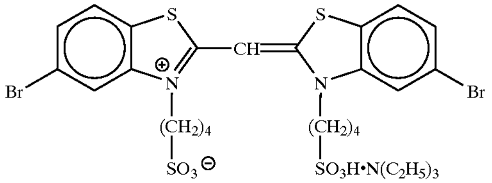

(Each was added to the large-size emulsion in an amount of $1.4\times10^{-4}$ mol, per mol of silver halide, and to the small-size emulsion in an amount of $1.7\times10^{-4}$ mol, per mol of silver halide.)

(Green-Sensitive Emulsion Layer)

Sensitizing dye D

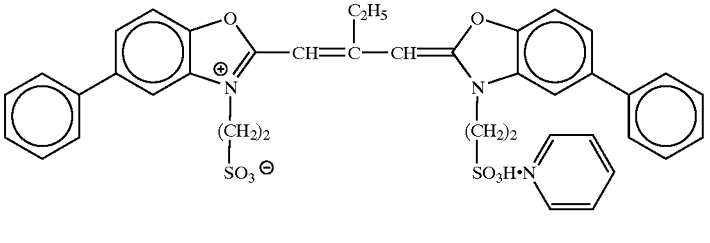

Sensitizing dye E

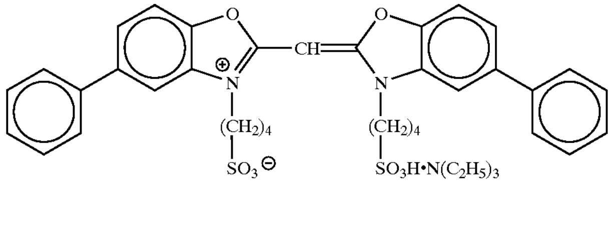

-continued

Sensitizing dye F

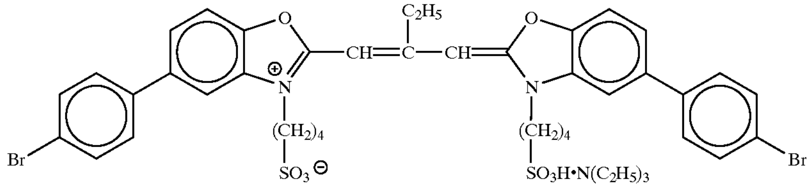

(The sensitizing dye D was added to the large-size emulsion in an amount of $3.0\times10^{-4}$ mol per mol of the silver halide, and to the small-size emulsion in an amount of $3.6\times10^{-4}$ mol per mol of the silver halide; the sensitizing dye E was added to the large-size emulsion in an amount of $4.0\times10^{-5}$ mol per mol of the silver halide, and to the small-size emulsion in an amount of $7.0\times10^{-5}$ mol per mol of the silver halide; and the sensitizing dye F was added to the large-size emulsion in an amount of $2.0\times10^{-4}$ mol per mol of the silver halide, and to the small-size emulsion in an amount of $2.8\times10^{-4}$ mol per mol of the silver halide.)

Sensitizing dye G

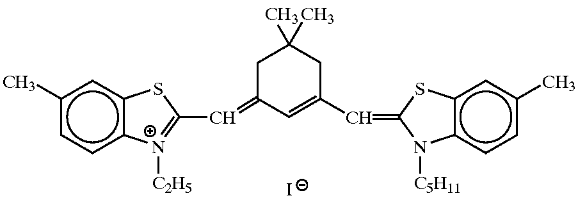

Sensitizing dye H

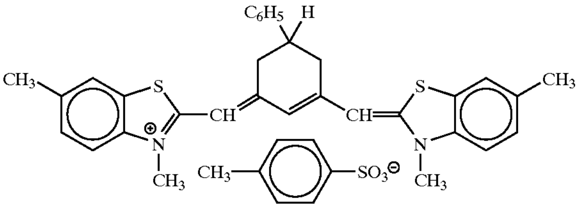

(Each was added to the large-size emulsion in an amount of $5.0\times10^{-5}$ mol per mol of the silver halide, and to the small-size emulsion in an amount of $8.0\times10^{-5}$ per mol of the silver halide.)

Further, the following compound was added to the red-sensitive emulsion layer in an amount of $2.6\times10^{-3}$ mol per mol of the silver halide.

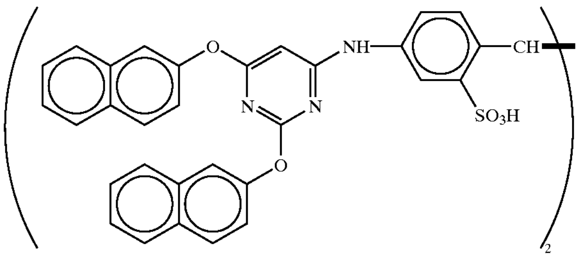

To the blue-sensitive emulsion layer, the green-sensitive emulsion layer, and the red-sensitive emulsion layer, was added 1-(5-methylureidophenyl)-5-mercaptotetrazole in amounts of $3.3\times10^{-4}$ mol, $1.0\times10^{-3}$ mol, and $5.9\times10^{-4}$ mol, respectively, per mol of the silver halide.

Further, to the second layer, the forth layer, the sixth layer, and the seventh layer, was added 1-(5-methylureidophenyl)-5-mercaptotetrazole in amounts of 0.2 mg/m$^2$, 0.2 mg/m$^2$, 0.6 mg/m$^2$, and 0.1 mg/m$^2$, respectively.

Further, to the blue-sensitive emulsion layer and the green-sensitive emulsion layer, were added 4-hydroxy-6-methyl-1,3,3a,7-tetrazaindene in amounts of $1\times10^{-4}$ mol and $2\times10^{-4}$ mol, respectively, per mol of the silver halide.

Further, to prevent irradiation, the following dyes were added to the emulsion layers (the coating amount is shown in parentheses).

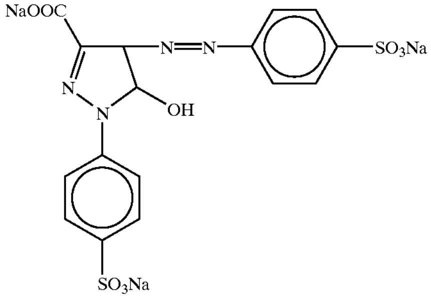

(10mg/m$^2$)

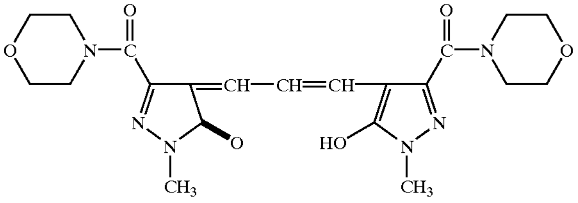

(20mg/m$^2$)

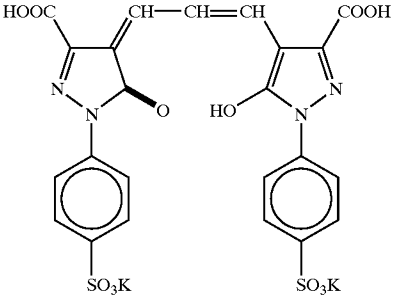

(5mg/m$^2$)

-continued

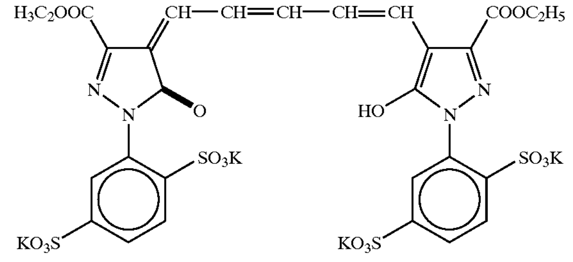

($20 mg/m^2$)

and

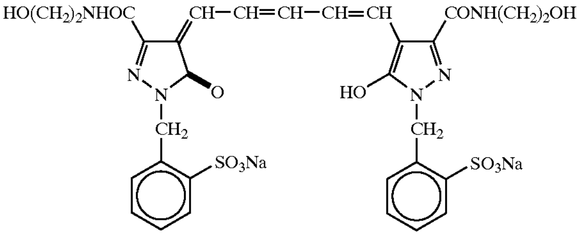

($20 mg/m^2$)

(Layer Constitution)

The composition of each layer is shown below. The numbers show coating amounts ($g/m^2$). In the case of the silver halide emulsion, the coating amount is in terms of silver.

Base

Polyethylene-laminated Paper

[The polyethylene on the first layer side contained the following fluorescent whitening agents (I) and (II), a white pigment ($TiO_2$, 15 wt %), and a blue dye (ultramarine)]

| | |
|---|---|
| First Layer (Blue-Sensitive Emulsion Layer) | |
| The above silver chlorobromide emulsion A | 0.27 |
| Gelatin | 1.43 |
| Yellow coupler ($ExY_1$) | 0.61 |
| Color-image stabilizer (Cpd-1) | 0.08 |
| Color-image stabilizer (Cpd-2) | 0.04 |
| Color-image stabilizer (Cpd-3) | 0.08 |
| Solvent (Solv-1) | 0.22 |
| Second Layer (Color-Mixing Inhibiting Layer) | |
| Gelatin | 1.09 |
| Color-mixing inhibitor (Cpd-4) | 0.11 |
| Color-image stabilizer (Cpd-16) | 0.15 |
| Solvent (Solv-1) | 0.10 |
| Solvent (Solv-2) | 0.15 |
| Solvent (Solv-3) | 0.12 |
| Solvent (Solv-7) | 0.01 |
| Third Layer (Green-Sensitive Emulsion Layer) | |
| A silver chlorobromide emulsion B: (cubes, a mixture of a large-size emulsion B having an average grain size of 0.55 μm, and a small-size emulsion B having an average grain size of 0.39 μm (1:3 in terms of mol of silver). The deviation coefficients of the grain size distributions were 0.10 and 0.08, Respectively, and each emulsion had 0.8 mol % of AgBr contained in part of the grain surface whose substrate was made up of silver chloride.) | 0.13 |
| Gelatin | 1.35 |
| Magenta coupler ($ExM_1$) | 0.12 |

-continued

| | |
|---|---|
| Ultraviolet absorbing agent (UV-1) | 0.12 |
| Color-image stabilizer (Cpd-2) | 0.01 |
| Color-image stabilizer (Cpd-4) | 0.01 |
| Color-image stabilizer (Cpd-5) | 0.01 |
| Color-image stabilizer (Cpd-6) | 0.01 |
| Color-image stabilizer (Cpd-8) | 0.01 |
| Color-image stabilizer (Cpd-16) | 0.08 |
| Color-image stabilizer (Cpd-18) | 0.0001 |
| Solvent (Solv-4) | 0.20 |
| Solvent (Solv-5) | 0.11 |
| Solvent (Solv-9) | 0.19 |
| Fourth Layer (Color-Mixing Inhibiting Layer) | |
| Gelatin | 0.77 |
| Color-mixing inhibitor (Cpd-4) | 0.08 |
| Color-image stabilizer (Cpd-16) | 0.11 |
| Solvent (Solv-1) | 0.07 |
| Solvent (Solv-2) | 0.11 |
| Solvent (Solv-3) | 0.09 |
| Solvent (Solv-7) | 0.01 |
| Fifth Layer (Red-Sensitive Emulsion Layer) | |
| A silver chlorobromide emulsion C: (cubes, a mixture of a large-size emulsion C having an average grain size of 0.50 μm, and a small-size emulsion having an average grain size of 0.41 μm (1:4 in terms of mol of silver). The deviation coefficients of the grain size distributions were 0.09 and 0.11, respectively, and each emulsion had 0.8 mol % of silver bromide locally contained in part of the grain surface whose substrate was made up of silver chloride). | 0.18 |
| Gelatin | 0.80 |
| Cyan coupler ($ExC_1$) | 0.28 |
| Ultraviolet absorbing agent (UV-3) | 0.19 |
| Color-image stabilizer (Cpd-1) | 0.24 |
| Color-image stabilizer (Cpd-6) | 0.01 |
| Color-image stabilizer (Cpd-8) | 0.01 |
| Color-image stabilizer (Cpd-9) | 0.04 |
| Color-image stabilizer (Cpd-10) | 0.01 |
| Solvent (Solv-1) | 0.01 |
| Solvent. (Solv-6) | 0.21 |
| Sixth Layer (Ultraviolet Absorbing Layer) | |
| Gelatin | 0.64 |
| Ultraviolet absorbing agent (UV-2) | 0.39 |
| Color-image stabilizer (Cpd-7) | 0.05 |
| Color-image stabilizer (Cpd-17) | 0.05 |
| Solvent (Solv-8) | 0.05 |
| Seventh Layer (Protective Layer) | |
| Gelatin | 1.01 |
| Acryl-modified copolymer of polyvinyl alcohol (modification degree: 17%) | 0.04 |
| Liquid paraffin | 0.02 |
| Surface-active agent (Cpd-11) | 0.01 |

(EXY 1)

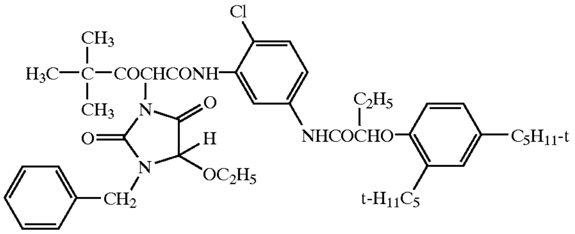

-continued
(EXY 2)
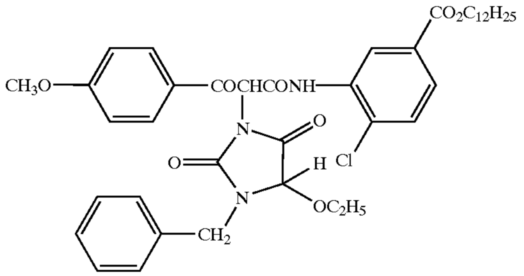
(EXY 3)
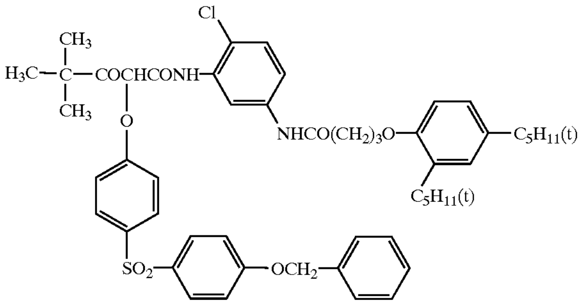
(EXY 4)
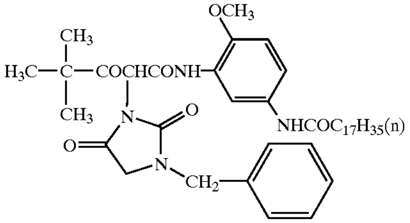
(EXM 1)
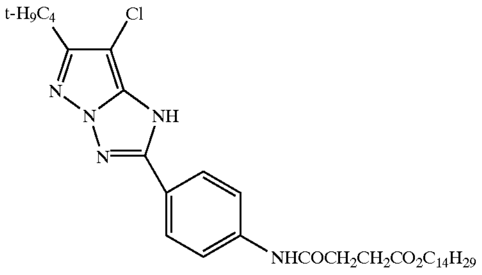
(EXM 2)
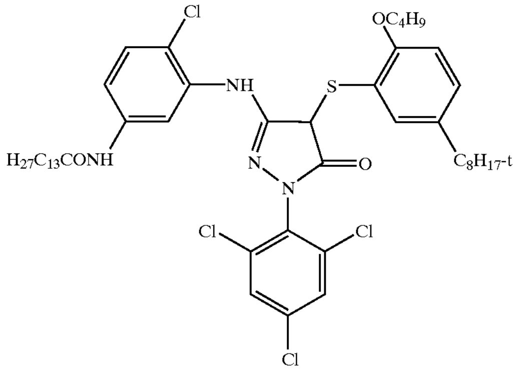
-continued
(EXM 3)
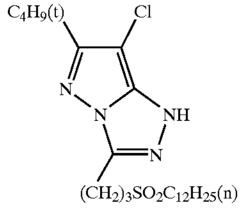
(EXM 4)
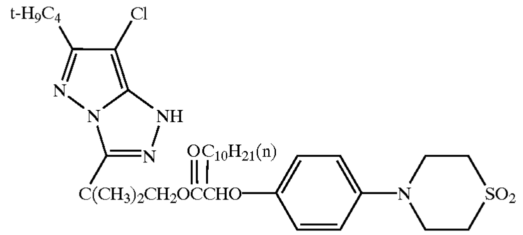
(EXC 1)
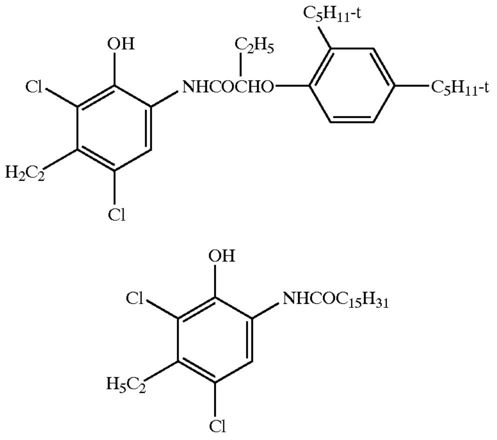
15:85 (molar ratio)
(EXC 2)
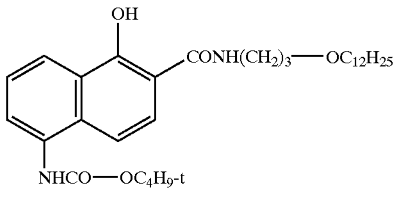
(EXC 3)
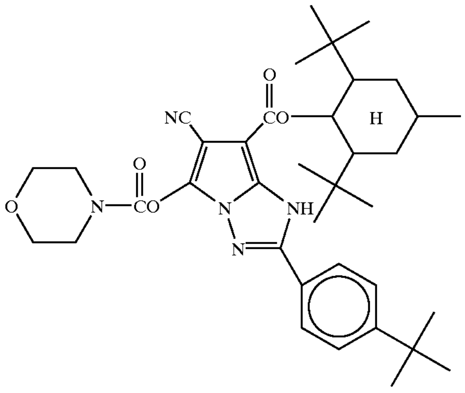

-continued (EXC 4)

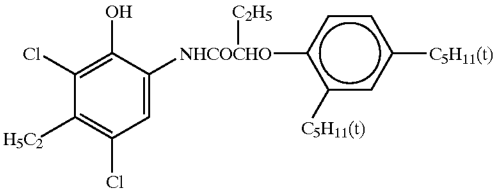

(EXC 5)

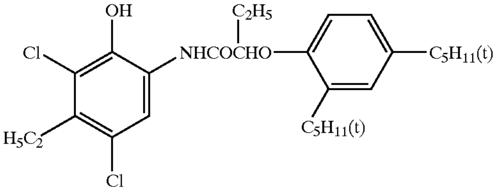

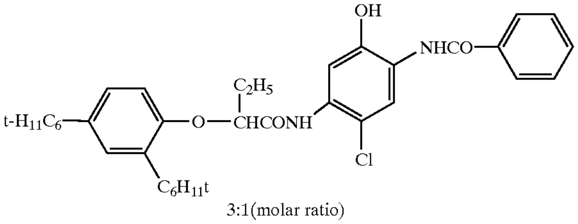

3:1(molar ratio)

(Cpd-1)

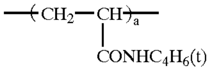

number average molecular weight 60,000

Color-image stabilizer (Cpd-2)

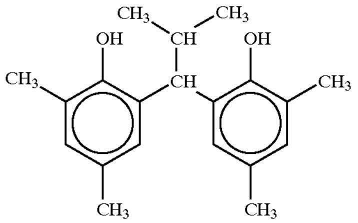

Color-image stabilizer (Cpd-3)

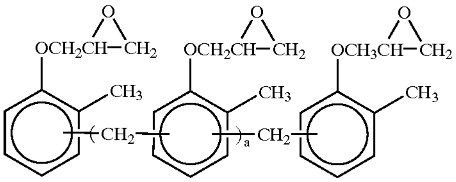

n = 7 ~ 8 (average)

Color-image stabilizer (Cpd-4)

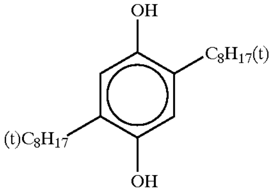

Color-mixing inhibitor

-continued (Cpd-5)

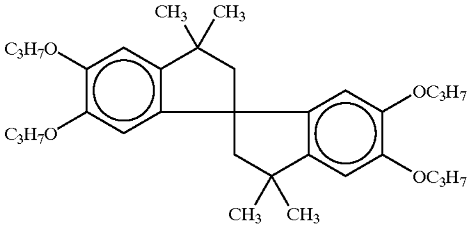

Color-image stabilizer (Cpd-6)

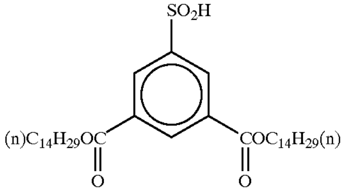

Color-image stabilizer (Cpd-7)

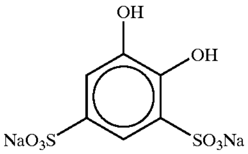

Color-image stabilizer (Cpd-8)

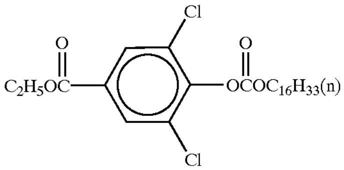

Color-image stabilizer (Cpd-9)

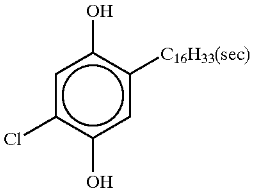

Color-image stabilizer (Cpd-10)

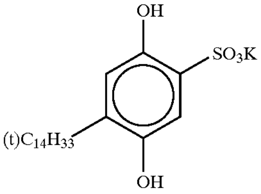

Color-image stabilizer (Cpd-11)

A mixture in 7:3 (weight ratio) of

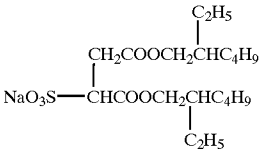

and

Surface-active agent

-continued
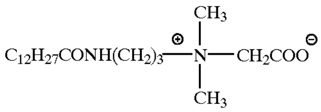
(Cpd-12)
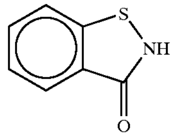
Antiseptics
(Cpd-13)
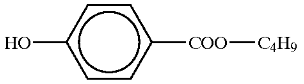
Antiseptics
(Cpd-14)
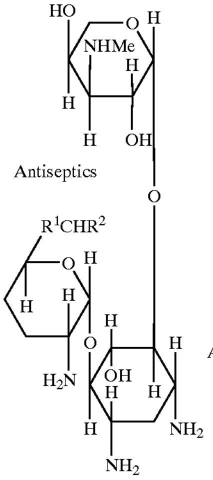
Antiseptics
| | $R^1$ | $R^2$ |
|---|---|---|
| a | —Me | —NHMe |
| b | —Me | —$NH_2$ |
| c | —H | —$NH_2$ |
| d | —H | —NHMe |
A mixture in 1:1:1:1 (weight ratio) of a, b, c, d
(Cpd-15)
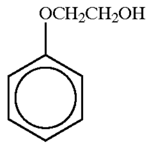
Antiseptics
(Cpd-16)
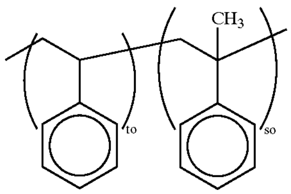
number average molecular weight 590
Percentage by weight of aromatic rings 65%
-continued
(Cpd-17)
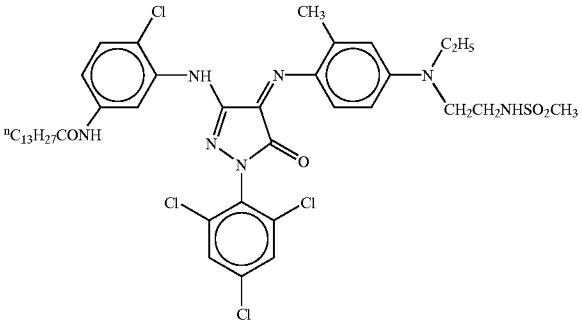
(1)
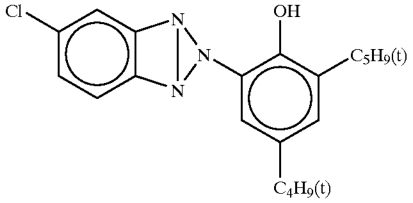
(UV-1) UV absorbing agent
(2)
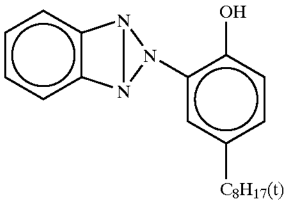
(3)
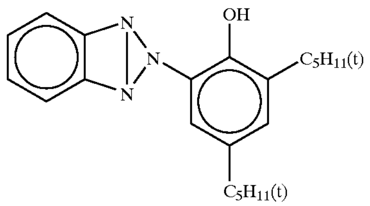
A mixture in 1:3:4 (weight ratio) of (1):(2):(3)
(1)
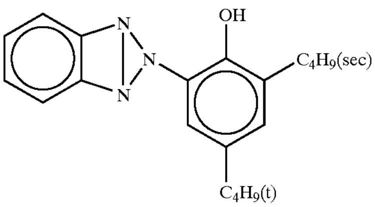
(UV-2) UV absorbing agent
(2)
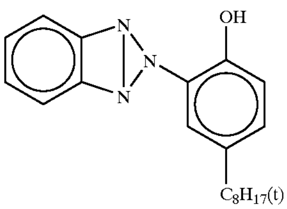

-continued
(3)
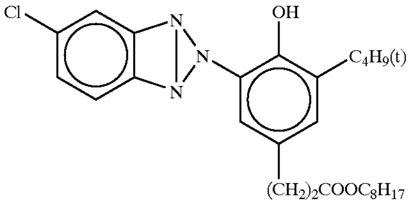
(4)
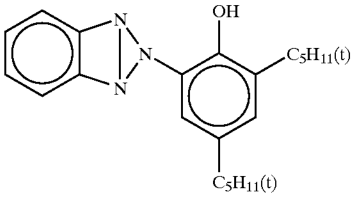
(5)
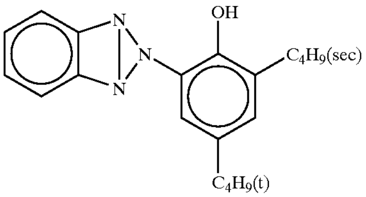
A mixture in 1:2:2:3:1 (weight ratio) of (1):(2):(3):(4):(5)
(1)
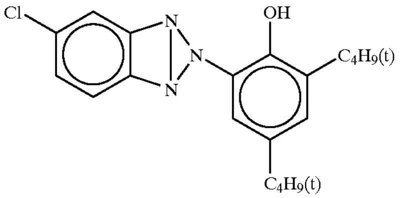
(UV-3) UV absorbing agent
(2)
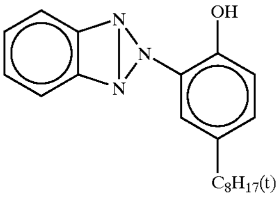
(3)
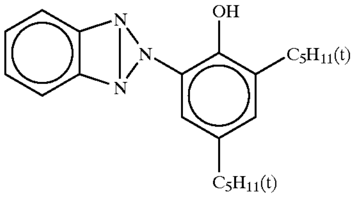
(4)
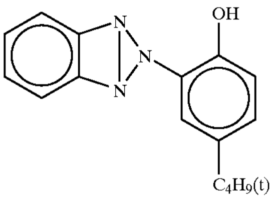
A mixture in 1:3:2:1 (weight ratio) of (1), (2), (3), (4)
-continued
(Solv-1)
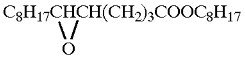
Solvent
(Solv-2)
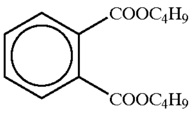
Solvent
(Solv-3)
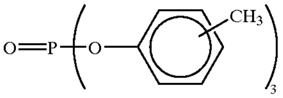
Solvent
(Solv-4)
$O{=}P{-}(O{-}C_6H_{13}(n))_3$
Solvent
(Solv-5)
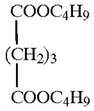
Solvent
(Solv-6)
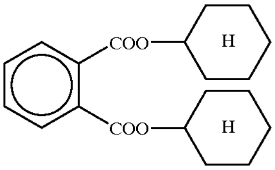
Solvent
(Solv-7)
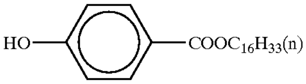
Solvent
(Solv-8)
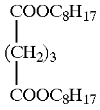
Solvent
(Solv-9)
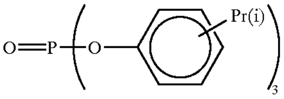
Solvent
(II)
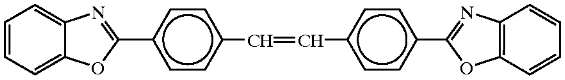
Flourescent whitening agent -continued (I)

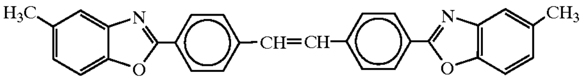

Flourescent whitening agent

11/1 = 20/80 (weight ratio) Content $15mg/m^2$

Ratio of 0.05% by weight to polyethylene

Samples (601) to (617) were prepared in the same manner as in Sample (600), except that instead of the couplers in the coating solutions for the first layer, the third layer, and the fifth layer, the couplers shown in Table 4, were used, in the same molar amounts, and except that the color-developing agent precursor shown in Table 4 was added in the same molar amount to the coupler.

TABLE 4

| Sample | Coupler | | | Color-developing |
|---|---|---|---|---|
| No. | Yellow | Magenta | Cyan | agent precursor |
| 600 | ExY1 | ExM1 | ExC1 | — |
| 601 | " | " | " | ExD1 |
| 602 | " | " | " | ExD2 |
| 603 | " | " | " | (2) |
| 604 | " | " | " | (3) |
| 605 | " | " | " | (4) |
| 606 | " | " | " | (11) |
| 607 | ExY2 | ExM2 | ExC2 | (2) |
| 608 | " | " | " | (3) |
| 609 | ExY1 | ExM1 | ExC3 | (2) |
| 610 | " | " | " | (4) |
| 611 | ExY3 | ExM3 | ExC4 | (2) |
| 612 | " | " | " | (11) |
| 613 | ExY4 | ExM4 | ExC5 | (2) |
| 614 | " | " | " | (3) |
| 615 | ExY1 | ExM1 | ExC1 | (46) |
| 616 | " | " | " | (48) |
| 617 | " | " | " | (51) |

As the method of addition of the color-developing agent precursor, a method in which the precursor was contained in the emulsified dispersion of each emulsion layer in the same molar amount to the coupler contained in the layer, was employed.

(EXD 1)

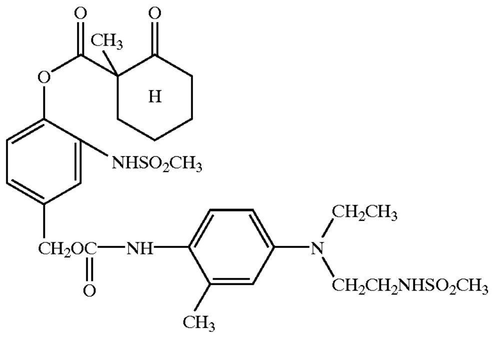

-continued (EXD 2)

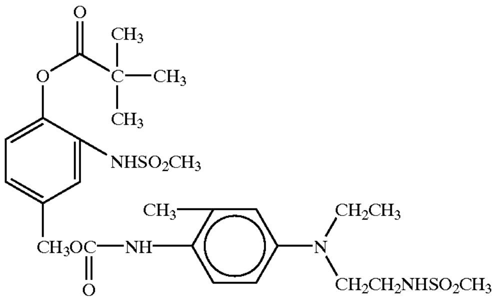

Two sheets of each of the thus-prepared samples were provided, one sheet was placed under forced thermal conditions of temperature 50° C. and humidity of 70% for one week, and at the same time, the other was stored under refrigeration. After the samples subjected to the thermal test and the samples stored under refrigeration were processed in the following processing step 1, the density difference ΔDminB of yellow between the samples subjected to the thermal test and the samples stored under refrigeration, the density difference ΔDminG of magenta, and the density difference ΔDminR of cyan were measured. The results are shown in Table 5. It is meant that the smaller these values are, the less the stain due to the long-term storage is.

| Processing step 1 | | |
|---|---|---|
| Processing step | Temperature | Time |
| Bleach-fixing | 40° C. | 45 sec |
| Rinse | room temperature | 90 sec |

(Bleach-fix Solution)

| | |
|---|---|
| Water | 600 ml |
| Ammonium thiosulfate (700 g/liter) | 93 ml |
| Ammonium sulfite | 40 g |
| Ethylenediaminetetraacetic acid iron (III) ammonium | 55 g |
| Ethylenediaminetetraacetic acid | 2 g |
| Nitric acid (67%) | 30 g |
| Water to make | 1,000 ml |
| pH (at 25° C. by using acetic acid and aqueous ammonia) | 5.8 |

(Rinsing Solution)

| | |
|---|---|
| Sodium chloroisocyanurate | 0.02 g |
| Deionized water | 1000 ml |
| (having a conductivity of 5 μS/cm or below) | |
| pH | 6.5 |

Using an FWH-type sensitometer (color temperature of the light source: 3,200° K.), manufactured by Fuji Photo Film Co., Ltd., gradation exposure was given to the thus prepared unprocessed-samples through a three-color separation filter for sensitometry.

The thus exposed Samples were processed with the following processing solutions in the following processing step 2.

| Processing step 2 | | |
|---|---|---|
| Processing step | Temperature | Time |
| Development (activator processing) | 40° C. | 45 sec |

-continued

| Processing step 2 | | |
|---|---|---|
| Bleach-fix | 40° C. | 45 sec |
| Rinse | room temperature | 90 sec |

| (Developing Solution (activator solution containing hydrogen peroxide)) | |
|---|---|
| Water | 600 ml |
| Potassium carbonate | 30 g |
| Hydrogen peroxide (30%) | 20 ml |
| Potassium chloride | 5 g |
| Hydroxylethylidene-1,1-diphosphonic acid (30%) | 4 ml |
| pH (at 25° C. by using sulfuric acid) | 10.5 |

The bleach-fix solution and the rinsing solution used in the above were used.

The maximum color density (Dmax) part and the minimum color density (Dmin) part of the processed Samples were measured using blue light, green light, and red light, respectively. The difference between the maximum color density and the minimum color density ΔDmaxB, ΔDmaxG, and ΔDmaxC were shown in Table 5.

TABLE 5

| Sample | ΔDmin. | | | ΔDmax. | | | |
|---|---|---|---|---|---|---|---|
| No. | B | G | R | B | G | R | Remarks |
| 600 | 0 | 0 | 0 | 0 | 0 | 0 | Comparative example |
| 601 | 0.26 | 0.34 | 0.27 | 0.63 | 0.56 | 0.57 | " |
| 602 | 0.23 | 0.37 | 0.25 | 0.52 | 0.48 | 0.43 | " |
| 603 | 0.03 | 0.01 | 0.01 | 1.01 | 1.06 | 1.06 | This invention |
| 604 | 0.04 | 0.02 | 0.01 | 1.03 | 1.09 | 1.06 | " |
| 605 | 0.03 | 0.02 | 0.01 | 1.00 | 1.07 | 1.04 | " |
| 606 | 0.05 | 0.03 | 0.02 | 1.06 | 1.11 | 1.07 | " |
| 607 | 0.03 | 0.01 | 0.01 | 1.02 | 0.98 | 1.05 | " |
| 608 | 0.04 | 0.02 | 0.01 | 1.05 | 0.99 | 1.05 | " |
| 609 | 0.03 | 0.01 | 0.01 | 1.01 | 1.06 | 1.42 | " |
| 610 | 0.03 | 0.02 | 0.01 | 1.00 | 1.07 | 1.33 | " |
| 611 | 0.03 | 0.01 | 0.01 | 1.00 | 1.01 | 1.02 | " |
| 612 | 0.05 | 0.03 | 0.02 | 1.00 | 1.03 | 1.03 | " |
| 613 | 0.03 | 0.01 | 0.01 | 1.02 | 1.02 | 1.01 | " |
| 614 | 0.04 | 0.02 | 0.01 | 1.01 | 1.03 | 1.00 | " |
| 615 | 0.02 | 0.01 | 0.01 | 1.09 | 1.06 | 1.42 | " |
| 616 | 0.03 | 0.01 | 0.01 | 1.06 | 1.03 | 1.40 | " |
| 617 | 0.03 | 0.02 | 0.01 | 1.03 | 1.01 | 1.36 | " |

As is apparent from the results shown in Table 5, when any color-developing agent precursor was not contained, of course, if the processing was carried out with a processing solution free from any color-developing agent, color formation did not take place. In the case of the light-sensitive material containing Comparative Compound EXD1 or EXD2, color formation took place, but stain due to the dye-formation resulted, conspicuously, by storage. In the light-sensitive material of the present invention containing the color-developing agent precursor for use in the present invention, stain due to the dye-formation hardly resulted even under such storage conditions, and an image high in difference of density between the maximum color density and the minimum color density, and excellent in discrimination, could be obtained.

Example 7

Samples (703), (704), (705), and (706) were prepared in the same manner as for Samples (603), (604), (605), and (606) prepared in Example 6, except that a solid dispersion of 1,5-diphenyl-3-pyrazolidone was added into the second layer and the fourth layer of each sample, with the amount of the solid dispersion being 0.03 $g/m^2$ in the second layer, and 0.02 $g/m^2$ in the fourth layer.

In the same manner as in Example 6, they were subjected to a forced thermal test and gradation exposure/processing. The value obtained by subtracting ΔDmin of Samples (603), (604), (605), and (606) from ΔDim of Samples (703), (704), (705), and (706) was called ΔΔDmin, and the value obtained by subtracting ΔDmax of Samples (603), (604), (605), and (606) from ΔDmax of Samples (703), (704), (705), and (706) was called ΔΔDmax.

Further, by letting the sensitivity of each of Samples (603), (604), (605), and (606) at the density of 0.3 be 100, the sensitivity of each of corresponding Samples (703), (704), (705), and (706) was designated the relative sensitivity S.

The results are shown in Table 6.

TABLE 6

| | ΔΔDmin. | | | ΔΔDmax. | | | S | | | |
|---|---|---|---|---|---|---|---|---|---|---|
| Sample No. | B | G | R | B | G | R | B | G | R | Remarks |
| 703 | 0 | 0 | 0 | 0.22 | 0.21 | 0.18 | 118 | 121 | 123 | This invention |
| 704 | 0 | 0 | 0 | 0.21 | 0.22 | 0.18 | 115 | 118 | 121 | " |
| 705 | 0 | 0 | 0 | 0.18 | 0.21 | 0.15 | 113 | 115 | 118 | " |
| 706 | 0 | 0 | 0 | 0.22 | 0.23 | 0.19 | 117 | 119 | 122 | " |

As is apparent from the results shown in Table 6, it was found that, when an auxiliary developing agent was added to a light-sensitive material of the present invention, the sensitivity and the color density could be improved without impairing the storage stability.

Example 8

The samples (600) to (617) were processed and evaluated in the same manner as in Example 6, except that the following exposure to light was carried out.

(Exposure to Light)

Light having a wavelength of 473 nm, taken out by wavelength conversion of a YAG solid laser (oscillation wavelength, 946 nm) by an SHG crystal of $KNbO_3$, using, as a light source, a semiconductor laser GaAlAs (oscillation wavelength, 808.5 nm) serving as an excitation light source; light having a wavelength of 532 nm, taken out by wavelength conversion of a $YVO_4$ solid laser (oscillation wavelength, 1064 nm) by an SHG crystal of KTP, using, as a light source, a semiconductor laser GaAlAs (oscillation wavelength: 808.7 nm) serving as an excitation light source; and light from AlGaInP (oscillation wavelength, about 670 nm; Type No. TOLD 9211, manufactured by Toshiba Corporation) were used. The laser beams of the apparatus could be scanned successively by a rotating polyhedron over a color print paper moved vertically to the scanning direction for exposure to light. Using this apparatus, the amount of light was varied, to find the relationship D-log E between the density (D) of the light-sensitive material and the amount of light (E). At that time, with respect to the laser beams having three wavelengths, the amounts of the lights were modulated using an external modulator, to control the exposure amounts. In this scanning exposure, the density of the picture element was 400 dpi, and the average exposure time per picture element was about $5\times10^{-8}$ sec. The temperature of the semiconductor lasers was kept constant by using Peltier elements to suppress the fluctuation of the amounts of lights due to the temperature.

As a result, it was found that, even in the case of an image formed by digital exposure with high intensity, the light-sensitive material of the present invention in which the color-developing agent precursor for use in the present invention was used, hardly resulted in stain due to the dye-formation, and it could give an image that was high in the difference of density between the maximum color density and the minimum color density and excellent in discrimination.

Example 9

A sample that was the same as Sample (201) described in an Example of JP-A-9-146237 was prepared (Sample (a-1)).

Each of Samples (a-2), (a-3), (a-4), (a-5), (a-6), and (a-7) was prepared by adding each of ExD1, ExD2, (2), (3), (11), and (46) used in Example 6 to the emulsified dispersion of each of the emulsion layers in Sample (a-1) in a molar amount equivalent to the coupler contained in each emulsified dispersion.

The prepared samples were subjected to a forced thermal test in the same manner as in Example 6 in the present invention. Also, after the prepared samples were subjected to gradation exposure using a three-color separation filter for sensitometry, they were processed in accordance with the processing method of Example 1 of JP-A-9-146237, except that, as the color-developing solution, an activator solution prepared by excluding sodium sulfite and 4-amino-N-ethyl-N-(β-hydroxyethyl)-3-methylaniline sulfate from the above color-developing solution of JP-A-9-146237, and adding 20 ml of hydrogen peroxide (30%) per liter thereto, was used.

After the samples were subjected to a forced thermal test, the processed samples were evaluated in the same manner as in Example 6, and it was found that, even in the case of such negative-type photographing materials, when the color-developing agent precursor was built in according to the present invention, the storage stability was good, like in Example 6, and images high in difference of density between the maximum color density and the minimum color density, and therefore excellent in discrimination, could be obtained.

Example 10

A sample that was the same as Sample (101) described in an Example of U.S. Pat. No. 4,956,269 was prepared (Sample (b-1)).

Each of Samples (b-2), (b-3), (b-4), (b-5), (b-6), and (b-7) was prepared by adding each of ExD1, ExD2, (2), (3), (11), and (46) used in Example 6 to the emulsified dispersion of each of the emulsion layers in Sample (b-1), in a molar amount equivalent to the coupler contained in each emulsified dispersion.

The prepared samples were subjected to a forced thermal test in the same manner as in Example 6 in the present specification. Also, after the prepared samples were subjected to gradation exposure using a three-color separation filter for sensitometry, they were processed in accordance with the processing method of an Example of U.S. Pat. No. 4,956,269, except that, as the color-developing solution, an activator solution prepared by excluding sodium sulfite and 4-amino-3-methyl-N-ethyl-N-β-(methansulfonamido) ethylaniline sulfate from the above color-developing solution of U.S. Pat. No. 4,956,269 and adding 20 ml of hydrogen peroxide (30%) per liter thereto, was used.

After the samples were subjected to a forced thermal test, the processed samples were evaluated in the same manner as in Example 6, and it was found that even in the case of such a reversal-type photographing materials, when the color-developing agent precursor was built in according to the present invention, the storage stability was good like Example 6, and an image high in difference of density between the maximum color density and the minimum color density and therefore excellent in discrimination, could be obtained.

Having described our invention as related to the present embodiments, it is our intention that the invention not be limited by any of the details of the description, unless otherwise specified, but rather be construed broadly within its spirit and scope as set out in the accompanying claims.

What we claim is:

1. An aromatic-aldehyde compound, represented by the following formula (4):

formula (4)

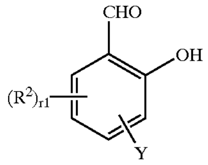

wherein $R^2$ represents a hydroxyl group, a halogen atom, an alkyl group, a cycloalkyl group, an aryl group, a heterocyclic group, an alkoxy group, an aryloxy group, an acylamino group, a sulfonylamino group, an unsubstituted amino group, a monoalkylamino group, a dialkylamino group, an arylamino group, or an alkylarylamino group; or $R^2$'s may bond together to represent a 5- or 6-membered ring, in some cases; Y is positioned in the ortho position or the para position with respect to the formyl group and represents a methylene group substituted by at least one selected from a group consisting of an alkylthio group, an arylthio group, an acyloxy group, a chlorocarbonyloxy group, an alkoxycarbonyloxy group, and an aminocarbonyloxy group; r1 is an integer of 0 to 3; and, when r1 is 2 or more, $R^2$'s are the same or different.

2. An aromatic-aldehyde compound represented by the following formula (5):

formula (5)

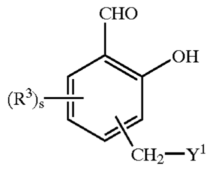

wherein $R^3$ represents a hydroxyl group, an alkyl group, a cycloalkyl group, an aryl group, an alkoxy group, an aryloxy group, an acylamino group, a sulfonylamino group, an unsubstituted amino group, a monoalkylamino group, a dialkylamino group, an arylamino group, or an alkylarylamino group, or $R^3$'s may bond together to represent a 5- or 6-membered ring in some cases; $—CH_2—$ is positioned in the ortho position or the para position with respect to the formyl group, $Y^1$ represents an alkylthio group, an arylthio group, a chlorocarbonyloxy group, an alkoxycarbonyloxy group, or an aminocarbonyloxy group, s is an integer of 0 to 3; and when s is 2 or more, $R^3$'s are the same or different.

3. A compound represented by the following formula (6):

formula (6)

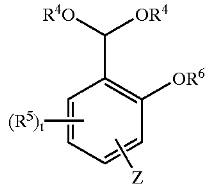

wherein $R^4$ represents an alkyl group, an aryl group, or an acyl group, or $R^4$'s may bond together to represent a 5- or 6-membered ring in some cases; $R^5$ represents a hydroxyl group, a halogen atom, an alkyl group, a cycloalkyl group, an aryl group, a heterocyclic group, an alkoxy group, an aryloxy group, an acylamino group, a sulfonylamino group, an unsubstituted amino group, a monoalkylamino group, a dialkylamino group, an arylamino group, or an alkylarylamino group, or $R^5$'s may bond together to represent a 5- or 6-membered ring in some cases; $R^6$ represents a hydrogen atom, an alkyl group, or an acyl group, Z is positioned in the ortho position or the para position with respect to the $(R^4O)_2CH$ group and represents a methylene group substituted by at least one selected from a group consisting of an alkylthio group, an arylthio group, an acyloxy group, an alkoxycarbonyloxy group, and an aminocarbonyloxy group, t is an integer of 0 to 3, and when t is 2 or more, $R^5$'s are the same or different.

4. A compound represented by the following formula (7):

formula (7)

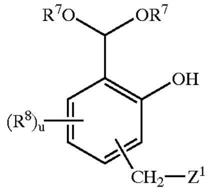

wherein $R^7$ represents an alkyl group or an aryl group, or $R^7$'s may bond together to represent a 5- or 6-membered ring in some cases; $R^8$ represents a hydroxyl group, an alkyl group, an aryl group, an alkoxy group, or an aryloxy group, or $R^8$'s may bond together to represent a 5- or 6-membered ring in some cases; $—CH_2—$ is positioned in the ortho position or the para position with respect to the $(R^7O)_2CH$ group, $Z^1$ represents an alkylthio group, an arylthio group, an alkoxycarbonyloxy group, or an aminocarbonyloxy group, u is an integer of 0 to 3, and when u is 2 or more, $R^8$'s are the same or different.

* * * * *